US012752019B2

(12) United States Patent
Smith et al.

(10) Patent No.: US 12,752,019 B2
(45) Date of Patent: Oct. 6, 2026

(54) ENGINEERED MEGANUCLEASES HAVING SPECIFICITY FOR A RECOGNITION SEQUENCE IN THE HYDROXYACID OXIDASE 1 GENE

(71) Applicant: Precision BioSciences, Inc., Durham, NC (US)

(72) Inventors: James Jefferson Smith, Morrisville, NC (US); Janel Lape, Wake Forest, NC (US); John Morris, Raleigh, NC (US)

(73) Assignee: Precision BioSciences, Inc., Durham, NC (US)

( * ) Notice: Subject to any disclaimer, the term of this patent is extended or adjusted under 35 U.S.C. 154(b) by 164 days.

(21) Appl. No.: 18/260,578

(22) PCT Filed: Jan. 7, 2022

(86) PCT No.: PCT/US2022/011659

§ 371 (c)(1),
(2) Date: Jul. 6, 2023

(87) PCT Pub. No.: WO2022/150616

PCT Pub. Date: Jul. 14, 2022

(65) Prior Publication Data

US 2024/0299585 A1 Sep. 12, 2024

Related U.S. Application Data

(60) Provisional application No. 63/241,426, filed on Sep. 7, 2021, provisional application No. 63/136,097, filed on Jan. 11, 2021, provisional application No. 63/135,515, filed on Jan. 8, 2021.

(51) Int. Cl.

| | |
|---|---|
| ***A61K 48/00*** | (2006.01) |
| ***A61P 13/00*** | (2006.01) |
| ***C12N 9/04*** | (2006.01) |
| ***C12N 9/22*** | (2006.01) |
| ***C12N 15/86*** | (2006.01) |
| ***C12N 15/90*** | (2006.01) |

(52) U.S. Cl.
CPC ...... *A61K 48/0058* (2013.01); *A61K 48/0075* (2013.01); *A61P 13/00* (2018.01); *C12N 9/0006* (2013.01); *C12N 9/22* (2013.01); *C12N 15/86* (2013.01); *C12N 15/907* (2013.01); *C12Y 101/03015* (2013.01); *C12N 2750/14143* (2013.01)

(58) Field of Classification Search
None
See application file for complete search history.

(56) References Cited

FOREIGN PATENT DOCUMENTS

WO WO 2020/132659 A1 6/2020

OTHER PUBLICATIONS

Arnould et al., Protein Eng. Design Select. 24(1-2):27-31 (2011) (Year: 2011).*

* cited by examiner

*Primary Examiner* — Thomas J. Visone
(74) *Attorney, Agent, or Firm* — Womble Bond Dickinson (US) LLP

(57) ABSTRACT

Disclosed are engineered meganucleases that bind and cleave a recognition sequence within a hydroxyacid oxidase 1 (HAO1) gene. The present invention also encompasses methods of using such engineered meganucleases to make genetically-modified cells. Further, the invention encompasses pharmaceutical compositions comprising engineered meganuclease proteins, or nucleic acids encoding engineered meganucleases of the invention, and the use of such compositions for treatment of primary hyperoxaluria type I (PH1).

24 Claims, 28 Drawing Sheets

Specification includes a Sequence Listing.

```
                                  HAO 25            HAO 26
                                 Half-Site         Half-Site
HAO 25-26                   ATGGAAGCTGTATCCAAGGATG    SEQ ID NO:3
Recognition Sequence        TACCTTCGACATAGGTTCCTAC    SEQ ID NO:4
```

FIG. 1

```
HAO 25-26L.908     MNTKYNKEFLLYLAGFVDSDGSIWAFIEPCQTVKFKHRLRLSLNVTQKTQRRWFLDKLVD   60
HAO 25-26L.907     MNTKYNKEFLLYLAGFVDSDGSIWAHIDPCQTVKFKHRLRLSLNVTQKTQRRWFLDKLVD   60
HAO 25-26L.550     MNTKYNKEFLLYLAGFVDADGSIWATILPCQSAKFKHRLKLQLNVTQKTQRRWFLDKLVD   60
HAO 25-26x.268     MNTKYNKEFLLYLAGFVDSDGSIWATINPCQPAKFKHRLKLQLNVTQKTQRRWFLDKLVD   60
HAO 25-26x.227     MNTKYNKEFLLYLAGFVDADGSIYATIRPVQRAKFKHSLRLFFNVSQKTQRRWFLDKLVD   60
HAO 25-26L.1128    MNTKYNKEFLLYLAGFVDADGSIWAHIEPCQWVKFKHRLRLSLNVTQKTQRRWFLDKLVD   60
HAO 25-26L.1434    MNTKYNKEFLLYLAGFVDADGSIWAYIEPCQWVKFKHRLKLQLNVTQKTQRRWFLDKLVD   60
                   ****************** **** * * * *  **** * *  ** **************

HAO 25-26L.908     EIGVGYVRDTGSVSQYILSEIKPLHNFLTQLQPFLKLKQKQANLVLKIIEQLPSAKESPD   120
HAO 25-26L.907     EIGVGYVRDTGSVSQYVLSEIKPLHNFLTQLQPFLKLKQKQANLVLKIIEQLPSAKESPD   120
HAO 25-26L.550     EIGVGYVRDTGSVSQYVLSEIKPLHNFLTQLQPFLKLKQKQANLVLKIIEQLPSAKESPD   120
HAO 25-26x.268     EIGVGYVRDTGSVSQYVLSQIKPLHNFLTQLQPFLKLKQKQANLVLKIIEQLPSAKESPD   120
HAO 25-26x.227     EIGVGYVLDKGSVSYYILSQIKPLHNFLTQLQPFLKLKQKQANLVLKIIEQLPSAKESPD   120
HAO 25-26L.1128    EIGVGYVRDTGSVSQYHLSEIKPLHNFLTQLQPFLKLKQKQANLVLKIIEQLPSAKESPD   120
HAO 25-26L.1434    EIGVGYVRDTGSVSQYMLSEIKPLHNFLTQLQPFLKLKQKQANLVLKIIEQLPSAKESPD   120
                   ******* * **** * ** ****************************************

HAO 25-26L.908     KFLEVCTWVDQIAALNDSKTRKTTSETVRAVLDSLPGSVGGLSPSQASSAASSASSSPGS   180
HAO 25-26L.907     KFLEVCTWVDQIAALNDSKTRKTTSETVRAVLDSLPGSVGGLSPSQASSAASSASSSPGS   180
HAO 25-26L.550     KFLEVCTWVDQIAALNDSKTRKTTSETVRAVLDSLPGSVGGLSPSQASSAASSASSSPGS   180
HAO 25-26x.268     KFLEVCTWVDQIAALNDSKTRKTTSETVRAVLDSLPGSVGGLSPSQASSAASSASSSPGS   180
HAO 25-26x.227     KFLEVCTWVDQIAALNDSKTRKTTSETVRAVLDSLPGSVGGLSPSQASSAASSASSSPGS   180
HAO 25-26L.1128    KFLEVCTWVDQIAALNDSKTRKTTSETVRAVLDSLPGSVGGLSPSQASSAASSASSSPGS   180
HAO 25-26L.1434    KFLEVCTWVDQIAALNDSKTRKTTSETVRAVLDSLPGSVGGLSPSQASSAASSASSSPGS   180
                   ************************************************************
```

FIG. 3

```
HAO 25-26L.908     GISEALRAGAGSGTGYNKEFLLYLAGFVDGDGSIYAKIRPQQASKFKHVLELVFEVTQST     240
HAO 25-26L.907     GIPEALRAGAGSGTGYNKEFLLYLAGFVDGDGSIYAKIRPQQAAKFKHVLELVFEVTQST     240
HAO 25-26L.550     GISEALRAGAGSGTGYNKEFLLYLAGFVDGDGSIYAKIRPQQASKFKHVLELVFEVTQST     240
HAO 25-26x.268     GISEALRAGAGSGTGYNKEFLLYLAGFVDGDGSIYAKIRPQQCSKFKHVLELVFEVTQST     240
HAO 25-26x.227     GISEALRAGAGSGTGYNKEFLLYLAGFVDGDGSIFAQIRPRQGHKFKHGLELSFEVTQHT     240
HAO 25-26L.1128    GISEALRAGAGSGTGYNKEFLLYLAGFVDGDGSIYAKIRPQQASKFKHVLELVFEVTQST     240
HAO 25-26L.1434    GISEALRAGAGSGTGYNKEFLLYLAGFVDGDGSIYAKIRPQQASKFKHVLELVFEVTQST     240
                   ** ******************************* * *** *  **** *** ***** *

HAO 25-26L.908     QRRWFLDKLVDEIGVGYVVYDWKQASMYRLSQIKPLHNFLTQLQPFLKLKQKQANLVLKII     300
HAO 25-26L.907     QRRWFLDKLVDEIGVGYVVYDWKQASMYRLSQIKPLHNFLTQLQPFLKLKQKQANLVLKII     300
HAO 25-26L.550     QRRWFLDKLVDEIGVGYVVYDWKQASMYRLSQIKPLHNFLTQLQPFLKLKQKQANLVLKII     300
HAO 25-26x.268     QRRWFLDKLVDEIGVGYVVYDWKQASMYRLSEIKPLHNFLTQLQPFLKLKQKQANLVLKII     300
HAO 25-26x.227     KRRWFLDKLVDEIGVGYVVYDCGPACSYRLSQIKPLHNFLTQLQPFLKLKQKQANLVLKII     300
HAO 25-26L.1128    QRRWFLDKLVDEIGVGYVVYDWKQASMYRLSQIKPLHNFLTQLQPFLKLKQKQANLVLKII     300
HAO 25-26L.1434    QRRWFLDKLVDEIGVGYVVYDWKQASMYRLSQIKPLHNFLTQLQPFLKLKQKQANLVLKII     300
                   *******************   *  **** ******************************

HAO 25-26L.908     EQLPSAKESPDKFLEVCTWVDQIAALNDSRTRKTTSETVRAVLDSLSEKKKSSP     354 (SEQ ID NO: 5)
HAO 25-26L.907     EQLPSAKESPDKFLEVCTWVDQIAALNDSKTRKTTSETVRAVLDSLSEKKKSSP     354 (SEQ ID NO: 6)
HAO 25-26L.550     EQLPSAKESPDKFLEVCTWVDQIAALNDSRTRKTTSETVRAVLDSLSEKKKSSP     354 (SEQ ID NO: 7)
HAO 25-26x.268     EQLPSAKESPDKFLEVCTWVDQIAALNDSKTRKTTSETVRAVLDSLSEKKKSSP     354 (SEQ ID NO: 8)
HAO 25-26x.227     EQLPSAKESPDKFLEVCTWVDQIAALNDSRTRKTTSETVRAVLDSLSEKKKSSP     354 (SEQ ID NO: 9)
HAO 25-26L.1128    EQLPSAKESPDKFLEVCTWVDQIAALNDSKTRKTTSETVRAVLDSLSEKKKSSP     354 (SEQ ID NO: 10)
HAO 25-26L.1434    EQLPSAKESPDKFLEVCTWVDQIAALNDSKTRKTTSETVRAVLDSLSEKKKSSP     354 (SEQ ID NO: 11)
                   ***************************** ************************
```

FIG. 3 (continued)

ENGINEERED MEGANUCLEASES HAVING SPECIFICITY FOR A RECOGNITION SEQUENCE IN THE HYDROXYACID OXIDASE 1 GENE

CROSS-REFERENCE TO RELATED APPLICATIONS

This application is a national stage filing under 35 U.S.C. 371 of International PCT Application No. PCT/US2022/011659, filed on Jan. 7, 2022, which was published by the International Bureau in English on Jul. 14, 2022, and which claims benefit to U.S. Provisional Application No. 63/135,515, filed on Jan. 8, 2021, U.S. Provisional Application No. 63/136,097, filed on Jan. 11, 2021, and U.S. Provisional Application No. 63/241,426, filed on Sep. 7, 2021, the entire contents of each of which are incorporated by reference herein.

FIELD OF THE INVENTION

The invention relates to the field of molecular biology and recombinant nucleic acid technology. In particular, the invention relates to engineered meganucleases having specificity for a recognition sequence within a hydroxyacid oxidase 1 (HAO1) gene. Such engineered meganucleases are useful in methods for treating primary hyperoxaluria.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Jan. 7, 2022, is named P109070056WO00-SEQ-EPG, and is 73,264 bytes in size.

BACKGROUND OF THE INVENTION

Primary hyperoxaluria type 1 ("PH1") is a rare autosomal recessive disorder, caused by a mutation in the AGXT gene. The disorder results in deficiency of the liver-specific enzyme alanine:glyoxylate aminotransferase (also referred to as alanine-glyoxylate transaminase, or AGT), which is encoded by AGXT and is found in peroxisomes. The AGXT gene is responsible for conversion of glyoxylate to glycine in the liver. Absence or mutation of this protein results in overproduction and excessive urinary excretion of oxalate, causing recurrent urolithiasis (i.e., kidney stones) and nephrocalcinosis (i.e., calcium oxalate deposits in the kidneys). As glomerular filtration rate declines due to progressive renal involvement, oxalate accumulates leading to systemic oxalosis. The diagnosis is based on clinical and sonographic findings, urine oxalate assessment, enzymology and/or DNA analysis. While early conservative treatment has aimed to maintain renal function, in chronic kidney disease Stages 4 and 5, the best outcomes to date have been achieved with combined liver-kidney transplantation (Cochat et al. *Nephrol Dial Transplant* 27: 1729-36). However, no approved therapeutics exist for treatment of PH1.

PH1 is the most common form of primary hyperoxaluria and has an estimated prevalence of 1 to 3 cases in 1 million in Europe and approximately 32 cases per 1,000,000 in the Middle East, with symptoms appearing before four years of age in half of the patients. It accounts for 1 to 2% of cases of pediatric end-stage renal disease (ESRD), according to registries from Europe, the United States, and Japan (Harambat et al. *Clin J Am Soc Nephrol* 7: 458-65).

Hydroxyacid oxidase 1 (HAO1), which is also referred to as glycolate oxidase, is the enzyme responsible for converting glycolate to glyoxylate in the mitochondrial/peroxisomal glycine metabolism pathway in the liver and pancreas. When AGXT is incapable of converting glyoxylate to glycine, excess glyoxylate is converted in the cytoplasm to oxalate by lactate dehydrogenase (LDHA). While glycolate is a harmless intermediate of the glycine metabolism pathway, accumulation of glyoxylate (via, e.g., an AGXT mutation) drives oxalate accumulation, which ultimately results in the PH1 disease.

The present invention involves the use of site-specific, rare-cutting nucleases that are engineered to recognize DNA sequences within the HAO1 genetic sequence. In a particular embodiment of the invention, the DNA break-inducing agent is an engineered homing endonuclease (also called a "meganuclease"). Homing endonucleases are a group of naturally-occurring nucleases which recognize 15-40 basepair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), *Q. Rev. Biophys.* 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), *Nucleic Acids Res.* 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers.

I-CreI (SEQ ID NO: 1) is a member of the LAGLIDADG (SEQ ID NO: 2) family of homing endonucleases which recognizes and cuts a 22 basepair recognition sequence in the chloroplast chromosome of the algae *Chlamydomonas reinhardtii*. Genetic selection techniques have been used to modify the wild-type I-CreI cleavage site preference (Sussman et al. (2004), *J. Mol. Biol.* 342: 31-41; Chames et al. (2005), *Nucleic Acids Res.* 33: e178; Seligman et al. (2002), *Nucleic Acids Res.* 30: 3870-9, Arnould et al. (2006), *J. Mol. Biol.* 355: 443-58). Methods for rationally-designing mono-LAGLIDADG (SEQ ID NO: 2) homing endonucleases were described which are capable of comprehensively redesigning I-CreI and other homing endonucleases to target widely-divergent DNA sites, including sites in mammalian, yeast, plant, bacterial, and viral genomes (WO 2007/047859).

As first described in International Publication No. WO 2009/059195, I-CreI and its engineered derivatives are normally dimeric but can be fused into a single polypeptide using a short peptide linker that joins the C-terminus of a first subunit to the N-terminus of a second subunit (Li, et al. (2009) *Nucleic Acids Res.* 37:1650-62; Grizot, et al. (2009) *Nucleic Acids Res.* 37:5405-19.) Thus, a functional "single-chain" meganuclease can be expressed from a single transcript. This, coupled with the extremely low frequency of off-target cutting observed with engineered meganucleases makes them the preferred endonuclease for the present invention.

The present invention provides novel engineered meganucleases that bind and cleave a recognition sequence within exon 2 of the HAO1 gene, generating a modified HAO1 gene that no longer encodes a full-length and active HAO1 protein. Further, the disclosed engineered meganucleases are effective at generating a modified HAO1 gene, are shown to reduce HAO1 protein expression, and are shown to increase serum glycolate levels in in vivo models. Accordingly, the present invention fulfills a need in the art for gene therapy approaches to treat PH1.

SUMMARY OF THE INVENTION

The present invention provides engineered meganucleases that bind and cleave a recognition sequence within exon 2 of the HAO1 gene. In particular embodiments, the engineered meganucleases of the disclosure bind and cleave the HAO 25-26 recognition sequence (SEQ ID NO: 3) in exon 2 of the HAO1 gene. The present invention further provides methods comprising the delivery of an engineered meganuclease protein, or a gene encoding an engineered meganuclease, to a eukaryotic cell in order to produce a genetically-modified eukaryotic cell. The present invention also provides pharmaceutical compositions and methods for treatment of primary hyperoxaluria and reduction of oxalate levels, which utilize an engineered meganuclease of the invention.

The present invention improves upon engineered meganucleases previously described in the art that target sequences in the HAO1 gene. When generating an endonuclease for therapeutic administration to a patient, it is critical that on-target specificity is increased while reducing or eliminating off-target cutting within the target cell genome. Here, Applicants have developed engineered meganucleases that target the HAO 25-26 recognition sequence. The meganucleases of the present invention have novel and unique sequences which were generated through extensive experimentation. Additionally, the meganucleases described herein have a number of improved and unexpected properties when compared to previously disclosed engineered meganucleases, including a significant reduction in off-target cleavage in the host cell genome. In particular, the engineered meganucleases described herein demonstrate a significant increase in the formation of indels (i.e., insertions or deletions at the cleavage site) in the HAO gene in cell lines, and effectively generate indels at the HAO 25-26 recognition sequence in vivo. Thus, the meganucleases of the invention further advance the art in a number of ways that are necessary for development of a clinical product targeting treatment of primary hyperoxaluria.

Thus, in some aspects, the disclosure provides an engineered meganuclease that binds and cleaves a recognition sequence comprising SEQ ID NO: 3 within a hydroxyacid oxidase 1 (HAO1) gene, wherein the engineered meganuclease comprises a first subunit and a second subunit, wherein the first subunit binds to a first recognition half-site of the recognition sequence and comprises a first hypervariable (HVR1) region, and wherein the second subunit binds to a second recognition half-site of the recognition sequence and comprises a second hypervariable (HVR2) region.

In some embodiments, the HVR1 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 of any one of SEQ ID NOs: 5-11. In some embodiments, the HVR1 region comprises an amino acid sequence having at least 95% sequence identity to an amino acid sequence corresponding to residues 24-79 of any one of SEQ ID NOs: 5-11. In some embodiments, the HVR1 region comprises an amino acid sequence having at least 99% sequence identity to an amino acid sequence corresponding to residues 24-79 of any one of SEQ ID NOs: 5-11. In some embodiments, the HVR1 region comprises one or more residues corresponding to residues 24, 26, 28, 30, 32, 33, 38, 40, 42, 44, 46, 68, 70, 75, and 77 of any one of SEQ ID NOs: 5-11. In some embodiments, the HVR1 region comprises residues corresponding to residues 24, 26, 28, 30, 32, 33, 38, 40, 42, 44, 46, 68, 70, 75, and 77 of any one of SEQ ID NOs: 5-11. In some embodiments, the HVR1 region comprises a residue corresponding to residue 43 of any one of SEQ ID NOs: 5-8, 10, and 11. In some embodiments, the HVR1 region comprises Y, R, K, or D at a residue corresponding to residue 66 of any one of SEQ ID NOs: 5-11. In some embodiments, the HVR1 region comprises residues 24-79 of any one of SEQ ID NOs: 5-11.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 7-153 of any one of SEQ ID NOs: 5-11. In some embodiments, the first subunit comprises an amino acid sequence having at least 95% sequence identity to residues 7-153 of any one of SEQ ID NOs: 5-11. In some embodiments, the first subunit comprises an amino acid sequence having at least 99% sequence identity to residues 7-153 of any one of SEQ ID NOs: 5-11. In some embodiments, the first subunit comprises a residue corresponding to residue 19 of any one of SEQ ID NOs: 5-11. In some embodiments, the first subunit comprises G, S, or A at a residue corresponding to residue 19 of any one of SEQ ID NOs: 5-11. In some embodiments, the first subunit comprises a residue corresponding to residue 80 of any one of SEQ ID NOs: 8 and 9. In some embodiments, the first subunit comprises E, Q, or K at a residue corresponding to residue 80 of any one of SEQ ID NOs: 5-11. In some embodiments, the first subunit comprises residues 7-153 of any one of SEQ ID NOs: 5-11.

In some embodiments, the HVR2 region comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 215-270 of any one of SEQ ID NOs: 5-11. In some embodiments, the HVR2 region comprises an amino acid sequence having at least 95% sequence identity to an amino acid sequence corresponding to residues 215-270 of any one of SEQ ID NOs: 5-11. In some embodiments, the HVR2 region comprises an amino acid sequence having at least 99% sequence identity to an amino acid sequence corresponding to residues 215-270 of any one of SEQ ID NOs: 5-11. In some embodiments, the HVR2 region comprises one or more residues corresponding to residues 215, 217, 219, 221, 223, 224, 229, 231, 233, 235, 237, 259, 261, 266, and 268 of any one of SEQ ID NOs: 5-11. In some embodiments, the HVR2 region comprises residues corresponding to residues 215, 217, 219, 221, 223, 224, 229, 231, 233, 235, 237, 259, 261, 266, and 268 of any one of SEQ ID NOs: 5-11.

In some embodiments, the HVR2 comprises a residue corresponding to residue 239 of any one of SEQ ID NOs:

5-11. In some embodiments, the HVR2 comprises a residue corresponding to residue 241 of SEQ ID NO: 9. In some embodiments, the HVR2 comprises a residue corresponding to residue 262 of any one of SEQ ID NOs: 5-8, 10, and 11. In some embodiments, the HVR2 comprises a residue corresponding to residue 263 of any one of SEQ ID NOs: 5-11. In some embodiments, the HVR2 comprises a residue corresponding to residue 264 of any one of SEQ ID NOs: 5-11. In some embodiments, the HVR2 comprises a residue corresponding to residue 265 of SEQ ID NO: 9. In some embodiments, the HVR2 region comprises Y, R, K, or D at a residue corresponding to residue 257 of any one of SEQ ID NOs: 5-11. In some embodiments, the HVR2 region comprises residues 215-270 of any one of SEQ ID NOs: 5-11.

In some embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to residues 198-344 of any one of SEQ ID NOs: 5-11. In some embodiments, the second subunit comprises an amino acid sequence having at least 95% sequence identity to residues 198-344 of any one of SEQ ID NOs: 5-11. In some embodiments, the second subunit comprises an amino acid sequence having at least 99% sequence identity to residues 198-344 of any one of SEQ ID NOs: 5-11. In some embodiments, the second subunit comprises a residue corresponding to residue 271 of any one of SEQ ID NOs: 5-7, 9, 10, and 11. In some embodiments, the second subunit comprises a residue corresponding to residue 330 of any one of SEQ ID NOs: 5, 7, and 9. In some embodiments, the second subunit comprises G, S, or A at a residue corresponding to residue 210 of any one of SEQ ID NOs: 5-11. In some embodiments, the second subunit comprises E, Q, or K at a residue corresponding to residue 271 of any one of SEQ ID NOs: 5-11. In some embodiments, the second subunit comprises residues 198-344 of any one of SEQ ID NOs: 5-11.

In some embodiments, the engineered meganuclease is a single-chain meganuclease comprising a linker, wherein the linker covalently joins the first subunit and the second subunit.

In some embodiments, the engineered meganuclease comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to any one of SEQ ID NOs: 5-11. In some embodiments, the engineered meganuclease comprises an amino acid sequence having at least 95% sequence identity to any one of SEQ ID NOs: 5-11. In some embodiments, the engineered meganuclease comprises an amino acid sequence having at least 96% sequence identity to any one of SEQ ID NOs: 5-11. In some embodiments, the engineered meganuclease comprises an amino acid sequence having at least 97% sequence identity to any one of SEQ ID NOs: 5-11. In some embodiments, the engineered meganuclease comprises an amino acid sequence having at least 98% sequence identity to any one of SEQ ID NOs: 5-11. In some embodiments, the engineered meganuclease comprises an amino acid sequence having at least 99% sequence identity to any one of SEQ ID NOs: 5-11.

In some embodiments, the engineered meganuclease comprises an amino acid sequence of any one of SEQ ID NOs: 5-11.

In some embodiments, the engineered meganuclease is encoded by a nucleic acid sequence having at least 80%, at least 85%, at least 90%, at least 91%, at least 92%, at least 93%, at least 94%, at least 95%, at least 96%, at least 97%, at least 98%, at least 99%, or more, sequence identity to a nucleic acid sequence of any one of SEQ ID NOs: 26-34. In some embodiments, the engineered meganuclease is encoded by a nucleic acid sequence of any one of SEQ ID NOs: 26-34.

In some embodiments, the engineered meganuclease comprises a nuclear localization signal (NLS). In certain embodiments, the NLS is positioned at the N-terminus of the engineered meganuclease. In certain embodiments, the NLS is positioned at the C-terminus of the engineered meganuclease. In certain embodiments, the engineered meganuclease comprises a first NLS at the N-terminus and a second NLS at the C-terminus. In some such embodiments, the first NLS and the second NLS are identical. In other such embodiments, the first NLS and the second NLS are not identical. In some embodiments, the NLS comprises an amino acid sequence having at least 90%, at least 91%, at least 92%, at least 93%, at least 94%, at least 95%, at least 96%, at least 97%, at least 98%, at least 99%, or more, sequence identity to SEQ ID NO: 37. In particular embodiments, the NLS comprises an amino acid sequence of SEQ ID NO: 37. In some embodiments, the NLS comprises an amino acid sequence having at least 90%, at least 91%, at least 92%, at least 93%, at least 94%, at least 95%, at least 96%, at least 97%, at least 98%, at least 99%, or more, sequence identity to SEQ ID NO: 35. In particular embodiments, the NLS comprises an amino acid sequence of SEQ ID NO: 35.

In another aspect, the present disclosure provides a polynucleotide comprising a nucleic acid sequence encoding one of the engineered meganucleases provided herein.

In another aspect, the present disclosure provides a polynucleotide comprising a nucleic acid sequence encoding an engineered meganuclease described herein, wherein the nucleic acid sequence comprises: (a) a 5' untranslated region (UTR); (b) a coding sequence encoding an engineered meganuclease described herein; (c) a 3' UTR; and (d) a poly A sequence.

In some embodiments, the 5' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 60. In some embodiments, the 5' UTR comprises SEQ ID NO: 60. In some embodiments, the 3' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 61. In some embodiments, the 3' UTR comprises SEQ ID NO: 61. In some embodiments, the 5' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 60 and the 3' UTR comprises at least 80% at least 85%, at least 90%, at least 91%, at least 92%, at least 93%, at least 94%, at least 95%, at least 96%, at least 97%, at least 98%, at least 99%, or more, sequence identity to SEQ ID NO: 61. In some embodiments, the 5' UTR comprises SEQ ID NO: 60 and the 3' UTR comprises identity to SEQ ID NO: 61.

In some embodiments, the 5' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 62. In some embodiments, the 5' UTR comprises SEQ ID NO: 62. In some embodiments, the 3' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 63. In some embodiments, the 3' UTR comprises SEQ ID NO: 63. In some embodiments, the 5' UTR comprises at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 62 and the 3' UTR comprises at least 80% at least 85%, at least 90%, at least 91%, at least 92%, at least 93%, at least 94%, at least 95%, at least 96%, at least 97%, at least 98%, at least 99%, or more, sequence identity to SEQ ID NO: 63. In some embodiments, the 5' UTR comprises SEQ ID NO: 62 and the 3' UTR comprises identity to SEQ ID NO: 63.

In some embodiments, the 5' UTR comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 62; wherein the 5' UTR does not comprise an upstream uATG sequence or upstream open reading frame sequence; wherein the engineered meganuclease comprises a first NLS at the N-terminus and a second NLS at the C-terminus of the engineered nuclease; wherein the first NLS and the second NLS are identical and comprise at least 90%, at least 91%, at least 92%, at least 93%, at least 94%, at least 95%, at least 96%, at least 97%, at least 98%, at least 99%, or more sequence identity to SEQ ID NO: 35; wherein the coding sequence of the engineered meganuclease has been modified to have reduced thymidine or uridine content; wherein the 3' UTR comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 63; and wherein the 3' UTR does not comprise any AU rich elements (AREs). In some embodiments, the 5' UTR comprises SEQ ID NO: 62; wherein the engineered meganuclease comprises a first NLS at the N-terminus and a second NLS at the C-terminus of the engineered nuclease; wherein the first NLS and the second NLS comprise SEQ ID NO: 35; wherein the coding sequence of the engineered meganuclease has been modified to have reduced thymidine or uridine content; and wherein the 3' UTR comprises SEQ ID NO: 63. In some such embodiments, the first NLS and/or the second NLS comprises a sequence having at least 90%, at least 91%, at least 92%, at least 93%, at least 94%, at least 95%, at least 96%, at least 97%, at least 98%, at least 99%, or more sequence identity to SEQ ID NO: 37. In some embodiments, the first NLS and/or the second NLS comprises a sequence set forth in SEQ ID NO: 37. In some embodiments, the first NLS comprises a sequence set forth in SEQ ID NO: 37 and the second NLS comprises a sequence set forth in SEQ ID NO: 35.

In some embodiments, a nucleic acid sequence encoding an engineered meganuclease described herein comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 33. In some embodiments, a nucleic acid sequence encoding an engineered meganuclease described herein comprises SEQ ID NO: 33. In some embodiments, a nucleic acid sequence encoding an engineered meganuclease described herein comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 34. In some embodiments, a nucleic acid sequence encoding an engineered meganuclease described herein comprises SEQ ID NO: 34.

In some embodiments, the polynucleotide comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 66. In some embodiments, the polynucleotide comprises SEQ ID NO: 66. In some embodiments, the polynucleotide comprises at least 80, at least 85%, at least 90%, at least 91%, at least 92%, at least 93%, at least 94%, at least 95%, at least 96%, at least 97%, at least 98%, at least 99%, or more, sequence identity to SEQ ID NO: 67. In some embodiments, the polynucleotide comprises SEQ ID NO: 67. In some embodiments, the polynucleotide further comprises a promoter set forth in SEQ ID NO: 68 that is operably linked to the coding sequence for the engineered meganuclease.

In some embodiments, the polynucleotide is an mRNA. In some embodiments, the mRNA comprises a 5' cap. In some embodiments, the 5' cap comprises a 5' methylguanosine gap. In some embodiments, a uridine present in the mRNA is pseudouridine or 2-thiouridine. In some embodiments, a uridine present in the mRNA is methylated. In some embodiments, a uridine present in the mRNA is N1-methylpseudouridine, 5-methyluridine, or 2'-O-methyluridine.

In another aspect, the present disclosure provides a recombinant DNA construct comprising a polynucleotide comprising a nucleic acid sequence encoding one of the engineered meganucleases provided herein.

In some embodiments, the recombinant DNA construct encodes a recombinant virus comprising the polynucleotide. In some embodiments, the recombinant virus is a recombinant adenovirus, a recombinant lentivirus, a recombinant retrovirus, or a recombinant adeno-associated virus (AAV). In some embodiments, the recombinant virus is a recombinant AAV. In some embodiments, the recombinant AAV comprises an AAV8 capsid. In some embodiments, the recombinant AAV comprises an AAV9 capsid.

In some embodiments of the recombinant DNA constructs provided herein, the polynucleotide comprises a promoter operably linked to the nucleic acid sequence encoding the engineered meganuclease. In some embodiments, the promoter is a liver-specific promoter. In some embodiments, the promoter is a thyroxine binding globulin (TBG) promoter.

In another aspect, the present disclosure provides a lipid nanoparticle composition comprising lipid nanoparticles comprising a polynucleotide, wherein the polynucleotide comprises a nucleic acid sequence encoding one of the engineered meganucleases provided herein. In some embodiments, the polynucleotide is an mRNA.

In other aspects, the present disclosure provides pharmaceutical compositions. In some embodiments, the pharmaceutical composition comprises a pharmaceutically acceptable carrier and one of the engineered meganucleases provided herein. In some embodiments, the pharmaceutical composition comprises a pharmaceutically acceptable carrier and one of the polynucleotides provided herein. In some embodiments, the pharmaceutical composition comprises a pharmaceutically acceptable carrier and one of the recombinant DNA constructs provided herein. In some embodiments, the pharmaceutical composition comprises a pharmaceutically acceptable carrier and one of the recombinant viruses provided herein. In some embodiments, the pharmaceutical composition comprises a pharmaceutically acceptable carrier and one of the lipid nanoparticle compositions provided herein.

In some aspects, the present disclosure provides a method for producing a genetically-modified eukaryotic cell having a modified target sequence in an HAO1 gene of the genetically-modified eukaryotic cell, the method comprising: introducing into a eukaryotic cell a polynucleotide comprising a nucleic acid sequence encoding one of the engineered meganucleases provided herein, wherein the engineered meganuclease is expressed in the eukaryotic cell, wherein the engineered meganuclease produces a cleavage site in the HAO1 gene at a recognition sequence comprising SEQ ID NO: 3, and wherein the cleavage site is repaired by non-homologous end joining resulting in the modified target sequence.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the polynucleotide is an mRNA. In some embodiments, the polynucleotide is introduced into the eukaryotic cell by a lipid nanoparticle or by a recombinant virus. In some embodiments, the recombinant virus is a recombinant AAV.

In another aspect, the present disclosure provides a method for producing a genetically-modified eukaryotic cell having a modified target sequence in an HAO1 gene of the genetically-modified eukaryotic cell, the method comprising: introducing into a eukaryotic cell one of the engineered meganucleases provided herein, wherein the engineered meganuclease produces a cleavage site in the HAO1 gene at a recognition sequence comprising SEQ ID NO: 3, and wherein the cleavage site is repaired by non-homologous end joining resulting in the modified target sequence.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In another aspect, the present disclosure provides a method for producing a genetically-modified eukaryotic cell comprising an exogenous sequence of interest inserted into an HAO1 gene of the genetically-modified eukaryotic cell, the method comprising introducing into a eukaryotic cell one or more polynucleotides comprising: a first nucleic acid sequence encoding one of the engineered meganucleases provided herein, wherein the engineered meganuclease is expressed in the eukaryotic cell, and a second nucleic acid sequence comprising the sequence of interest, wherein the engineered meganuclease produces a cleavage site in the HAO1 gene at a recognition sequence comprising SEQ ID NO: 3, and wherein the sequence of interest is inserted into the HAO1 gene at the cleavage site.

In some embodiments, the second nucleic acid sequence further comprises nucleic acid sequences homologous to nucleic acid sequences flanking the cleavage site, and the sequence of interest is inserted at the cleavage site by homologous recombination.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the first nucleic acid sequence is introduced into the eukaryotic cell as an mRNA. In some embodiments, the second nucleic acid sequence is introduced into the eukaryotic cell as a double-stranded DNA (dsDNA). In some embodiments, the first nucleic acid sequence is introduced into the eukaryotic cell by a recombinant virus. In some embodiments, the second nucleic acid sequence is introduced into the eukaryotic cell by a recombinant virus. In some embodiments, the recombinant virus is a recombinant AAV.

In another aspect, the present disclosure provides a method for producing a genetically-modified eukaryotic cell comprising an exogenous sequence of interest inserted into an HAO1 gene of the genetically-modified eukaryotic cell, the method comprising introducing into a eukaryotic cell one of the engineered meganucleases provided herein, and a polynucleotide comprising the sequence of interest, wherein the engineered meganuclease produces a cleavage site in the HAO1 gene at a recognition sequence comprising SEQ ID NO: 3, and wherein the sequence of interest is inserted into the HAO1 gene at the cleavage site.

In some embodiments, the nucleic acid sequence further comprises nucleic acid sequences homologous to nucleic acid sequences flanking the cleavage site, and the sequence of interest is inserted at the cleavage site by homologous recombination.

In some embodiments, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the nucleic acid sequence is introduced into the eukaryotic cell as a double-stranded DNA (dsDNA). In some embodiments, the nucleic acid sequence is introduced into the eukaryotic cell by a recombinant virus. In some embodiments, the recombinant virus is a recombinant AAV.

In another aspect, the present disclosure provides a method for producing a genetically-modified eukaryotic cell comprising a modified HAO1 gene, the method comprising introducing into a eukaryotic cell: (a) a polynucleotide comprising a nucleic acid sequence encoding one of the engineered meganucleases provided herein, wherein the engineered meganuclease is expressed in the eukaryotic cell; or (b) one of the engineered meganucleases provided herein;

wherein the engineered meganuclease produces a cleavage site in the HAO1 gene at a recognition sequence comprising SEQ ID NO: 3 and generates a modified HAO1 gene.

In some embodiments, the cleavage site is repaired by non-homologous end joining, and the modified HAO1 gene comprises an insertion or deletion that disrupts expression of the encoded HAO1 protein. In some embodiments, the modified HAO1 gene does not encode a full-length endogenous HAO1 protein. In some embodiments, expression of a full-length endogenous HAO1 protein by the genetically-modified eukaryotic cell is reduced compared to a control cell.

In some embodiments of the methods provided herein, the eukaryotic cell is a mammalian cell. In some embodiments, the mammalian cell is a liver cell. In some embodiments, the mammalian cell is a liver progenitor cell or stem cell. In some embodiments, the mammalian cell is a human cell.

In some embodiments, the method is performed in vivo. In some embodiments, the method is performed in vitro.

In some embodiments, the polynucleotide is an mRNA. In some embodiments, the polynucleotide is one of the mRNAs provided herein. In some embodiments, the polynucleotide is a recombinant DNA construct. In some embodiments, the polynucleotide is one of the recombinant DNA constructs provided herein. In some embodiments, the polynucleotide is introduced into the eukaryotic cell by a lipid nanoparticle. In some embodiments, the polynucleotide is introduced into the eukaryotic cell by a lipid nanoparticle described herein.

In some embodiments, the polynucleotide is introduced into the eukaryotic cell by a recombinant virus. In some embodiments, the recombinant virus is one of the recombinant viruses provided herein. In some embodiments, the recombinant virus is a recombinant AAV. In some embodiments, the recombinant AAV virus comprises an AAV8 capsid.

In some embodiments, the polynucleotide comprises a promoter operably linked to the nucleic acid sequence encoding the engineered meganuclease. In some embodiments, the promoter is a liver-specific promoter. In some embodiments, the liver-specific promoter is a TBG promoter.

In some embodiments, the genetically-modified eukaryotic cell comprises reduced levels of oxalate (or reduced levels of glyoxylate) compared to a control cell. In some embodiments, the genetically-modified eukaryotic cell comprises increased levels of glycolate compared to a control cell.

In another aspect, the present disclosure provides a method for modifying an HAO1 gene in a target cell in a subject, the method comprising delivering to the target cell: (a) a polynucleotide comprising a nucleic acid sequence encoding an engineered meganuclease provided herein, wherein the engineered meganuclease is expressed in the target cell; or (b) one of the engineered meganucleases provided herein; wherein the engineered meganuclease produces a cleavage site in the HAO1 gene at a recognition sequence comprising SEQ ID NO: 3 and generates a modified HAO1 gene in the target cell.

In some embodiments of the methods provided herein, the cleavage site is repaired by non-homologous end joining, and wherein the modified HAO1 gene comprises an insertion or deletion that disrupts expression of the encoded HAO1 protein.

In some embodiments, the modified HAO1 gene does not encode a full-length endogenous HAO1 protein. In some embodiments, expression of a full-length endogenous HAO1 protein by the target cell is reduced compared to a control cell. In some embodiments, levels of full-length endogenous HAO1 protein are reduced in the subject relative to a control subject.

In some embodiments, the subject is a mammal. In some embodiments, the target cell is a liver cell. In some embodiments, the target cell is a liver progenitor cell or stem cell. In some embodiments, the subject is a human.

In some embodiments, the target cell comprising the modified HAO1 gene comprises reduced levels of oxalate compared to a control cell. In some embodiments, the target cell comprising the modified HAO1 gene comprises increased levels of glycolate compared to a control cell.

In some embodiments, the subject comprises reduced levels of serum oxalate compared to a control subject following modification of the HAO1 gene in the target cell. In some embodiments, the subject comprises reduced levels of oxalate in the urine and/or the serum compared to a control subject following modification of the HAO1 gene in the target cell.

In some embodiments, the subject comprises increased levels of serum glycolate compared to a control subject following modification of the HAO1 gene in the target cell. In some embodiments, the subject comprises an increased ratio of serum glycolate to serum creatinine compared to a control subject following modification of the HAO1 gene in the target cell.

In some embodiments, the subject comprises a decreased ratio of serum oxalate to serum creatinine compared to a control subject following modification of the HAO1 gene in the target cell. In some embodiments, the subject exhibits a decreased level of calcium precipitates in the kidney compared to a control subject following modification of the HAO1 gene in the target cell.

In some embodiments, the subject exhibits a decreased risk of renal failure compared to a control subject following modification of the HAO1 gene in the target cell.

In another aspect, the present disclosure provides a method for treating primary hyperoxaluria-1 (PH1) in a subject, the method comprising administering to the subject: (a) a therapeutically-effective amount of a polynucleotide comprising a nucleic acid sequence encoding an engineered meganuclease provided herein, wherein the engineered meganuclease is delivered to a target cell in the subject, and wherein the engineered meganuclease is expressed in the target cell; or (b) a therapeutically-effective amount of one of the engineered meganucleases provided herein, wherein the engineered meganuclease is delivered to the target cell in the subject; wherein the engineered meganuclease produces a cleavage site in the HAO1 gene at a recognition sequence comprising SEQ ID NO: 3 and generates a modified HAO1 gene in the target cell.

In some embodiments, the cleavage site is repaired by non-homologous end joining, and wherein the modified HAO1 gene comprises an insertion or deletion that disrupts expression of the encoded HAO1 protein. In some embodiments, the modified HAO1 gene does not encode a full-length endogenous HAO1 protein.

In some embodiments, the subject is a mammal. In some embodiments, the subject is a human.

In some embodiments, the target cell is a liver cell. In some embodiments, the target cell is a liver progenitor cell or stem cell.

In some embodiments, the polynucleotide is an mRNA. In some embodiments, the polynucleotide is one of the mRNAs provided herein. In some embodiments, the polynucleotide is a recombinant DNA construct. In some embodiments, the polynucleotide is one of the recombinant DNA constructs provided herein. In some embodiments, the polynucleotide is delivered to the target cell by a lipid nanoparticle. In some embodiments, the polynucleotide is delivered to the target cell by a lipid nanoparticle described herein.

In some embodiments, the polynucleotide is delivered to the target cell by a recombinant virus. In some embodiments, the recombinant virus is one of the recombinant viruses described herein. In some embodiments, the recombinant virus is a recombinant AAV. In some embodiments, the recombinant AAV comprises an AAV8 capsid.

In some embodiments, the polynucleotide comprises a promoter operably linked to the nucleic acid sequence encoding the engineered meganuclease. In some embodiments, the promoter is a liver-specific promoter. In some embodiments, the liver-specific promoter is a TBG promoter.

In some embodiments, the target cell comprising the modified HAO1 gene comprises reduced levels of oxalate compared to a control cell. In some embodiments, the target cell comprising the modified HAO1 gene comprises increased levels of glycolate compared to a control cell.

In some embodiments, the subject comprises reduced levels of serum oxalate compared to a control subject following modification of the HAO1 gene in the target cell. In some embodiments, the subject comprises reduced levels of oxalate in urine compared to a control subject following modification of the HAO1 gene in the target cell. In some embodiments, the subject comprises increased levels of serum glycolate compared to a control subject following modification of the HAO1 gene in the target cell.

In some embodiments, the subject comprises an increased ratio of serum glycolate to serum creatinine compared to a control subject following modification of the HAO1 gene in the target cell. In some embodiments, the subject comprises a decreased ratio of serum oxalate to serum creatinine compared to a control subject following modification of the HAO1 gene in the target cell.

In some embodiments, the subject exhibits a decreased level of calcium precipitates in the kidney compared to a control subject following modification of the HAO1 gene in the target cell. In some embodiments, the subject exhibits a decreased risk of renal failure compared to a control subject following modification of the HAO1 gene in the target cell.

In another aspect, the present disclosure provides a genetically-modified eukaryotic cell prepared by the method of any one of the methods provided herein.

In another aspect, the present disclosure provides a genetically-modified eukaryotic cell comprising in its genome a modified HAO1 gene, wherein the modified HAO1 gene comprises an insertion or a deletion positioned within SEQ ID NO: 3.

In some embodiments, the insertion or deletion disrupts expression of the encoded HAO1 protein. In some embodiments, the modified HAO1 gene does not encode a full-length endogenous HAO1 protein. In some embodiments, expression of a full-length endogenous HAO1 protein by the genetically-modified eukaryotic cell is reduced compared to a control cell.

In some embodiments, the genetically-modified eukaryotic cell is a genetically-modified mammalian cell. In some embodiments, the genetically-modified mammalian cell is a genetically-modified liver cell. In some embodiments, the genetically-modified mammalian cell is a genetically-modified liver progenitor cell or stem cell. In some embodiments, the genetically-modified mammalian cell is a genetically-modified human cell.

In some embodiments, the genetically-modified eukaryotic cell comprises reduced levels of oxalate compared to a control cell. In some embodiments, the genetically-modified eukaryotic cell comprises increased levels of glycolate compared to a control cell.

In some embodiments, the genetically-modified eukaryotic cell comprises one of the engineered meganucleases, or a polynucleotide comprising a nucleic acid sequence encoding one of the engineered meganucleases, provided herein.

In some aspects, the present disclosure provides compositions for use as a medicament. In some embodiments, the disclosure provides one of the engineered meganucleases provided herein, for use as a medicament. In some embodiments, the disclosure provides one of the polynucleotides provided herein, for use as a medicament. In some embodiments, the disclosure provides one of the mRNAs provided herein, for use as a medicament. In some embodiments, the disclosure provides one of the recombinant DNA constructs provided herein, for use as a medicament. In some embodiments, the disclosure provides one of the recombinant viruses provided herein, for use as a medicament. In some embodiments, the disclosure provides a lipid nanoparticle comprising one of the compositions provided herein, for use as a medicament.

BRIEF DESCRIPTION OF THE FIGURES

FIG. 1 provides a sequence listing showing the sense (SEQ ID NO: 3) and anti-sense (SEQ ID NO: 4) sequences for the HAO 25-26 recognition sequence in the human hydroxyacid oxidase 1 (HAO1) gene. The HAO 25-26 recognition sequence targeted by engineered meganucleases described herein comprises two recognition half-sites (i.e., HAO25 and HAO26). Each recognition half-site comprises 9 base pairs, separated by a 4 basepair central sequence.

FIG. 3 provides an alignment of amino acid sequences of HAO 25-26 meganucleases exemplified herein (SEQ ID NOs: 5-11).

FIG. 6A shows low dose of mRNA (2 ng). FIG. 6B shows high dose of mRNA (20 ng).

FIG. 7A shows low dose of mRNA (5 ng). FIG. 7B shows high dose of mRNA (50 ng).

FIG. 8A shows low dose of mRNA (8 ng). FIG. 8B shows high dose of mRNA (250 ng).

FIG. 10A shows the concentrations (in μM) (or "levels") of glycolate in serum. FIG. 10B shows changes in serum glycolate as a percentage from baseline levels.

FIG. 11A shows the concentrations (in μM) of glycolate in serum in 3 animals receiving HAO 25-26x.227 and 2 animals receiving PBS. FIG. 11B shows μM of glycolate in serum in 3 animals receiving HAO 25-26x.268 and 2 animals receiving PBS. FIG. 11C shows μM of glycolate in serum in 3 animals receiving HAO 3-4x.47 and 2 animals receiving PBS.

FIG. 12A shows indel observed in individual animals. FIG. 12B shows average of indels observed in each group.

FIG. 13A shows digital western blot of liver samples from individual animals for HAO1 protein and vinculin. FIG. 13B is graphs showing levels of HAO1 protein in livers of individual animals normalized to vinculin (left panel: HAO 3-4; right panel: HAO 25-26). FIG. 13C is graphs showing averaged levels of HAO1 protein in livers of each group normalized to vinculin and relative to PBS controls.

FIG. 16A shows low dose of mRNA (5 ng). FIG. 16B shows high dose of mRNA (50 ng). FIG. 16C shows time course of editing in Hep3B cells following introduction of mRNA encoding the HAO 25-26L.550 meganuclease.

FIG. 18A shows low dose of mRNA (5 ng). FIG. 18B shows high dose of mRNA (50 ng).

BRIEF DESCRIPTION OF THE SEQUENCES

Figure 2:
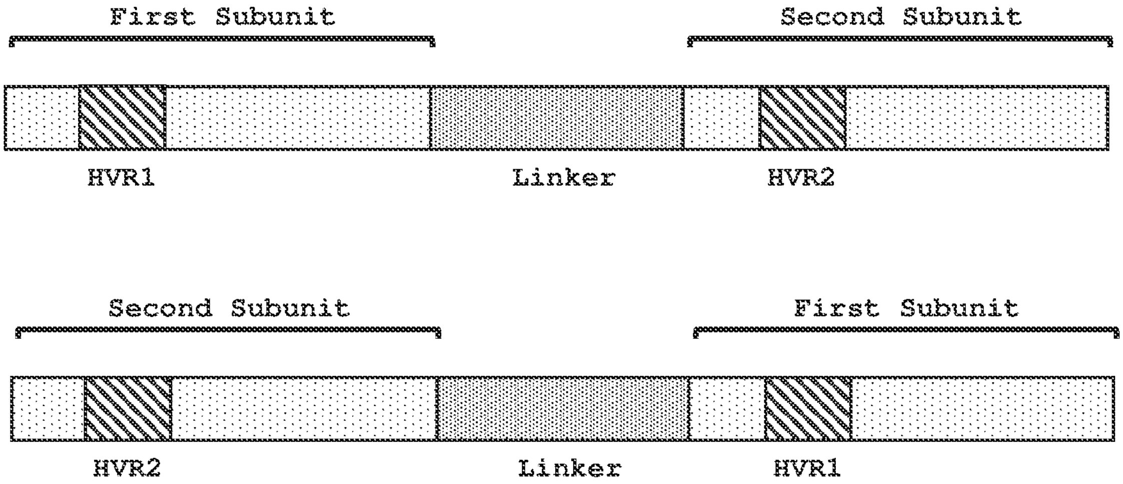
FIG. 2 illustrates that the engineered meganucleases described herein comprise two subunits, wherein the first subunit comprising the HVR1 region binds to a first recognition half-site (e.g., HAO25) and the second subunit comprising the HVR2 region binds to a second recognition half-site (e.g., HAO26). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.
Figure 4:
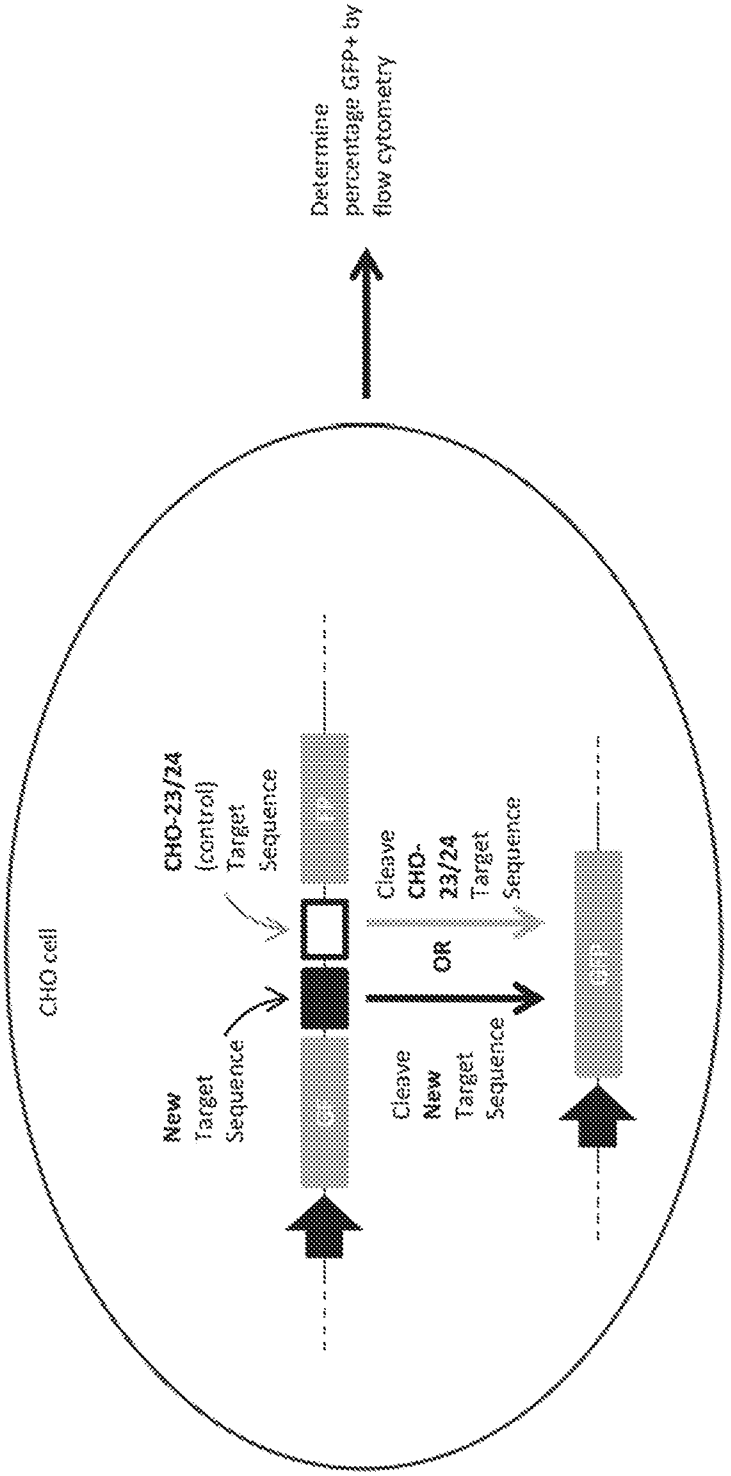
FIG. 4 provides a schematic of a reporter assay in CHO cells for evaluating engineered meganucleases targeting the HAO 25-26 recognition sequence. For the engineered meganucleases described herein, a CHO cell line was produced in which a reporter cassette was integrated stably into the genome of the cell. The reporter cassette comprised, in 5' to 3' order: an SV40 Early Promoter; the 5' 2/3 of the GFP gene; the recognition sequence for an engineered meganuclease described herein (e.g., the HAO 25-26 recognition sequence); the recognition sequence for the CHO-23/24 meganuclease (WO/2012/167192); and the 3' 2/3 of the GFP gene. Cells stably transfected with this cassette did not express GFP in the absence of a DNA break-inducing agent. Meganucleases were introduced by transduction of an mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

SEQ ID NO: 1 sets forth the amino acid sequence of a wild-type I-CreI meganuclease.

SEQ ID NO: 2 sets forth the amino acid sequence of a LAGLIDADG motif.

SEQ ID NO: 3 sets forth the nucleic acid sequence of an HAO 25-26 recognition sequence (sense).

SEQ ID NO: 4 sets forth the nucleic acid sequence of an HAO 25-26 recognition sequence (antisense).

SEQ ID NO: 5 sets forth the amino acid sequence of an HAO 25-26L.908 meganuclease.

SEQ ID NO: 6 sets forth the amino acid sequence of an HAO 25-26L.907 meganuclease.

SEQ ID NO: 7 sets forth the amino acid sequence of an HAO 25-26L.550 meganuclease.

SEQ ID NO: 8 sets forth the amino acid sequence of an HAO 25-26x.268 meganuclease.

SEQ ID NO: 9 sets forth the amino acid sequence of an HAO 25-26x.227 meganuclease.

SEQ ID NO: 10 sets forth the amino acid sequence of an HAO 25-26L.1128 meganuclease.

SEQ ID NO: 11 sets forth the amino acid sequence of an HAO 25-26L.1434 meganuclease.

SEQ ID NO: 12 sets forth the amino acid sequence of an HAO 25-26L.908 meganuclease HAO25-binding subunit.

SEQ ID NO: 13 sets forth the amino acid sequence of an HAO 25-26L.907 meganuclease HAO25-binding subunit.

SEQ ID NO: 14 sets forth the amino acid sequence of an HAO 25-26L.550 meganuclease HAO25-binding subunit.

SEQ ID NO: 15 sets forth the amino acid sequence of an HAO 25-26x.268 meganuclease HAO25-binding subunit.

SEQ ID NO: 16 sets forth the amino acid sequence of an HAO 25-26x.227 meganuclease HAO25-binding subunit.

SEQ ID NO: 17 sets forth the amino acid sequence of an HAO 25-26L.1128 meganuclease HAO25-binding subunit.

SEQ ID NO: 18 sets forth the amino acid sequence of an HAO 25-26L.1434 meganuclease HAO25-binding subunit.

SEQ ID NO: 19 sets forth the amino acid sequence of an HAO 25-26L.908 meganuclease HAO26-binding subunit.

SEQ ID NO: 20 sets forth the amino acid sequence of an HAO 25-26L.907 meganuclease HAO26-binding subunit.

SEQ ID NO: 21 sets forth the amino acid sequence of an HAO 25-26L.550 meganuclease HAO26-binding subunit.

SEQ ID NO: 22 sets forth the amino acid sequence of an HAO 25-26x.268 meganuclease HAO26-binding subunit.

SEQ ID NO: 23 sets forth the amino acid sequence of an HAO 25-26x.227 meganuclease HAO26-binding subunit.

SEQ ID NO: 24 sets forth the amino acid sequence of an HAO 25-26L.1128 meganuclease HAO26-binding subunit.

SEQ ID NO: 25 sets forth the amino acid sequence of an HAO 25-26L.1434 meganuclease HAO26-binding subunit.

SEQ ID NO: 26 sets forth the nucleic acid sequence encoding an HAO 25-26L.908 meganuclease.

SEQ ID NO: 27 sets forth the nucleic acid sequence encoding an HAO 25-26L.907 meganuclease.

SEQ ID NO: 28 sets forth the nucleic acid sequence encoding an HAO 25-26L.550 meganuclease.

SEQ ID NO: 29 sets forth the nucleic acid sequence encoding an HAO 25-26x.268 meganuclease.

SEQ ID NO: 30 sets forth the nucleic acid sequence encoding an HAO 25-26x.227 meganuclease.

SEQ ID NO: 31 sets forth the nucleic acid sequence of an HAO 25-26L.1128 meganuclease.

SEQ ID NO: 32 sets forth the nucleic acid sequence of an HAO 25-26L.1434 meganuclease.

SEQ ID NO: 33 sets forth a codon optimized nucleic acid sequence of an HAO 25-26L.1128 meganuclease.

SEQ ID NO: 34 sets forth a codon optimized nucleic acid sequence of an HAO 25-26L.1434 meganuclease.

SEQ ID NO: 35 sets forth an amino acid sequence of an SV40 minimal nuclear localization sequence.

SEQ ID NO: 36 sets forth the nucleic acid sequence of an SV40 minimal nuclear localization sequence.

SEQ ID NO: 37 sets forth the amino acid sequence of an SV40 nuclear localization sequence.

SEQ ID NO: 38 sets forth the nucleic acid sequence of an SV40 nuclear localization sequence.

SEQ ID NO: 39 sets forth the nucleic acid sequence of a P1 probe.

SEQ ID NO: 40 sets forth the nucleic acid sequence of an F1 primer.

SEQ ID NO: 41 sets forth the nucleic acid sequence of an R1 primer.

SEQ ID NO: 42 sets forth the nucleic acid sequence of a P2 probe.

SEQ ID NO: 43 sets forth the nucleic acid sequence of an F2 primer.

SEQ ID NO: 44 sets forth the nucleic acid sequence of an R2 primer.

SEQ ID NO: 45 sets forth the nucleic acid sequence of a P3 probe.

SEQ ID NO: 46 sets forth the nucleic acid sequence of an F3 primer.

SEQ ID NO: 47 sets forth the nucleic acid sequence of an R3 primer.

SEQ ID NO: 48 sets forth the nucleic acid sequence of an F4 primer.

SEQ ID NO: 49 sets forth the nucleic acid sequence of an R4 primer.

SEQ ID NO: 50 sets forth the nucleic acid sequence of an R5 primer.

SEQ ID NO: 51 sets forth the nucleic acid sequence of a P4 probe.

SEQ ID NO: 52 sets forth the nucleic acid sequence of an F5 primer.

SEQ ID NO: 53 sets forth the nucleic acid sequence of an R6 primer.

SEQ ID NO: 54 sets forth the nucleic acid sequence of and F6 primer.

SEQ ID NO: 55 sets forth the nucleic acid sequence of an R7 primer.

SEQ ID NO: 56 sets forth the nucleic acid sequence of a P5 probe.

SEQ ID NO: 57 sets forth the nucleic acid sequence of an F7 primer.

SEQ ID NO: 58 sets forth the nucleic acid sequence of an R8 primer.

SEQ ID NO: 59 sets forth the nucleic acid sequence of a P6 probe.

SEQ ID NO: 60 sets forth the nucleic acid sequence of a 5' HBA2 UTR.

SEQ ID NO: 61 sets forth the nucleic acid sequence of a 3' WPRE UTR.

SEQ ID NO: 62 sets forth the nucleic acid sequence of a 5' ALB UTR.

SEQ ID NO: 63 sets forth the nucleic acid sequence of a 3' SNRPB transcript variant 1 UTR.

SEQ ID NO: 64 sets forth the DNA sequence of an mRNA that comprises from 5' to 3' a T7AG promoter, a 5' HBA2 UTR, an N terminal 10 amino acid SV40 nuclear localization sequence, an HAO 25-26L.1128 engineered meganuclease coding sequence, and a 3' WPRE UTR.

SEQ ID NO: 65 sets forth the DNA sequence of an mRNA that comprises from 5' to 3' a T7AG promoter, a 5' HBA2 UTR, an N terminal 10 amino acid SV40 nuclear localization sequence, an HAO 25-26L.1434 engineered meganuclease coding sequence, and a 3' WPRE UTR.

SEQ ID NO: 66 sets forth the DNA sequence of an mRNA that comprises from 5' to 3' a 5' ALB UTR, a modified Kozak sequence which overlaps the 3' end of the ALB UTR and the 5' end of a sequence encoding a nuclear localization sequence, a sequence encoding a codon optimized 10 amino acid N terminal SV40 nuclear localization sequence, a codon optimized coding sequence for an HAO 25-26L.1128 engineered meganuclease that has been optimized to reduce uridine content, a sequence encoding a codon optimized 7 amino acid minimal C terminal SV40 nuclear localization sequence, and a 3' SNRPB V1 UTR.

SEQ ID NO: 67 sets forth the DNA sequence of an mRNA that comprises from 5' to 3' a 5' ALB UTR, a modified Kozak sequence which overlaps the 3' end of the ALB UTR and the 5' end of a sequence encoding a nuclear localization sequence, a sequence encoding a codon optimized 10 amino acid N terminal SV40 nuclear localization sequence, a codon optimized coding sequence for an HAO 25-26L.1434 engineered meganuclease that has been optimized to reduce uridine content, a sequence encoding a codon optimized 7 amino acid minimal C terminal SV40 nuclear localization sequence, and a 3' SNRPB V1 UTR.

SEQ ID NO: 68 sets forth the nucleic acid sequence of a T7AG RNA polymerase promoter.

SEQ ID NO: 69 sets forth the nucleic acid sequence of a modified Kozak sequence.

SEQ ID NO: 70 sets forth the nucleic acid sequence of a codon optimized SV40 nuclear localization sequence.

SEQ ID NO: 71 sets forth the nucleic acid sequence of a codon optimized minimal SV40 nuclear localization sequence.

DETAILED DESCRIPTION OF THE INVENTION

1.1 References and Definitions

The patent and scientific literature referred to herein establishes knowledge that is available to those of skill in the art. The issued US patents, allowed applications, published foreign applications, and references, including GenBank database sequences, which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the terms "nuclease" and "endonuclease" are used interchangeably to refer to naturally-occurring or engineered enzymes, which cleave a phosphodiester bond within a polynucleotide chain. Engineered nucleases can include, without limitation, engineered meganucleases such as those described herein.

As used herein, the terms "cleave" or "cleavage" refer to the hydrolysis of phosphodiester bonds within the backbone of a recognition sequence within a target sequence that results in a double-stranded break within the target sequence, referred to herein as a "cleavage site".

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI (SEQ ID NO: 1), and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g., WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein such that cells can be transfected and maintained at 37° C. without observing deleterious effects on cell viability or significant reductions in meganuclease cleavage activity when measured using the methods described herein.

As used herein, the term "single-chain meganuclease" refers to a polypeptide comprising a pair of nuclease subunits joined by a linker. A single-chain meganuclease has the organization: N-terminal subunit-Linker-C-terminal subunit. The two meganuclease subunits will generally be non-identical in amino acid sequence and will bind non-identical DNA sequences. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two nuclease subunits into a single polypeptide. A linker may have a sequence that is found in natural proteins or may be an artificial sequence that is not found in any natural protein. A linker may be flexible and lacking in secondary structure or may have a propensity to form a specific three-dimensional structure under physiological conditions. A linker can include, without limitation, those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or 100% sequence identity to residues 154-195 of any one of SEQ ID NOs: 5-11.

As used herein, the terms "recombinant" or "engineered," with respect to a protein, means having an altered amino acid sequence as a result of the application of genetic engineering techniques to nucleic acids that encode the protein and cells or organisms that express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation, and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant or engineered. Exemplary transfection techniques of the disclosure include, but are not limited to, electroporation and lipofection using Lipofectamine (e.g., Lipofectamine® MessengerMax (ThermoFisher)).

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein, the term with respect to recombinant proteins, the term "modification" means any insertion, deletion, or substitution of an amino acid residue in the recombinant sequence relative to a reference sequence (e.g., a wild-type or a native sequence).

As used herein, the term "disrupted" or "disrupts" or "disrupts expression" or "disrupting a target sequence" refers to the introduction of a mutation (e.g., frameshift mutation) that interferes with the gene function and prevents expression and/or function of the polypeptide/expression product encoded thereby. For example, nuclease-mediated disruption of a gene can result in the expression of a truncated protein and/or expression of a protein that does not retain its wild-type function. Additionally, introduction of a donor template into a gene can result in no expression of an encoded protein, expression of a truncated protein, and/or expression of a protein that does not retain its wild-type function.

As used herein, the terms "recognition sequence" or "recognition site" refers to a DNA sequence that is bound and cleaved by a nuclease. In the case of a meganuclease, a recognition sequence comprises a pair of inverted, 9 base-pair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' overhangs. "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "target site" or "target sequence" refers to a region of the chromosomal DNA of a cell comprising a recognition sequence for a nuclease. This term embraces chromosomal DNA duplexes as well as single-stranded chromosomal DNA.

As used herein, the terms "DNA-binding affinity" or "binding affinity" means the tendency of a nuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change relative to a reference nuclease.

As used herein, the term "specificity" refers to the ability of a nuclease to bind and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art, such as unbiased identification of DSBs enabled by sequencing (GUIDE-seq), oligonucleotide (oligo) capture assay, whole genome sequencing, and long-range next generation sequencing of the recognition sequence. In some embodiments, specificity is measured using GUIDE-seq. As used herein, "specificity" is synonymous with a low incidence of cleavage of sequences different from the target sequences (non-target sequences), i.e., off-target cutting. A low incidence of off-target cutting may comprise an incidence of cleavage of non-target sequences of less than 25%, less than 20%, less than 18%, less than 15%, less than 12.5%, less than 10%, less than 9%, less than 8%, less than 7%, less than 6%, less than 5%, less than 4%, less than 3%, less than 2.5%, less than 2%, less than 1.5%, less than 1%, less than 0.75%, less than 0.5%, or less than 0.25%. Off-target cleavage by a meganuclease can be measured using any method known in the art, including for example, oligo capture analysis as described herein, a T7 endonuclease (T7E) assay as described herein, digital (droplet) PCR as described herein, targeted sequencing of particular off-target sites, exome sequencing, whole genome sequencing, direct in situ breaks labeling enrichment on streptavidin and next-generation sequencing (BLESS), genome-wide, GUIDE-seq, and linear amplification-mediated high-throughput genome-wide translocation sequencing (LAM-HTGTS) (see, e.g., Zischewski et al. (2017), Biotechnology Advances 35(1):95-104, which is incorporated by reference in its entirety).

As used herein, a meganuclease has "altered" specificity if it binds to and cleaves a recognition sequence which is not bound to and cleaved by a reference meganuclease (e.g., a wild-type) under physiological conditions, or if the rate of cleavage of a recognition sequence is increased or decreased by a biologically significant amount (e.g., at least 2×, or 2×-10×) relative to a reference meganuclease.

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, droplet digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

As used herein, "HAO1 gene" refers to a gene encoding a polypeptide having 2-hydroxyacid oxidase activity, particularly the hydroxyacid oxidase 1 polypeptide, which is also referred to as glycolate oxidase. An HAO1 gene can include a human HAO1 gene (NCBI Accession No.: NM_017545.2; NP_060015.1; Gene ID: 54363); cynomolgus monkey (*Macaca, mulatta*) HAO1 (NCBI Accession No.: XM_001116000.2, XP_001116000.1); and mouse (*Mus musculus*) HAO1, (NCBI Accession No.: NM_010403.2; NP_034533.1). Additional examples of HAO1 mRNA sequences are readily available using publicly available databases, e.g., GenBank, UniProt, OMIM, and the *Macaca* genome project web site. The term HAO1 also refers to naturally occurring DNA sequence variations of the HAO1 gene, such as a single nucleotide polymorphism (SNP) in the HAO1 gene. Exemplary SNPs may be found through the publically accessible National Center for Biotechnology Information dbSNP Short Genetic Variations database.

As used herein, the term "HAO1 polypeptide" refers to a polypeptide encoded by an HAO1 gene. The HAO1 polypeptide is also known as glycolate oxidase.

As used herein, the term "primary hyperoxaluria type 1" or "PH1" refers to a autosomal recessive disorder caused by a mutation in the gene encoding alanine glyoxylate aminotransferase (AGT), a peroxisomal vitamin $B_6$-dependent enzyme, in which the mutation results in decreased conversion of glyoxylate to glycine and consequently, an increase in conversion of glyoxylate to oxalate.

As used herein, the term "efficiency of cleavage" refers to the incidence by which a meganuclease cleaves a recognition sequence in a double-stranded DNA molecule relative to the incidence of all cleavage events by the meganuclease on the DNA molecule. "Efficiency of cleavage" is synonymous with DNA editing efficiency or on-target editing. Efficiency of cleavage and/or indel formation by a meganuclease can be measured using any method known in the art, including T7E assay, digital PCR (ddPCR), mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety). In some embodiments, efficiency of cleavage is measured by ddPCR. In some embodiments, the disclosed meganucleases generate efficiencies of cleavage of at least about 35%, 40%, 50%, 60%, 70%, 80%, 85%, 90%, 95%, 98%, or 99% at the recognition sequence.

An "indel", as used herein, refers to the insertion or deletion of a nucleobase within a nucleic acid, such as DNA. In some embodiments, it is desirable to generate one or more insertions or deletions (i.e., indels) in the nucleic acid, e.g., in a foreign nucleic acid such as viral DNA. Accordingly, as used herein, "efficiency of indel formation" refers to the incidence by which a meganuclease generates one or more indels through cleavage of a recognition sequence relative to the incidence of all cleavage events by the meganuclease on the DNA molecule. In some embodiments, efficiency of indel formation is measured by ddPCR. In some embodiments, the disclosed meganucleases generate efficiencies of indel formation of at least about 35%, 40%, 50%, 60%, 70%, 80%, 85%, 90%, 95%, 98%, or 99% at the recognition sequence. The disclosed meganucleases may generate efficiencies of cleavage and/or efficiencies of indel formation of at least about 60%, 61%, 62%, 63%, 64%, 65%, 66%, 67%, 68%, 69%, 70%, 71%, 72%, 73%, 74%, or 75% at the recognition sequence.

As used herein, the term "homologous recombination" or "HR" refers to the natural, cellular process in which a double-stranded DNA-break is repaired using a homologous DNA sequence as the repair template (see, e.g. Cahill et al. (2006), *Front. Biosci.* 11:1958-1976). The homologous DNA sequence may be an endogenous chromosomal sequence or an exogenous nucleic acid that was delivered to the cell.

As used herein, a "template nucleic acid" or "donor template" refers to a nucleic acid sequence that is desired to be inserted into a cleavage site within a cell's genome. Such template nucleic acids or donor templates can comprise, for example, a transgene, such as an exogenous transgene, which encodes a protein of interest. The template nucleic acid or donor template can comprise 5' and 3' homology arms having homology to 5' and 3' sequences, respectively, that flank a cleavage site in the genome where insertion of the template is desired. Insertion can be accomplished, for example, by homology-directed repair (HDR).

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), *Front. Biosci.* 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells.

As used herein, the term "homology arms" or "sequences homologous to sequences flanking a nuclease cleavage site" refer to sequences flanking the 5' and 3' ends of a nucleic acid molecule, which promote insertion of the nucleic acid molecule into a cleavage site generated by a nuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome. In some embodiments, the homology arms are about 500 base pairs.

As used herein, the term with respect to both amino acid sequences and nucleic acid sequences, the terms "percent identity," "sequence identity," "percentage similarity," "sequence similarity" and the like refer to a measure of the degree of similarity of two sequences based upon an alignment of the sequences that maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol. 266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein, the term "corresponding to" with respect to modifications of two proteins or amino acid sequences is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment and despite the fact that X and Y may be different numbers.

As used herein, the term "recognition half-site," "recognition sequence half-site," or simply "half-site" means a nucleic acid sequence in a double-stranded DNA molecule that is recognized and bound by a monomer of a homodimeric or heterodimeric meganuclease or by one subunit of a single-chain meganuclease or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of any one of SEQ ID NOs: 5-11. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity. In some embodiments, variable residues within a hypervariable region correspond to one or more of positions 24, 26, 28, 30, 32, 33, 38, 40, 42, 44, 46, 68, 70, 75, and 77 of any one of SEQ ID NOs: 5-11. In certain embodiments, variable residues within a hypervariable region can further correspond to residues 48, 50, and 71-73 of any one of SEQ ID NOs: 5-11. In other embodiments, variable residues within a hypervariable region correspond to one or more of positions 215, 217, 219, 221, 223, 224, 229, 231, 233, 235, 237, 239, 241, 259, 261, 262, 263, 264, 266, and 268 of any one of SEQ ID NOs: 5-11. In certain embodiments, variable residues within a hypervariable region can further correspond to residues 239, 241, and 263-265 of any one of SEQ ID NOs: 5-11.

As used herein, the term "reference level" in the context of HAO1 protein or mRNA levels refers to a level of HAO1 protein or mRNA as measured in, for example, a control cell, control cell population or a control subject, at a previous time point in the control cell, the control cell population or the subject undergoing treatment (e.g., a pre-dose baseline level obtained from the control cell, control cell population or subject), or a pre-defined threshold level of HAO1 protein or mRNA (e.g., a threshold level identified through previous experimentation).

As used herein, the term "a control" or "a control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype. A control subject may comprise, for example: a wild-type subject, i.e., of the same genotype as the starting subject for the genetic alteration which resulted in the genetically-modified subject (e.g., a subject having the same mutation in a HAO1 gene), which is not exposed to conditions or stimuli or further genetic modifications that would induce expression of altered genotype or phenotype in the subject.

As used herein, the term "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant AAV vectors, or any other vector known in the art suitable for delivering a gene to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, the term "operably linked" is intended to mean a functional linkage between two or more elements. For example, an operable linkage between a nucleic acid sequence encoding a nuclease as disclosed herein and a regulatory sequence (e.g., a promoter) is a functional link that allows for expression of the nucleic acid sequence encoding the nuclease. Operably linked elements may be contiguous or non-contiguous. When used to refer to the joining of two protein coding regions, by operably linked is intended that the coding regions are in the same reading frame.

As used herein, the terms "treatment" or "treating a subject" refers to the administration of an engineered meganuclease described herein, or a polynucleotide encoding an engineered meganuclease described herein, or a pair of such engineered meganucleases or polynucleotides, to a subject having PH1 for the purpose of reducing levels of oxalate in the urine of the subject. In some embodiments, expression of a truncated and/or non-functional version of the HAO1 protein results from cleavage by one or more of the disclosed meganucleases. In some embodiments, cleavage by one or more of the disclosed meganucleases generates a frameshift mutation or missense mutation (e.g., introduction of a stop codon) into the HAO1 gene such that it no longer encodes a full length endogenous HAO1 protein.

As used herein, the term "gc/kg" or "gene copies/kilogram" refers to the number of copies of a nucleic acid sequence encoding an engineered meganuclease described herein per weight in kilograms of a subject that is administered a polynucleotide comprising the nucleic acid sequence.

As used herein, the term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of an engineered meganuclease or pair of engineered meganucleases described herein, or polynucleotide or pair of polynucleotides encoding the same, or pharmaceutical compositions disclosed herein, increases the level of expression of a non-functional HAO1 protein (e.g., a truncated HAO1 protein) and ameliorates at least one symptom associated with PH1.

As used herein, the term "lipid nanoparticle" refers to a lipid composition having a typically spherical structure with an average diameter between 10 and 1000 nanometers. In some formulations, lipid nanoparticles can comprise at least one cationic lipid, at least one non-cationic lipid, and at least one conjugated lipid. Lipid nanoparticles known in the art that are suitable for encapsulating nucleic acids, such as mRNA, are contemplated for use in the invention.

As used herein, the recitation of a numerical range for a variable is intended to convey that the present disclosure may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 20 and ≤2 if the variable is inherently continuous.

2.1 Principle of the Invention

The present invention is based, in part, on the hypothesis that engineered meganucleases can be designed to bind and cleave recognition sequences found within a HAO1 gene (e.g., the human HAO1 gene). In particular, the meganucleases described herein bind and cleave a target sequence within exon 2 of the HAO1 gene (i.e., the HAO 25-26 recognition sequence). Once cleaved, this sequence incurs an insertion or deletion, which results in disruption of the HAO1 gene such that it no longer encodes a full length endogenous HAO1 polypeptide. As a result, it is expected that levels of the glycolate substrate in cells expressing the modified HAO1 gene will be elevated, while levels of glyoxylate in the peroxisome, and oxalate in the cytoplasm, will be reduced. This approach is effective because glycolate is a highly soluble small molecule that can be eliminated at high concentrations in the urine without affecting the kidney. Effectiveness of treatment may be evaluated by measurement of liver and/or kidney function, which may be measured by changes in concentration of biomarkers alanine transaminase (ALT), aspartate transaminase (AST), and bilirubin in the liver.

Thus, the present invention encompasses engineered meganucleases that bind and cleave a recognition sequence within exon 2. The present invention further provides methods comprising the delivery of an engineered protein, or nucleic acids encoding an engineered meganuclease, to a eukaryotic cell in order to produce a genetically-modified eukaryotic cell. Further, the present invention provides pharmaceutical compositions, methods for treatment of PH1, and methods for reducing serum oxalate levels, which utilize an engineered meganuclease having specificity for a recognition sequence positioned within exon 2 of the HAO1 gene.

The meganucleases of the disclosure may be referred to herein using the identifiers HAO 25-26x.227, HAO 25-26x.268, HAO 25-26L.550, HAO 25-26L.907, HAO 25-26L.908, and other identifiers.

2.2 Meganucleases that Bind and Cleave Recognition Sequences within a HAO1 Gene

Recognition Sequences

It is known in the art that it is possible to use a site-specific nuclease to make a DNA break in the genome of a living cell, and that such a DNA break can result in permanent modification of the genome via mutagenic NHEJ repair or via homologous recombination with a transgenic DNA sequence. NHEJ can produce mutagenesis at the cleavage site, resulting in inactivation of the allele. NHEJ-associated mutagenesis may inactivate an allele via generation of early stop codons, frameshift mutations producing aberrant non-functional proteins, or could trigger mechanisms such as nonsense-mediated mRNA decay. The use of nucleases to induce mutagenesis via NHEJ can be used to target a specific mutation or a sequence present in a wild-type allele. Further, the use of nucleases to induce a double-strand break in a target locus is known to stimulate homologous recombination, particularly of transgenic DNA sequences flanked by sequences that are homologous to the genomic target. In this manner, exogenous polynucleotides can be inserted into a target locus. Such exogenous polynucleotides can encode any sequence or polypeptide of interest.

In particular embodiments, engineered meganucleases of the invention have been designed to bind and cleave an HAO 25-26 recognition sequence (SEQ ID NO: 3). Exemplary meganucleases that bind and cleave the HAO 25-26 recognition sequence are provided in SEQ ID NOs: 5-11.

Exemplary Engineered Meganucleases

Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (e.g., the HAO25 half-site), and the second subunit binds to a second recognition half-site in the recognition sequence (e.g., the HAO26 half-site).

In particular embodiments, the meganucleases used to practice the invention are single-chain meganucleases. A single-chain meganuclease comprises an N-terminal subunit and a C-terminal subunit joined by a linker peptide. Each of the two subunits recognizes and binds to half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

As discussed, the meganucleases of the invention have been engineered to bind and cleave the HAO 25-26 recognition sequence (SEQ ID NO: 3). The HAO 25-26 recognition sequence is positioned within exon 2 of the HAO1 gene. Such recombinant meganucleases are collectively referred to herein as "HAO 25-26 meganucleases." Exemplary HAO 25-26 meganucleases are provided in SEQ ID NOs: 5-11.

Recombinant meganucleases (e.g., engineered recombinant meganucleases) of the invention comprise a first subunit, comprising a first hypervariable (HVR1) region, and a second subunit, comprising a second hypervariable (HVR2) region. Further, the first subunit binds to a first recognition half-site in the recognition sequence (e.g., the HAO25 half-site), and the second subunit binds to a second recognition half-site in the recognition sequence (e.g., the HAO26 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit.

Exemplary HAO 25-26 meganucleases of the invention are provided in Table 1 and are further described below.

a residue corresponding to residue 19 of SEQ ID NO: 5. In some embodiments, the first subunit comprises a residue corresponding to residue 19 of SEQ ID NO: 5. In some embodiments, the first subunit comprises E, Q, or K at a residue corresponding to residue 80 of SEQ ID NO: 5. In some embodiments, the first subunit comprises residues 7-153 of SEQ ID NO: 5 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 5.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 5. In some embodiments, the HVR2 region comprises one or more residues corresponding to residues 215, 217, 219, 221, 223, 224, 229, 231, 233, 235, 237, 259, 261, 266, and 268 of SEQ ID NO: 5. In some embodiments, the HVR2 region comprises residues corresponding to residues 215, 217, 219, 221, 223, 224, 229, 231, 233, 235, 237, 259, 261, 266, and 268 of SEQ ID NO: 5. In some embodiments, the HVR2 region comprises Y, R, K, or D at a residue corresponding to residue 257 of SEQ ID NO: 5. In some embodiments, the HVR2 region comprises a residue corresponding to residue 239 of SEQ ID

TABLE 1

| Meganuclease | AA SEQ ID | HAO25 Subunit Residues | HAO25 Subunit SEQ ID | *HAO25 Subunit % | HAO26 Subunit Residues | HAO26 Subunit SEQ ID | *HAO26 Subunit % |
|---|---|---|---|---|---|---|---|
| HAO 25-26L.908 | 5 | 7-153 | 12 | 100 | 198-344 | 19 | 100 |
| HAO 25-26L.907 | 6 | 7-153 | 13 | 97.96 | 198-344 | 20 | 98.64 |
| HAO 25-26L.550 | 7 | 7-153 | 14 | 94.56 | 198-344 | 21 | 100 |
| HAO 25-26x.268 | 8 | 7-153 | 15 | 94.56 | 198-344 | 22 | 97.96 |
| HAO 25-26x.227 | 9 | 7-153 | 16 | 89.8 | 198-344 | 23 | 90.48 |
| HAO 25-26L.1128 | 10 | 7-153 | 17 | 97.28 | 198-344 | 24 | 97.96 |
| HAO 25-26L.1434 | 11 | 7-153 | 18 | 95.92 | 198-344 | 25 | 90.48 |

*"HAO25 Subunit %" and "HAO26 Subunit %" represent the amino acid sequence identity between the HAO25-binding and HAO26-binding subunit regions of each meganuclease and the HAO25-binding and HAO26-binding subunit regions, respectively, of the HAO25-26L.908 meganuclease.

HAO 25-26L.908 (SEQ ID NO: 5)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 5. In some embodiments, the HVR1 region comprises one or more residues corresponding to residues 24, 26, 28, 30, 32, 33, 38, 40, 42, 44, 46, 68, 70, 75, and 77 of SEQ ID NO: 5. In some embodiments, the HVR1 region comprises residues corresponding to residues 24, 26, 28, 30, 32, 33, 38, 40, 42, 44, 46, 68, 70, 75, and 77 of SEQ ID NO: 5. In some embodiments, the HVR1 region comprises a residue corresponding to residue 43 of SEQ ID NO: 5. In some embodiments, the HVR1 region comprises Y, R, K, or D at a residue corresponding to residue 66 of SEQ ID NO: 5. In some embodiments, the HVR1 region comprises residues 24-79 of SEQ ID NO: 5 with up to 1, 2, 3, 4, 5, 6, 7, 8, 9, 10, or 11 amino acid substitutions. In some embodiments, the HVR1 region comprises residues 24-79 of SEQ ID NO: 5.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 5. In some embodiments, the first subunit comprises G, S, or A at NO: 5. In some embodiments, the HVR2 region comprises a residue corresponding to residue 262 of SEQ ID NO: 5. In some embodiments, the HVR2 region comprises a residue corresponding to residue 263 of SEQ ID NO: 5. In some embodiments, the HVR2 region comprises a residue corresponding to residue 264 of SEQ ID NO: 5. In some embodiments, the HVR2 region comprises residues 215-270 of SEQ ID NO: 5 with up to 1, 2, 3, 4, 5, 6, 7, 8, 9, 10, or 11 amino acid substitutions. In some embodiments, the HVR2 region comprises residues 215-270 of SEQ ID NO: 5.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 5. In some embodiments, the second subunit comprises G, S, or A at a residue corresponding to residue 210 of SEQ ID NO: 5. In some embodiments, the second subunit comprises E, Q, or K at a residue corresponding to residue 271 of SEQ ID NO: 5. In some embodiments, the second subunit comprises a residue corresponding to residue 271 of SEQ ID NO: 5. In some embodiments, the second subunit comprises a residue corresponding to residue 330 of SEQ ID NO: 5. In some embodiments, the second subunit comprises residues 198-344 of SEQ ID NO: 5 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 5.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 5. In some embodiments, the engineered meganuclease comprises an amino acid sequence of SEQ ID NO: 5. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 26. In some embodiments, the engineered meganuclease is encoded by a nucleic acid sequence set forth in SEQ ID NO: 26.

HAO 25-261.907 (SEQ ID NO: 6)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 6. In some embodiments, the HVR1 region comprises one or more residues corresponding to residues 24, 26, 28, 30, 32, 33, 38, 40, 42, 44, 46, 68, 70, 75, and 77 of SEQ ID NO: 6. In some embodiments, the HVR1 region comprises residues corresponding to residues 24, 26, 28, 30, 32, 33, 38, 40, 42, 44, 46, 68, 70, 75, and 77 of SEQ ID NO: 6. In some embodiments, the HVR1 region comprises a residue corresponding to residue 43 of SEQ ID NO: 6. In some embodiments, the HVR1 region comprises Y, R, K, or D at a residue corresponding to residue 66 of SEQ ID NO: 6. In some embodiments, the HVR1 region comprises residues 24-79 of SEQ ID NO: 6 with up to 1, 2, 3, 4, 5, 6, 7, 8, 9, 10, or 11 amino acid substitutions. In some embodiments, the HVR1 region comprises residues 24-79 of SEQ ID NO: 6.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 6. In some embodiments, the first subunit comprises G, S, or A at a residue corresponding to residue 19 of SEQ ID NO: 6. In some embodiments, the first subunit comprises a residue corresponding to residue 19 of SEQ ID NO: 6. In some embodiments, the first subunit comprises E, Q, or K at a residue corresponding to residue 80 of SEQ ID NO: 6. In some embodiments, the first subunit comprises residues 7-153 of SEQ ID NO: 6 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 6.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 6. In some embodiments, the HVR2 region comprises one or more residues corresponding to residues 215, 217, 219, 221, 223, 224, 229, 231, 233, 235, 237, 259, 261, 266, and 268 of SEQ ID NO: 6. In some embodiments, the HVR2 region comprises residues corresponding to residues 215, 217, 219, 221, 223, 224, 229, 231, 233, 235, 237, 259, 261, 266, and 268 of SEQ ID NO: 6. In some embodiments, the HVR2 region comprises Y, R, K, or D at a residue corresponding to residue 257 of SEQ ID NO: 6. In some embodiments, the HVR2 region comprises a residue corresponding to residue 239 of SEQ ID NO: 6. In some embodiments, the HVR2 region comprises a residue corresponding to residue 262 of SEQ ID NO: 6. In some embodiments, the HVR2 region comprises a residue corresponding to residue 263 of SEQ ID NO: 6. In some embodiments, the HVR2 region comprises a residue corresponding to residue 264 of SEQ ID NO: 6. In some embodiments, the HVR2 region comprises residues 215-270 of SEQ ID NO: 6 with up to 1, 2, 3, 4, 5, 6, 7, 8, 9, 10, or 11 amino acid substitutions. In some embodiments, the HVR2 region comprises residues 215-270 of SEQ ID NO: 6.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 6. In some embodiments, the second subunit comprises G, S, or A at a residue corresponding to residue 210 of SEQ ID NO: 6. In some embodiments, the second subunit comprises E, Q, or K at a residue corresponding to residue 271 of SEQ ID NO: 6. In some embodiments, the second subunit comprises a residue corresponding to residue 271 of SEQ ID NO: 6. In some embodiments, the second subunit comprises residues 198-344 of SEQ ID NO: 6 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 6.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 6. In some embodiments, the engineered meganuclease comprises an amino acid sequence of SEQ ID NO: 6. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 27. In some embodiments, the engineered meganuclease is encoded by a nucleic acid sequence set forth in SEQ ID NO: 27.

HAO 25-261.550 (SEQ ID NO: 7)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 7. In some embodiments, the HVR1 region comprises one or more residues corresponding to residues 24, 26, 28, 30, 32, 33, 38, 40, 42, 44, 46, 68, 70, 75, and 77 of SEQ ID NO: 7. In some embodiments, the HVR1 region comprises residues corresponding to residues 24, 26, 28, 30, 32, 33, 38, 40, 42, 44, 46, 68, 70, 75, and 77 of SEQ ID NO: 7. In some embodiments, the HVR1 region comprises a residue corresponding to residue 43 of SEQ ID NO: 7. In some embodiments, the HVR1 region comprises Y, R, K, or D at a residue corresponding to residue 66 of SEQ ID NO: 7. In some embodiments, the HVR1 region comprises residues 24-79 of SEQ ID NO: 7 with up to 1, 2, 3, 4, 5, 6, 7, 8, 9, 10, or 11 amino acid substitutions. In some embodiments, the HVR1 region comprises residues 24-79 of SEQ ID NO: 7.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 7. In some embodiments, the first subunit comprises G, S, or A at a residue corresponding to residue 19 of SEQ ID NO: 7. In some embodiments, the first subunit comprises a residue corresponding to residue 19 of SEQ ID NO: 7. In some embodiments, the first subunit comprises E, Q, or K at a residue corresponding to residue 80 of SEQ ID NO: 7. In some embodiments, the first subunit comprises residues 7-153 of SEQ ID NO: 7 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 7.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 7. In some embodiments, the HVR2 region comprises one or more residues corresponding to residues 215, 217, 219, 221, 223, 224, 229, 231, 233, 235, 237, 259, 261, 266, and 268 of SEQ ID NO: 7. In some embodiments, the HVR2 region comprises residues corresponding to residues 215, 217, 219, 221, 223, 224, 229, 231, 233, 235, 237, 259, 261, 266, and 268 of SEQ ID NO: 7. In some embodiments, the HVR2 region comprises Y, R, K, or D at a residue corresponding to residue 257 of SEQ ID NO: 7. In some embodiments, the HVR2 region comprises a residue corresponding to residue 239 of SEQ ID NO: 7. In some embodiments, the HVR2 region comprises a residue corresponding to residue 262 of SEQ ID NO: 7. In some embodiments, the HVR2 region comprises a residue corresponding to residue 263 of SEQ ID NO: 7. In some embodiments, the HVR2 region comprises a residue corresponding to residue 264 of SEQ ID NO: 7. In some embodiments, the HVR2 region comprises residues 215-270 of SEQ ID NO: 7 with up to 1, 2, 3, 4, 5, 6, 7, 8, 9, 10, or 11 amino acid substitutions. In some embodiments, the HVR2 region comprises residues 215-270 of SEQ ID NO: 7.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 7. In some embodiments, the second subunit comprises G, S, or A at a residue corresponding to residue 210 of SEQ ID NO: 7. In some embodiments, the second subunit comprises E, Q, or K at a residue corresponding to residue 271 of SEQ ID NO: 7. In some embodiments, the second subunit comprises a residue corresponding to residue 271 of SEQ ID NO: 7. In some embodiments, the second subunit comprises a residue corresponding to residue 330 of SEQ ID NO: 7. In some embodiments, the second subunit comprises residues 198-344 of SEQ ID NO: 7 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 7.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 7. In some embodiments, the engineered meganuclease comprises an amino acid sequence of SEQ ID NO: 7. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 28. In some embodiments, the engineered meganuclease is encoded by a nucleic acid sequence set forth in SEQ ID NO: 28.

HAO 25-26x.268 (SEQ ID NO: 8)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 8. In some embodiments, the HVR1 region comprises one or more residues corresponding to residues 24, 26, 28, 30, 32, 33, 38, 40, 42, 44, 46, 68, 70, 75, and 77 of SEQ ID NO: 8. In some embodiments, the HVR1 region comprises residues corresponding to residues 24, 26, 28, 30, 32, 33, 38, 40, 42, 44, 46, 68, 70, 75, and 77 of SEQ ID NO: 8. In some embodiments, the HVR1 region comprises a residue corresponding to residue 43 of SEQ ID NO: 8. In some embodiments, the HVR1 region comprises Y, R, K, or D at a residue corresponding to residue 66 of SEQ ID NO: 8. In some embodiments, the HVR1 region comprises residues 24-79 of SEQ ID NO: 8 with up to 1, 2, 3, 4, 5, 6, 7, 8, 9, 10, or 11 amino acid substitutions. In some embodiments, the HVR1 region comprises residues 24-79 of SEQ ID NO: 8.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 8. In some embodiments, the first subunit comprises G, S, or A at a residue corresponding to residue 19 of SEQ ID NO: 8. In some embodiments, the first subunit comprises a residue corresponding to residue 19 of SEQ ID NO: 8. In some embodiments, the first subunit comprises E, Q, or K at a residue corresponding to residue 80 of SEQ ID NO: 8. In some embodiments, the first subunit comprises a residue corresponding to residue 80 of SEQ ID NO: 8. In some embodiments, the first subunit comprises residues 7-153 of SEQ ID NO: 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 8.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 8. In some embodiments, the HVR2 region comprises one or more residues corresponding to residues 215, 217, 219, 221, 223, 224, 229, 231, 233, 235, 237, 259, 261, 266, and 268 of SEQ ID NO: 8. In some embodiments, the HVR2 region comprises residues corresponding to residues 215, 217, 219, 221, 223, 224, 229, 231, 233, 235, 237, 259, 261, 266, and 268 of SEQ ID NO: 8. In some embodiments, the HVR2 region comprises Y, R, K, or D at a residue corresponding to residue 257 of SEQ ID NO: 8. In some embodiments, the HVR2 region comprises a residue corresponding to residue 239 of SEQ ID NO: 8. In some embodiments, the HVR2 region comprises a residue corresponding to residue 262 of SEQ ID NO: 8. In some embodiments, the HVR2 region comprises a residue corresponding to residue 263 of SEQ ID NO: 8. In some embodiments, the HVR2 region comprises a residue corresponding to residue 264 of SEQ ID NO: 8. In some embodiments, the HVR2 region comprises residues 215-270 of SEQ ID NO: 8 with up to 1, 2, 3, 4, 5, 6, 7, 8, 9, 10, or 11 amino acid substitutions. In some embodiments, the HVR2 region comprises residues 215-270 of SEQ ID NO: 8.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 8. In some embodiments, the second subunit comprises G, S, or A at a residue corresponding to residue 210 of SEQ ID NO: 8. In some embodiments, the second subunit comprises E, Q, or K at a residue corresponding to residue 271 of SEQ ID NO: 8. In some embodiments, the second subunit comprises residues 198-344 of SEQ ID NO: 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 8.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 8. In some embodiments, the engineered meganuclease comprises an amino acid sequence of SEQ ID NO: 8. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 29. In some embodiments, the engineered meganuclease is encoded by a nucleic acid sequence set forth in SEQ ID NO: 29.

HAO 25-26x.227 (SEQ ID NO: 9)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 9. In some embodiments, the HVR1 region comprises one or more residues corresponding to residues 24, 26, 28, 30, 32, 33, 38, 40, 42, 44, 46, 68, 70, 75, and 77 of SEQ ID NO: 9. In some embodiments, the HVR1 region comprises residues corresponding to residues 24, 26, 28, 30, 32, 33, 38, 40, 42, 44, 46, 68, 70, 75, and 77 of SEQ ID NO: 9. In some embodiments, the HVR1 region comprises Y, R, K, or D at a residue corresponding to residue 66 of SEQ ID NO: 9. In some embodiments, the HVR1 region comprises residues 24-79 of SEQ ID NO: 9 with up to 1, 2, 3, 4, 5, 6, 7, 8, 9, 10, or 11 amino acid substitutions. In some embodiments, the HVR1 region comprises residues 24-79 of SEQ ID NO: 9.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 9. In some embodiments, the first subunit comprises G, S, or A at a residue corresponding to residue 19 of SEQ ID NO: 9. In some embodiments, the first subunit comprises a residue corresponding to residue 19 of SEQ ID NO: 9. In some embodiments, the first subunit comprises E, Q, or K at a residue corresponding to residue 80 of SEQ ID NO: 9. In some embodiments, the first subunit comprises a residue corresponding to residue 80 of SEQ ID NO: 9. In some embodiments, the first subunit comprises residues 7-153 of SEQ ID NO: 9 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 9.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 9. In some embodiments, the HVR2 region comprises one or more residues corresponding to residues 215, 217, 219, 221, 223, 224, 229, 231, 233, 235, 237, 259, 261, 266, and 268 of SEQ ID NO: 9. In some embodiments, the HVR2 region comprises residues corresponding to residues 215, 217, 219, 221, 223, 224, 229, 231, 233, 235, 237, 259, 261, 266, and 268 of SEQ ID NO: 9. In some embodiments, the HVR2 region comprises Y, R, K, or D at a residue corresponding to residue 257 of SEQ ID NO: 9. In some embodiments, the HVR2 region comprises a residue corresponding to residue 239 of SEQ ID NO: 9. In some embodiments, the HVR2 region comprises a residue corresponding to residue 241 of SEQ ID NO: 9. In some embodiments, the HVR2 region comprises a residue corresponding to residue 263 of SEQ ID NO: 9. In some embodiments, the HVR2 region comprises a residue corresponding to residue 264 of SEQ ID NO: 9. In some embodiments, the HVR2 region comprises a residue corresponding to residue 265 of SEQ ID NO: 9. In some embodiments, the HVR2 region comprises residues 215-270 of SEQ ID NO: 9 with up to 1, 2, 3, 4, 5, 6, 7, 8, 9, 10, or 11 amino acid substitutions. In some embodiments, the HVR2 region comprises residues 215-270 of SEQ ID NO: 9.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 9. In some embodiments, the second subunit comprises G, S, or A at a residue corresponding to residue 210 of SEQ ID NO: 9. In some embodiments, the second subunit comprises E, Q, or K at a residue corresponding to residue 271 of SEQ ID NO: 9. In some embodiments, the second subunit comprises a residue corresponding to residue 271 of SEQ ID NO: 9. In some embodiments, the second subunit comprises a residue corresponding to residue 330 of SEQ ID NO: 9. In some embodiments, the second subunit comprises residues 198-344 of SEQ ID NO: 9 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 9.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 9. In some embodiments, the engineered meganuclease comprises an amino acid sequence of SEQ ID NO: 9. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 30. In some embodiments, the engineered meganuclease is encoded by a nucleic acid sequence set forth in SEQ ID NO: 30.

HAO 25-26L.1128 (SEQ ID NO: 10)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 10. In some embodiments, the HVR1 region comprises one or more residues corresponding to residues 24, 26, 28, 30, 32, 33, 38, 40, 42, 44, 46, 68, 70, 75, and 77 of SEQ ID NO: 10. In some embodiments, the HVR1 region comprises residues corresponding to residues 24, 26, 28, 30, 32, 33, 38, 40, 42, 44, 46, 68, 70, 75, and 77 of SEQ ID NO: 10. In some embodiments, the HVR1 region comprises a residue corresponding to residue 43 of SEQ ID NO: 10. In some embodiments, the HVR1 region comprises Y, R, K, or D at a residue corresponding to residue 66 of SEQ ID NO: 10. In some embodiments, the HVR1 region comprises residues 24-79 of SEQ ID NO: 10 with up to 1, 2, 3, 4, 5, 6, 7, 8, 9, 10, or 11 amino acid substitutions. In some embodiments, the HVR1 region comprises residues 24-79 of SEQ ID NO: 10.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 10. In some embodiments, the first subunit comprises G, S, or A at a residue corresponding to residue 19 of SEQ ID NO: 10. In some embodiments, the first subunit comprises a residue corresponding to residue 19 of SEQ ID NO: 10. In some embodiments, the first subunit comprises E, Q, or K at a residue corresponding to residue 80 of SEQ ID NO: 10. In some embodiments, the first subunit comprises residues 7-153 of SEQ ID NO: 10 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 10.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 10. In some embodiments, the HVR2 region comprises one or more residues corresponding to residues 215, 217, 219, 221, 223, 224, 229, 231, 233, 235, 237, 259, 261, 266, and 268 of SEQ ID NO: 10. In some embodiments, the HVR2 region comprises residues corresponding to residues 215, 217, 219, 221, 223, 224, 229, 231, 233, 235, 237, 259, 261, 266, and 268 of SEQ ID NO: 10. In some embodiments, the HVR2 region comprises Y, R, K, or D at a residue corresponding to residue 257 of SEQ ID NO: 10. In some embodiments, the HVR2 region comprises a residue corresponding to residue 239 of SEQ ID NO: 10. In some embodiments, the HVR2 region comprises a residue corresponding to residue 262 of SEQ ID NO: 10. In some embodiments, the HVR2 region comprises a residue corresponding to residue 263 of SEQ ID NO: 10. In some embodiments, the HVR2 region comprises a residue corresponding to residue 264 of SEQ ID NO: 10. In some embodiments, the HVR2 region comprises residues 215-270 of SEQ ID NO: 10 with up to 1, 2, 3, 4, 5, 6, 7, 8, 9, 10, or 11 amino acid substitutions. In some embodiments, the HVR2 region comprises residues 215-270 of SEQ ID NO: 10.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 10. In some embodiments, the second subunit comprises G, S, or A at a residue corresponding to residue 210 of SEQ ID NO: 10. In some embodiments, the second subunit comprises E, Q, or K at a residue corresponding to residue 271 of SEQ ID NO: 10. In some embodiments, the second subunit comprises a residue corresponding to residue 271 of SEQ ID NO: 10. In some embodiments, the second subunit comprises residues 198-344 of SEQ ID NO: 10 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 10.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 10. In some embodiments, the engineered meganuclease comprises an amino acid sequence of SEQ ID NO: 10. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 31. In some embodiments, the engineered meganuclease is encoded by a nucleic acid sequence set forth in SEQ ID NO: 31. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 33. In some embodiments, the engineered meganuclease is encoded by a nucleic acid sequence set forth in SEQ ID NO: 33.

HAO 25-26L.1434 (SEQ ID NO: 11)

In some embodiments, the HVR1 region comprises an amino acid sequence having at least 80%, 85%, 90%, 91%, 92%, 93%, 94%, 95%, 96%, 97%, 98%, 99% or more sequence identity to an amino acid sequence corresponding to residues 24-79 of SEQ ID NO: 11. In some embodiments, the HVR1 region comprises one or more residues corresponding to residues 24, 26, 28, 30, 32, 33, 38, 40, 42, 44, 46, 68, 70, 75, and 77 of SEQ ID NO: 11. In some embodiments, the HVR1 region comprises residues corresponding to residues 24, 26, 28, 30, 32, 33, 38, 40, 42, 44, 46, 68, 70, 75, and 77 of SEQ ID NO: 11. In some embodiments, the HVR1 region comprises a residue corresponding to residue 43 of SEQ ID NO: 11. In some embodiments, the HVR1 region comprises Y, R, K, or D at a residue corresponding to residue 66 of SEQ ID NO: 11. In some embodiments, the HVR1 region comprises residues 24-79 of SEQ ID NO: 11 with up to 1, 2, 3, 4, 5, 6, 7, 8, 9, 10, or 11 amino acid substitutions. In some embodiments, the HVR1 region comprises residues 24-79 of SEQ ID NO: 11.

In some embodiments, the first subunit comprises an amino acid sequence having at least 80%, 85%, 90%, 91%, 92%, 93%, 94%, 95%, 96%, 97%, 98%, 99% or more sequence identity to residues 7-153 of SEQ ID NO: 11. In some embodiments, the first subunit comprises G, S, or A at a residue corresponding to residue 19 of SEQ ID NO: 11. In some embodiments, the first subunit comprises a residue corresponding to residue 19 of SEQ ID NO: 11. In some embodiments, the first subunit comprises E, Q, or K at a residue corresponding to residue 80 of SEQ ID NO: 11. In some embodiments, the first subunit comprises residues 7-153 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the first subunit comprises residues 7-153 of SEQ ID NO: 11.

In some embodiments, the HVR2 region comprises an amino acid sequence having at least 80%, 85%, 90%, 91%, 92%, 93%, 94%, 95%, 96%, 97%, 98%, 99% or more sequence identity to an amino acid sequence corresponding to residues 215-270 of SEQ ID NO: 11. In some embodiments, the HVR2 region comprises one or more residues corresponding to residues 215, 217, 219, 221, 223, 224, 229, 231, 233, 235, 237, 259, 261, 266, and 268 of SEQ ID NO: 11. In some embodiments, the HVR2 region comprises residues corresponding to residues 215, 217, 219, 221, 223, 224, 229, 231, 233, 235, 237, 259, 261, 266, and 268 of SEQ ID NO: 11. In some embodiments, the HVR2 region comprises Y, R, K, or D at a residue corresponding to residue 257 of SEQ ID NO: 11. In some embodiments, the HVR2 region comprises a residue corresponding to residue 239 of SEQ ID NO: 11. In some embodiments, the HVR2 region comprises a residue corresponding to residue 262 of SEQ ID NO: 11. In some embodiments, the HVR2 region comprises a residue corresponding to residue 263 of SEQ ID NO: 11. In some embodiments, the HVR2 region comprises a residue corresponding to residue 264 of SEQ ID NO: 11. In some embodiments, the HVR2 region comprises residues 215-270 of SEQ ID NO: 11 with up to 1, 2, 3, 4, 5, 6, 7, 8, 9, 10, or 11 amino acid substitutions. In some embodiments, the HVR2 region comprises residues 215-270 of SEQ ID NO: 11.

In some embodiments, the second subunit comprises an amino acid sequence having at least 80%, 85%, 90%, 91%, 92%, 93%, 94%, 95%, 96%, 97%, 98%, 99% or more sequence identity to residues 198-344 of SEQ ID NO: 11. In some embodiments, the second subunit comprises G, S, or A at a residue corresponding to residue 210 of SEQ ID NO: 11. In some embodiments, the second subunit comprises E, Q, or K at a residue corresponding to residue 271 of SEQ ID NO: 11. In some embodiments, the second subunit comprises a residue corresponding to residue 271 of SEQ ID NO: 11. In some embodiments, the second subunit comprises residues 198-344 of SEQ ID NO: 11 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions. In some embodiments, the second subunit comprises residues 198-344 of SEQ ID NO: 11.

In some embodiments, the engineered meganuclease is a single-chain meganuclease comprising a linker, wherein the linker covalently joins said first subunit and said second subunit. In some embodiments, the engineered meganuclease comprises an amino acid sequence having at least 80%, 85%, 90%, 91%, 92%, 93%, 94%, 95%, 96%, 97%, 98%, 99% or more sequence identity SEQ ID NO: 11. In some embodiments, the engineered meganuclease comprises an amino acid sequence of SEQ ID NO: 11. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 32. In some embodiments, the engineered meganuclease is encoded by a nucleic acid sequence set forth in SEQ ID NO: 32. In some embodiments, the engineered meganuclease is encoded by a nucleic sequence having at least 80%, 85%, 90%, 91%, 92%, 93%, 94%, 95%, 96%, 97%, 98%, 99% or more sequence identity to a nucleic acid sequence set forth in SEQ ID NO: 34. In some embodiments, the engineered meganuclease is encoded by a nucleic acid sequence set forth in SEQ ID NO: 34.

In some embodiments, the modified HAO1 gene comprises an insertion or deletion in exon 2, which results in a non-functional HAO1 protein. Accordingly, the insertions and deletions caused by the meganucleases described herein often result in a frameshift or introduction of a stop codon, which results in a truncated protein that is not functional.

In some embodiments, the presently disclosed engineered meganucleases exhibit at least one optimized characteristic in comparison to previously described meganucleases. Such optimized characteristics include improved (i.e. increased) specificity resulting in reduced off-target cutting, and enhanced (i.e., increased) efficiency of cleavage and indel (i.e., insertion or deletion) formation at a recognition sequence in the HAO1 gene. Thus, in particular embodiments, the presently disclosed engineered meganucleases, when delivered to a population of cells, is able to generate a greater percentage of cells with a cleavage and/or an indel in the HAO1 gene. In some of these embodiments, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99% or 100% of cells are target cells that comprise a cleavage and/or an indel in the HAO1 gene. Cleavage and/or indel formation by a meganuclease can be measured using any method known in the art, including T7E assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety).

In some embodiments, the target cell is a hepatocyte. In some embodiments, the target cell is a primary human hepatocyte (PHH). In some embodiments, the target cell is a non-human, mammalian hepatocyte.

2.3 Methods for Delivering and Expressing Engineered Meganucleases

In different aspects, the invention provides engineered meganucleases described herein that are useful for binding and cleaving recognition sequences within a HAO1 gene of a cell (e.g., the human HAO1 gene). The invention provides various methods for modifying a HAO1 gene in cells using engineered meganucleases described herein, methods for making genetically-modified cells comprising a modified dystrophin gene, and methods of modifying a dystrophin gene in a target cell in a subject. In further aspects, the invention provides methods for treating PH1 in a subject by administering the engineered meganucleases described herein, or polynucleotides encoding the same, to a subject, in some cases as part of a pharmaceutical composition.

In each case, it is envisioned that the engineered meganucleases, or polynucleotides encoding the same, are introduced into cells, such as liver cells or liver precursor cells that express an HAO1 protein. Engineered meganucleases described herein can be delivered into a cell in the form of protein or, preferably, as a polynucleotide encoding the engineered meganuclease. Such polynucleotides can be, for example, DNA (e.g., circular or linearized plasmid DNA, PCR products, or a viral genome) or RNA (e.g., mRNA).

The invention provides methods for producing genetically-modified cells using engineered meganucleases that bind and cleave recognition sequences found within an HAO1 gene (e.g., the human HAO1 gene). Cleavage at such recognition sequences can allow for NHEJ at the cleavage site or insertion of an exogenous sequence via homologous recombination, thereby disrupting expression of the HAO1 protein. Disruption of the HAO1 protein expression may be determined by measuring the amount of HAO1 protein produced in the genetically-modified cell by, for example, well known protein measurement techniques known in the art including immunofluorescence, western blotting, and enzyme-linked immunosorbent assays (ELISA).

In some embodiments, disruption of the HAO1 protein can reduce the conversion of glycolate to glyoxylate. The conversion of glycolate to glyoxylate can be determined by measurements of glycolate and/or glyoxylate levels in the genetically-modified eukaryotic cell relative to a control (e.g., a control cell). For example, the control may be a eukaryotic cell treated with a meganuclease that does not target the HAO1 gene. In specific embodiments, the conversion of glycolate to glyoxylate can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the control. In some embodiments, the conversion of glycolate to glyoxylate can be reduced by 1%-5%, 5%-10%, 10%-20%, 20%-30%, 30%-40%, 40%-50%, 50%-60%, 70%-80%, 90%-95%, 95%-98%, or up 100% relative to the control.

Oxalate levels can be reduced in a genetically-modified eukaryotic cell relative to a control (e.g., a control cell). For example, the control may be a eukaryotic cell treated with a meganuclease that does not target the HAO1 gene. In some embodiments, the production of oxalate, or oxalate level, can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the control. In some embodiments, the production of oxalate can be reduced by 1%-5%, 5%-10%, 10%-20%, 20%-30%, 30%-40%, 40%-50%, 50%-60%, 70%-80%, 90%-95%, 95%-98%, or up to 100% relative to the control. Oxalate levels can be measured in a cell, tissue, organ, blood, or urine, as described elsewhere herein.

In some embodiments, the methods disclosed herein are effective to increase a glycolate/creatinine ratio relative to a reference level. For example, methods disclosed herein can increase the glycolate/creatinine ratio in a urine sample from the subject and/or decrease an oxalate/creatinine ratio in a urine sample from the subject relative to a reference level. In specific embodiments of the method, the reference level is the oxalate/creatinine ratio and/or glycolate/creatinine ratio in a urine sample in a control subject having PH1. The control subject may be a subject having PH1 treated with a meganuclease that does not target the HAO1 gene.

In some embodiments, the oxalate/creatinine ratio can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the reference level. In some embodiments, the oxalate/creatinine ratio can be reduced by 1%-5%, 5%-10%, 10%-20%, 20%-30%, 30%-40%, 40%-50%, 50%-60%, 70%-80%, 90%-95%, 95%-98%, or up to 100% relative to the reference level.

In some embodiments, the glycolate/creatinine ratio can be increased by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or at least about 100% relative to the reference level. In some embodiments, the glycolate/creatinine ratio can be increased by at least about 2×-fold, at least about 3×-fold, at least about 4×-fold, at least about 5×-fold, at least about 6×-fold, at least about 7×-fold, at least about 8×-fold, at least about 9×-fold, or at least about 10×-fold relative to the reference level.

The methods disclosed herein can be used to decrease the level of calcium precipitates in a kidney of the subject relative to a reference level. The reference level can be the level of calcium precipitates in the kidney of a control subject having PH1. For example, the control subject may be a subject having PH1 treated with a meganuclease that does not target the HAO1 gene.

In particular embodiments, the level of calcium precipitates can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or up to 100% relative to the reference level. In some embodiments, the level of calcium precipitates can be reduced by 1%-5%, 5%-10%, 10%-20%, 20%-30%, 30%-40%, 40%-50%, 50%-60%, 70%-80%, 90%-95%, 95%-98%, or up to 100% relative to the reference level.

The methods disclosed herein can be effective to decrease the risk of renal failure in the subject relative to a control subject having PH1. The control subject may be a subject having PH1 treated with a meganuclease that does not target the HAO1 gene.

In some embodiments, the risk of renal failure can be reduced by at least about 1%, at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, or 100% relative to the reference level. In some embodiments, the risk of renal failure can be reduced by 1%-5%, 5%-10%, 10%-20%, 20%-30%, 30%-40%, 40%-50%, 50%-60%, 70%-80%, 90%-95%, 95%-98%, or up to 100% relative to the reference level.

The invention further provides methods for treating PH1 in a subject by administering a pharmaceutical composition comprising a pharmaceutically acceptable carrier and an engineered meganuclease of the invention, or a nucleic acid encoding the engineered meganuclease. In each case, the invention includes that an engineered meganuclease of the invention can be delivered to and/or expressed from DNA/RNA in cells in vivo that would typically express HAO1 (e.g., cells in the liver (i.e., hepatocytes) or cells in the pancreas).

Detection and Expression

Expression of a modified HAO1 protein (i.e., a truncated, non-functional HAO1 protein) in a genetically-modified cell or subject can be detected using standard methods in the art. For example, levels of such modified HAO1 may be assessed based on the level of any variable associated with HAO1 gene expression, e.g., HAO1 mRNA levels or HAO1 protein levels. Increased levels or expression of such modified or truncated HAO1 may be assessed by an increase in an absolute or relative level of one or more of these variables compared with a reference level. Such modified HAO1 levels may be measured in a biological sample isolated from a subject, such as a tissue biopsy or a bodily fluid including blood, serum, plasma, cerebrospinal fluid, or urine. Optionally, such modified HAO1 levels are normalized to a standard protein or substance in the sample. Further, such modified HAO1 levels can be assessed any time before, during, or after treatment in accordance with the methods herein.

In various aspects, the methods described herein can increase protein levels of a modified HAO1 in a genetically-modified cell, target cell, or subject (e.g., as measured in a cell, a tissue, an organ, or a biological sample obtained from the subject), to at least 1%, 2%, 3%, 4%, 5%, 10%, 15%, 20%, 25%, 30%, 40%, 50%, 60%, 70%, 80%, 90%, 95%, 100%, or more, of a reference level (i.e., expression level of HAO1 in a wild-type cell or subject). In some embodiments, the methods herein are effective to increase the level of such modified HAO1 protein to about 10% to about 100% (e.g., 10%-20%, 20%-30%, 30%-40%, 40%-50%, 50%-60%, 60%-70%, 70%-80%, 80%-90%, 90%-100%, or more) of a reference level of HAO1 (i.e., expression level of HAO1 in a wild-type cell or subject).

Introduction of Engineered Meganucleases into Cells

Engineered meganuclease proteins disclosed herein, or polynucleotides encoding the same, can be delivered into cells to cleave genomic DNA by a variety of different mechanisms known in the art, including those further detailed herein below.

Engineered meganucleases disclosed herein can be delivered into a cell in the form of protein or, preferably, as a polynucleotide comprising a nucleic acid sequence encoding the engineered meganuclease. Such polynucleotides can be, for example, DNA (e.g., circular or linearized plasmid DNA, PCR products, or viral genomes) or RNA (e.g., mRNA).

For embodiments in which the engineered meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), *Proc Natl Acad Sci USA.* 81(3):659-63) or the SV40 early promoter (Benoist and Chambon (1981), Nature. 290 (5804):304-10) as well as inducible promoters such as the tetracycline-inducible promoter (Dingermann et al. (1992), *Mol Cell Biol.* 12(9):4038-45). An engineered meganuclease of the invention can also be operably linked to a synthetic promoter. Synthetic promoters can include, without limitation, the JeT promoter (WO 2002/012514).

In specific embodiments, a nucleic acid sequence encoding an engineered nuclease of the invention is operably linked to a tissue-specific promoter, such as a liver-specific promoter. Examples of liver-specific promoters include, without limitation, human alpha-1 antitrypsin promoter, hybrid liver-specific promoter (hepatic locus control region from ApoE gene (ApoE-HCR) and a liver-specific alpha1-antitrypsin promoter), human thyroxine binding globulin (TBG) promoter, and apolipoprotein A-II promoter.

In some embodiments, wherein a single polynucleotide comprises two separate nucleic acid sequences each encoding an engineered meganuclease described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymczak and Vignali (2005) *Expert Opin Biol Ther.* 5:627-38). Such 2A peptide sequences can include, for example, a T2A, P2A, E2A, or F2A sequence.

In specific embodiments, a polynucleotide comprising a nucleic acid sequence encoding an engineered meganuclease described herein is delivered on a recombinant DNA construct or expression cassette. For example, the recombinant DNA construct can comprise an expression cassette (i.e., "cassette") comprising a promoter and a nucleic acid sequence encoding an engineered meganuclease described herein.

In another particular embodiment, a polynucleotide comprising a nucleic acid sequence encoding an engineered meganuclease described herein is introduced into the cell using a single-stranded DNA template. The single-stranded DNA can further comprise a 5' and/or a 3' AAV inverted terminal repeat (ITR) upstream and/or downstream of the sequence encoding the engineered nuclease. The single-stranded DNA can further comprise a 5' and/or a 3' homology arm upstream and/or downstream of the sequence encoding the engineered meganuclease.

In another particular embodiment, a polynucleotide comprising a nucleic acid sequence encoding an engineered meganuclease described herein can be introduced into a cell using a linearized DNA template. Such linearized DNA templates can be produced by methods known in the art. For example, a plasmid DNA encoding a nuclease can be digested by one or more restriction enzymes such that the circular plasmid DNA is linearized prior to being introduced into a cell.

In some embodiments, mRNA encoding an engineered meganuclease described herein is delivered to a cell because this reduces the likelihood that the gene encoding the engineered meganuclease will integrate into the genome of the cell. Such mRNA can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, CA), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In some embodiments, the meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn, et al. (2008) *Mol Ther.* 16:1624-9), TAT peptide from the HIV virus (Hudecz et al. (2005), *Med. Res. Rev.* 25: 679-736), MPG (Simeoni, et al. (2003) *Nucleic Acids Res.* 31:2717-2724), Pep-1 (Deshayes et al. (2004) *Biochemistry*

43: 7698-7706, and HSV-1 VP-22 (Deshayes et al. (2005) *Cell Mol Life Sci.* 62:1839-49. In an alternative embodiment, engineered nucleases, or DNA/mRNA encoding nucleases, are coupled covalently or non-covalently to an antibody that recognizes a specific cell-surface receptor expressed on target cells such that the nuclease protein/DNA/mRNA binds to and is internalized by the target cells. Alternatively, engineered nuclease protein/DNA/mRNA can be coupled covalently or non-covalently to the natural ligand (or a portion of the natural ligand) for such a cell-surface receptor. (McCall, et al. (2014) *Tissue Barriers.* 2(4): e944449; Dinda, et al. (2013) *Curr Pharm Biotechnol.* 14:1264-74; Kang, et al. (2014) *Curr Pharm Biotechnol.* 15(3):220-30; Qian et al. (2014) *Expert Opin Drug Metab Toxicol.* 10(11):1491-508).

In some embodiments, meganuclease proteins, or DNA/mRNA encoding meganucleases, are encapsulated within biodegradable hydrogels for injection or implantation within the desired region of the liver (e.g., in proximity to hepatic sinusoidal endothelial cells or hematopoietic endothelial cells, or progenitor cells which differentiate into the same). Hydrogels can provide sustained and tunable release of the therapeutic payload to the desired region of the target tissue without the need for frequent injections, and stimuli-responsive materials (e.g., temperature- and pH-responsive hydrogels) can be designed to release the payload in response to environmental or externally applied cues (Kang Derwent et al. (2008) Trans Am Ophthalmol Soc. 106:206-214).

In some embodiments, meganuclease proteins, or DNA/mRNA encoding meganucleases, are coupled covalently or, preferably, non-covalently to a nanoparticle or encapsulated within such a nanoparticle using methods known in the art (Sharma, et al. (2014) *Biomed Res Int.* 2014). A nanoparticle is a nanoscale delivery system whose length scale is <1 μm, preferably <100 nm. Such nanoparticles may be designed using a core composed of metal, lipid, polymer, or biological macromolecule, and multiple copies of the meganuclease proteins, mRNA, or DNA can be attached to or encapsulated with the nanoparticle core. This increases the copy number of the protein/mRNA/DNA that is delivered to each cell and, so, increases the intracellular expression of each meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) *Biomaterials.* 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell-surface receptors and the natural ligands (or portions of the natural ligands) for cell surface receptors.

In some embodiments, the meganuclease proteins, or DNA/mRNA encoding meganucleases, are encapsulated within liposomes or complexed using cationic lipids (see, e.g., LIPOFECTAMINE™, Life Technologies Corp., Carlsbad, CA; Zuris et al. (2015) Nat Biotechnol. 33: 73-80; Mishra et al. (2011) J Drug Deliv. 2011:863734). In some embodiments, the meganuclease proteins, or DNA/mRNA encoding meganucleases, are encapsulated within Lipofectamine® MessengerMax cationic lipid. The liposome and lipoplex formulations can protect the payload from degradation, enhance accumulation and retention at the target site, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) *Ther Deliv.* 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding meganucleases, are combined with amphiphilic molecules that self-assemble into micelles (Tong et al. (2007) *J Gene Med.* 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in U.S. Pat. Nos. 6,015,832, 6,506,803, 6,635,676, 6,559,189, and 7,767,216, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) *Nanoscale.* 7(9): 3845-56; Cheng et al. (2008) *J Pharm Sci.* 97(1): 123-43). The dendrimer generation can control the payload capacity and size and can provide a high payload capacity. Moreover, display of multiple surface groups can be leveraged to improve stability, reduce nonspecific interactions, and enhance cell-specific targeting and drug release.

In some embodiments, polynucleotides comprising a nucleic acid sequence encoding an engineered meganuclease described herein are introduced into a cell using a recombinant virus (i.e., a recombinant viral vector). Such recombinant viruses are known in the art and include recombinant retroviruses, recombinant lentiviruses, recombinant adenoviruses, and recombinant adeno-associated viruses (AAVs) (reviewed in Vannucci, et al. (2013 *New Microbiol.* 36:1-22). Recombinant AAVs useful in the invention can have any serotype that allows for transduction of the virus into a target cell type and expression of the meganuclease gene in the target cell. For example, in some embodiments, recombinant AAVs have a serotype (i.e., a capsid) of AAV1, AAV2, AAV5 AAV6, AAV7, AAV8, AAV9, or AAV12. It is known in the art that different AAVs tend to localize to different tissues (Wang et al., *Expert Opin Drug Deliv* 11(3). 2014). Accordingly, in some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. AAVs can also be self-complementary such that they do not require second-strand DNA synthesis in the host cell (McCarty, et al. (2001) Gene Ther. 8:1248-54). Polynucleotides delivered by recombinant AAVs can include left (5') and right (3') inverted terminal repeats as part of the viral genome. In some embodiments, the recombinant viruses are injected directly into target tissues. In alternative embodiments, the recombinant viruses are delivered systemically via the circulatory system.

In some embodiments, the AAV8 capsid is used in combination with the TBG liver-specific promoter. The AAV8 serotype exhibits preferential tropism for liver tissues, and the specificity of the liver TBG promoter limits editing to non-liver tissues.

In one embodiment, a recombinant virus used for meganuclease gene delivery is a self-limiting recombinant virus. A self-limiting virus can have limited persistence time in a cell or organism due to the presence of a recognition sequence for an engineered meganuclease within the viral genome. Thus, a self-limiting recombinant virus can be engineered to provide a coding sequence for a promoter, an engineered meganuclease described herein, and a meganuclease recognition site within the ITRs. The self-limiting recombinant virus delivers the meganuclease gene to a cell, tissue, or organism, such that the meganuclease is expressed and able to cut the genome of the cell at an endogenous recognition sequence within the genome. The delivered meganuclease will also find its target site within the self-limiting recombinant viral genome, and cut the recombinant viral genome at this target site. Once cut, the 5' and 3' ends of the viral genome will be exposed and degraded by exonucleases, thus killing the virus and ceasing production of the meganuclease.

If a polynucleotide comprising a nucleic acid sequence encoding an engineered meganuclease described herein is delivered to a cell by a recombinant virus (e.g. an AAV), the nucleic acid sequence encoding the engineered meganuclease can be operably linked to a promoter. In some embodiments, this can be a viral promoter such as endogenous promoters from the recombinant virus (e.g. the LTR of a lentivirus) or the well-known cytomegalovirus- or SV40 virus-early promoters. In particular embodiments, nucleic acid sequences encoding the engineered meganucleases are operably linked to a promoter that drives gene expression preferentially in the target cells (e.g., liver cells). Examples of liver-specific tissue promoters include but are not limited to those liver-specific promoters previously described, including TBG.

In some embodiments, wherein a single polynucleotide comprises two separate nucleic acid sequences each encoding an engineered meganuclease described herein, the meganuclease genes are operably linked to two separate promoters. In alternative embodiments, the two meganuclease genes are operably linked to a single promoter, and in some examples can be separated by an internal-ribosome entry site (IRES) or a 2A peptide sequence (Szymczak and Vignali (2005) *Expert Opin Biol Ther.* 5:627-38). Such 2A peptide sequences can include, for example, a T2A, P2A, E2A, or F2A sequence.

In some embodiments, the methods include delivering an engineered meganuclease described herein, or a polynucleotide encoding the same, to a cell in combination with a second polynucleotide comprising an exogenous nucleic acid sequence encoding a sequence of interest, wherein the engineered meganuclease is expressed in the cells, recognizes and cleaves a recognition sequence described herein (e.g., SEQ ID NO: 3) within a HAO1 gene of the cell, and generates a cleavage site, wherein the exogenous nucleic acid and sequence of interest are inserted into the genome at the cleavage site (e.g., by homologous recombination). In some such examples, the polynucleotide can comprise sequences homologous to nucleic acid sequences flanking the meganuclease cleavage site in order to promote homologous recombination of the exogenous nucleic acid and sequence of interest into the genome.

Such polynucleotides comprising exogenous nucleic acids can be introduced into a cell and/or delivered to a target cell in a subject by any of the means previously discussed. In particular embodiments, such polynucleotides comprising exogenous nucleic acid molecules are introduced by way of a recombinant virus (i.e., a viral vector), such as a recombinant lentivirus, recombinant retrovirus, recombinant adenovirus, or a recombinant AAV. Recombinant AAVs useful for introducing a polynucleotide comprising an exogenous nucleic acid molecule can have any serotype (i.e., capsid) that allows for transduction of the virus into the cell and insertion of the exogenous nucleic acid molecule sequence into the cell genome. In some embodiments, recombinant AAVs have a serotype of AAV1, AAV2, AAV5 AAV6, AAV7, AAV8, AAV9, or AAV12. In some embodiments, the AAV serotype is AAV1. In some embodiments, the AAV serotype is AAV2. In some embodiments, the AAV serotype is AAV5. In some embodiments, the AAV serotype is AAV6. In some embodiments, the AAV serotype is AAV7. In some embodiments, the AAV serotype is AAV8. In some embodiments, the AAV serotype is AAV9. In some embodiments, the AAV serotype is AAV12. The recombinant AAV can also be self-complementary such that it does not require second-strand DNA synthesis in the host cell. Exogenous nucleic acid molecules introduced using a recombinant AAV can be flanked by a 5' (left) and 3' (right) inverted terminal repeat in the viral genome.

In another particular embodiment, an exogenous nucleic acid molecule can be introduced into a cell using a single-stranded DNA template. The single-stranded DNA can comprise the exogenous nucleic acid molecule and, in particular embodiments, can comprise 5' and 3' homology arms to promote insertion of the nucleic acid sequence into the meganuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding a meganuclease of the invention and/or an exogenous nucleic acid sequence of the invention can be introduced into the cell by transfection with a linearized DNA template. In some examples, a plasmid DNA encoding an engineered meganuclease and/or an exogenous nucleic acid sequence can be digested by one or more restriction enzymes such that the circular plasmid DNA is linearized prior to transfection into the cell (e.g., a liver cell).

When delivered to a cell, an exogenous nucleic acid of the invention can be operably linked to any promoter suitable for expression of the encoded polypeptide in the cell, including those mammalian, inducible, and tissue-specific promoters previously discussed. An exogenous nucleic acid of the invention can also be operably linked to a synthetic promoter. Synthetic promoters can include, without limitation, the JeT promoter (WO 2002/012514). In specific embodiments, a nucleic acid sequence encoding an engineered meganuclease as disclosed herein can be operably linked to a liver-specific promoter discussed herein, such as a TBG promoter.

Administration

The target tissue(s) or target cell(s) include, without limitation, liver cells, such as human liver cells. In some embodiments, the target cell is a liver progenitor cell. Such liver progenitor cells have been described in the art and can either be present in a subject or derived from another stem cell population such as an induced pluripotent stem cell or an embryonic stem cell.

In some embodiments, engineered meganucleases described herein, or polynucleotides encoding the same, are delivered to a cell in vitro. In some embodiments, engineered meganucleases described herein, or polynucleotides encoding the same, are delivered to a cell in a subject in vivo. As discussed herein, meganucleases of the invention can be delivered as purified protein or as a polynucleotide (e.g., RNA or DNA) comprising a nucleic acid sequence encoding the meganuclease. In some embodiments, meganuclease proteins, or polynucleotides encoding meganucleases, are supplied to target cells (e.g., a liver cell or liver progenitor cell) via injection directly to the target tissue. Alternatively, meganuclease proteins, or polynucleotides encoding meganucleases, can be delivered systemically via the circulatory system.

In various embodiments of the methods, compositions described herein, such as the engineered meganucleases described herein, polynucleotides encoding the same, recombinant viruses comprising such polynucleotides, or lipid nanoparticles comprising such polynucleotides, can be administered via any suitable route of administration known in the art. Such routes of administration can include, for example, intravenous, intramuscular, intraperitoneal, subcutaneous, intrahepatic, transmucosal, transdermal, intraarterial, and sublingual. In some embodiments, the engineered meganuclease proteins, polynucleotides encoding the same, recombinant viruses comprising such polynucleotides, or lipid nanoparticles comprising such polynucleotides, are supplied to target cells (e.g., liver cells or liver precursor cells) via injection directly to the target tissue (e.g., liver tissue). Other suitable routes of administration can be readily determined by the treating physician as necessary.

In some embodiments, a therapeutically effective amount of an engineered nuclease described herein, or a polynucleotide encoding the same, is administered to a subject in need thereof for the treatment of a disease. As appropriate, the dosage or dosing frequency of the engineered meganuclease, or the polynucleotide encoding the same, may be adjusted over the course of the treatment, based on the judgment of the administering physician. Appropriate doses will depend, among other factors, on the specifics of any AAV chosen (e.g., serotype), any lipid nanoparticle chosen, on the route of administration, on the subject being treated (i.e., age, weight, sex, and general condition of the subject), and the mode of administration. Thus, the appropriate dosage may vary from patient to patient. An appropriate effective amount can be readily determined by one of skill in the art or treating physician. Dosage treatment may be a single dose schedule or, if multiple doses are required, a multiple dose schedule. Moreover, the subject may be administered as many doses as appropriate. One of skill in the art can readily determine an appropriate number of doses. The dosage may need to be adjusted to take into consideration an alternative route of administration or balance the therapeutic benefit against any side effects.

In some embodiments, the methods further include administration of a polynucleotide comprising a nucleic acid sequence encoding a secretion-impaired hepatotoxin, or encoding tPA, which stimulates hepatocyte regeneration without acting as a hepatotoxin.

In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg to about $1\times10^{14}$ gc/kg (e.g., about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg). In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg, about $1\times10^{11}$ gc/kg, about $1\times10^{12}$ gc/kg, about $1\times10^{13}$ gc/kg, or about $1\times10^{14}$ gc/kg. In some embodiments, a subject is administered a pharmaceutical composition comprising a polynucleotide comprising a nucleic acid sequence encoding an engineered meganuclease described herein, wherein the encoding nucleic acid sequence is administered at a dose of about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg. It should be understood that these doses can relate to the administration of a single polynucleotide comprising a single nucleic acid sequence encoding a single engineered meganuclease described herein or, alternatively, can relate to a single polynucleotide comprising a first nucleic acid sequence encoding a first engineered meganuclease described herein and a second nucleic acid sequence encoding a second engineered meganuclease described herein, wherein each of the two encoding nucleic acid sequences is administered at the indicated dose.

In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 3 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg, about 0.25 mg/kg, about 0.5 mg/kg, about 0.75 mg/kg, about 1.0 mg/kg, about 1.5 mg/kg, about 2.0 mg/kg, about 2.5 mg/kg, or about 3.0 mg/kg. In some embodiments, a subject is administered a lipid nanoparticle formulation comprising an mRNA comprising a nucleic acid sequence encoding an engineered meganuclease described herein, wherein the dose of the mRNA is about 0.1 mg/kg to about 0.25 mg/kg, about 0.25 mg/kg to about 0.5 mg/kg, about 0.5 mg/kg to about 0.75 mg/kg, about 0.75 mg/kg to about 1.0 mg/kg, about 1.0 mg/kg to about 1.5 mg/kg, about 1.5 mg/kg to about 2.0 mg/kg, about 2.0 mg/kg to about 2.5 mg/kg, or about 2.5 mg/kg to about 3.0 mg/kg.

2.4 Pharmaceutical Compositions

In some embodiments, the invention provides a pharmaceutical composition comprising a pharmaceutically acceptable carrier and an engineered meganuclease described herein, or a pharmaceutically acceptable carrier and a polynucleotide described herein that comprises a nucleic acid sequence encoding an engineered meganuclease described herein. Such polynucleotides can be, for example, mRNA or DNA as described herein. In some such examples, the polynucleotide in the pharmaceutical composition can be comprised by a lipid nanoparticle or can be comprised by a recombinant virus (e.g., a recombinant AAV). In other embodiments, the disclosure provides a pharmaceutical composition comprising a pharmaceutically acceptable carrier and a genetically-modified cell of the invention, which can be delivered to a target tissue where the cell expresses the engineered meganuclease as disclosed herein. Such pharmaceutical compositions are formulated, for example, for systemic administration, or administration to target tissues.

In some embodiments, the invention provides a pharmaceutical composition comprising a pharmaceutically acceptable carrier and engineered meganuclease of the invention, or a pharmaceutically acceptable carrier and an isolated polynucleotide comprising a nucleic acid encoding an engineered meganuclease of the invention. In other embodiments, the invention provides a pharmaceutical composition comprising a pharmaceutically acceptable carrier and a genetically-modified cell of the invention which can be delivered to a target tissue where the cell can then differentiate into a cell which expresses modified HAO1. In particular, pharmaceutical compositions are provided that comprise a pharmaceutically acceptable carrier and a therapeutically effective amount of a nucleic acid encoding an engineered meganuclease or an engineered meganuclease, wherein the engineered meganuclease has specificity for a recognition sequence within a HAO1 gene (e.g., HAO 25-26; SEQ ID NO: 3).

Pharmaceutical compositions of the invention can be useful for treating a subject having PH1. In some instances, the subject undergoing treatment in accordance with the methods and compositions provided herein can be characterized by a mutation in an AGXT gene. Other indications for treatment include, but are not limited to, the presence of one or more risk factors, including those discussed previously and in the following sections. A subject having PH1 or a subject who may be particularly receptive to treatment with the engineered meganucleases herein may be identified by ascertaining the presence or absence of one or more such risk factors, diagnostic, or prognostic indicators. The determination may be based on clinical and sonographic findings, including urine oxalate assessments, enzymology analyses, and/or DNA analyses known in the art (see, e.g., Example 3).

For example, the subject undergoing treatment can be characterized by urinary oxalate levels, e.g., urinary oxalate levels of at least 30 mg, 40 mg, 50 mg, 60 mg, 70 mg, 80 mg, 90 mg, 100 mg, 110 mg, 120 mg, 130 mg, 140 mg, 150 mg, 160 mg, 170 mg, 180 mg, 190 mg, 200 mg, 210 mg, 220 mg, 230 mg, 240 mg, 250 mg, 260 mg, 270 mg, 280 mg, 290 mg, 300 mg, 310 mg, 320 mg, 330 mg, 340 mg, 350 mg, 360 mg, 370 mg, 380 mg, 390 mg, or 400 mg of oxalate per 24 hour period, or more. In certain embodiments, the oxalate level is associated with one or more symptoms or pathologies. Oxalate levels may be measured in a biological sample, such as a body fluid including blood, serum, plasma, or urine. Optionally, oxalate is normalized to a standard protein or substance, such as creatinine in urine. In some embodiments, the claimed methods include administration of any of the engineered meganucleases described herein to reduce serum or urinary oxalate levels in a subject to undetectable levels, or to less than 1%2%, 5%, 10%, 20%, 30%, 40%, 50%, 60%, 70%, or 80% of the subject's oxalate levels prior to treatment, within 1 day, 3 days, 5 days, 7 days, 9 days, 12 days, or 15 days.

For example, hyperoxaluria in humans can be characterized by urinary oxalate excretion, e.g., excretion greater than about 40 mg (approximately 440 μmol) or greater than about 30 mg per day. Exemplary clinical cutoff levels for urinary oxalate are 43 mg/day (approximately 475 μmol) for men and 32 mg/day (approximately 350 μmol) for women, for example. Hyperoxaluria can also be defined as urinary oxalate excretion greater than 30 mg per day per gram of urinary creatinine. Persons with mild hyperoxaluria may excrete at least 30-60 (342-684 μmol) or 40-60 (456-684 μmol) mg of oxalate per day. Persons with enteric hyperoxaluria may excrete at least 80 mg of urinary oxalate per day (912 μmol), and persons with primary hyperoxaluria may excrete at least 200 mg per day (2280 μmol).

Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, engineered meganucleases described herein, polynucleotides encoding the same, or cells expressing the same, are typically admixed with a pharmaceutically acceptable carrier and the resulting composition is administered to a subject. The carrier must be acceptable in the sense of being compatible with any other ingredients in the formulation and must not be deleterious to the subject. The carrier can be a solid or a liquid, or both, and can be formulated with the compound as a unit-dose formulation.

In some embodiments, pharmaceutical compositions of the invention can further comprise one or more additional agents or biological molecules useful in the treatment of a disease in the subject. Likewise, the additional agent(s) and/or biological molecule(s) can be co-administered as a separate composition.

The pharmaceutical compositions described herein can include a therapeutically effective amount of any engineered meganuclease disclosed herein, or any polynucleotide described herein encoding any engineered meganuclease described herein. For example, in some embodiments, the pharmaceutical composition can include polynucleotides described herein at any of the doses (e.g., gc/kg of an encoding nucleic acid sequence or mg/kg of mRNA) described herein.

In particular embodiments of the invention, the pharmaceutical composition can comprise one or more recombinant viruses (e.g., recombinant AAVs) described herein that comprise one or more polynucleotides described herein (i.e., packaged within the viral genome). In particular embodiments, the pharmaceutical composition comprises two or more recombinant viruses (e.g., recombinant AAVs) described herein, each comprising a polynucleotide comprising a nucleic acid sequence encoding a different engineered meganuclease described herein. For example, a first recombinant virus (e.g., recombinant AAV) may comprise a first polynucleotide comprising a first nucleic acid sequence encoding a first engineered meganuclease described herein having specificity for the HAO 25-26 recognition sequence, and a second recombinant virus (e.g., recombinant AAV)

comprising a second polynucleotide comprising a second nucleic acid sequence encoding a second engineered meganuclease described herein having specificity for the HAO 25-26 recognition sequence, or for a different recognition sequence within the HAO1 gene. The expression of such a pair of engineered meganucleases in the same cell (e.g., a liver cell) would allow for the disruption (e.g., by introduction of a stop codon in) the HAO1 gene according to the invention.

In some embodiments, the engineered meganuclease is expressed in a eukaryotic cell in vivo; wherein the engineered meganuclease produces a cleavage site within the recognition sequence and generates a modified HAO1 gene that does not encode a full-length endogenous HAO1 polypeptide.

A "therapeutically effective amount" refers to an amount effective, at dosages and for periods of time necessary, to achieve a desired therapeutic result. The therapeutically effective amount may vary according to factors such as the age, sex, and weight of the individual, and the ability of the polypeptide, nucleic acid, or vector to elicit a desired response in the individual. As used herein a therapeutically result can refer to a reduction of serum oxalate level, a reduction in urinary oxalate level, an increase in the glycolate/creatinine ratio, a decrease in the oxalate/creatinine ratio, a decrease in calcium precipitates in the kidney, and/or a decrease in the risk of renal failure.

The pharmaceutical compositions described herein can include an effective amount of any engineered meganuclease, or a nucleic acid encoding an engineered meganuclease of the invention. In some embodiments, the pharmaceutical composition comprises about $1\times10^{10}$ gc/kg to about $1\times10^{14}$ gc/kg (e.g., $1\times10^{10}$ gc/kg, $1\times10^{11}$ gc/kg, $1\times10^{12}$ gc/kg, $1\times10^{13}$ gc/kg, or $1\times10^{14}$ gc/kg) of a nucleic acid encoding an engineered meganuclease. In some embodiments, the pharmaceutical composition comprises at least about $1\times10^{10}$ gc/kg, at least about $1\times10^{11}$ gc/kg, at least about $1\times10^{12}$ gc/kg, at least about $1\times10^{13}$ gc/kg, or at least about $1\times10^{14}$ gc/kg of a nucleic acid encoding an engineered meganuclease. In some embodiments, the pharmaceutical composition comprises about $1\times10^{10}$ gc/kg to about $1\times10^{11}$ gc/kg, about $1\times10^{11}$ gc/kg to about $1\times10^{12}$ gc/kg, about $1\times10^{12}$ gc/kg to about $1\times10^{13}$ gc/kg, or about $1\times10^{13}$ gc/kg to about $1\times10^{14}$ gc/kg of a nucleic acid encoding an engineered meganuclease. In certain embodiments, the pharmaceutical composition comprises about $1\times10^{12}$ gc/kg to about $9\times10^{13}$ gc/kg (e.g., about $1\times10^{12}$ gc/kg, about $2\times10^{12}$ gc/kg, about $3\times10^{12}$ gc/kg, about $4\times10^{12}$ gc/kg, about $5\times10^{12}$ gc/kg, about $6\times10^{12}$ gc/kg, about $7\times10^{12}$ gc/kg, about $8\times10^{12}$ gc/kg, about $9\times10^{12}$ gc/kg, about $1\times10^{13}$ gc/kg, about $2\times10^{13}$ gc/kg, about $3\times10^{13}$ gc/kg, about $4\times10^{13}$ gc/kg, about $5\times10^{13}$ gc/kg, about $6\times10^{13}$ gc/kg, about $7\times10^{13}$ gc/kg, about $8\times10^{13}$ gc/kg, or about $9\times10^{13}$ gc/kg) of a nucleic acid encoding an engineered meganuclease.

In particular embodiments of the invention, the pharmaceutical composition can comprise one or more mRNAs described herein encapsulated within lipid nanoparticles.

Some lipid nanoparticles contemplated for use in the invention comprise at least one cationic lipid, at least one non-cationic lipid, and at least one conjugated lipid. In more particular examples, lipid nanoparticles can comprise from about 50 mol % to about 85 mol % of a cationic lipid, from about 13 mol % to about 49.5 mol % of a non-cationic lipid, and from about 0.5 mol % to about 10 mol % of a lipid conjugate, and are produced in such a manner as to have a non-lamellar (i.e., non-bilayer) morphology. In other particular examples, lipid nanoparticles can comprise from about 40 mol % to about 85 mol % of a cationic lipid, from about 13 mol % to about 49.5 mol % of a non-cationic lipid, and from about 0.5 mol % to about 10 mol % of a lipid conjugate and are produced in such a manner as to have a non-lamellar (i.e., non-bilayer) morphology.

Cationic lipids can include, for example, one or more of the following: palmitoyi-oleoyl-nor-arginine (PONA), MPDACA, GUADACA, ((6Z,9Z,28Z,31Z)-heptatriaconta-6,9,28,31-tetraen-19-yl 4-(dimethylamino)butanoate) (MC3), LenMC3, CP-LenMC3, γ-LenMC3, CP-γ-LenMC3, MC3MC, MC2MC, MC3 Ether, MC4 Ether, MC3 Amide, Pan-MC3, Pan-MC4 and Pan MC5, 1,2-dilinoleyloxy-N,N-dimethylaminopropane (DLinDMA), 1,2-dilinolenyloxy-N,N-dimethylaminopropane (DLenDMA), 2,2-dilinoleyl-4-(2-dimethylaminoethyl)-[1,3]-dioxolane (DLin-K-C2-DMA; "XTC2"), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K-C4-DMA), 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 2,2-dilinoleyl-4-dimethylaminomethyl-[1,3]-dioxolane (DLin-K-DMA), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), 1,2-dioleyloxy-N,N-dimethylaminopropane (DODMA), 1,2-distearyloxy-N,N-dimethylaminopropane (DSDMA), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethy-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), or mixtures thereof. The cationic lipid can also be DLinDMA, DLin-K-C2-DMA ("XTC2"), MC3, LenMC3, CP-LenMC3, γ-LenMC3, CP-γ-LenMC3, MC3MC, MC2MC, MC3 Ether, MC4 Ether, MC3 Amide, Pan-MC3, Pan-MC4, Pan MC5, or mixtures thereof.

In various embodiments, the cationic lipid may comprise from about 50 mol % to about 90 mol %, from about 50 mol % to about 85 mol %, from about 50 mol % to about 80 mol %, from about 50 mol % to about 75 mol %, from about 50 mol % to about 70 mol %, from about 50 mol % to about 65 mol %, or from about 50 mol % to about 60 mol % of the total lipid present in the particle.

In other embodiments, the cationic lipid may comprise from about 40 mol % to about 90 mol %, from about 40 mol % to about 85 mol %, from about 40 mol % to about 80 mol %, from about 40 mol % to about 75 mol %, from about 40 mol % to about 70 mol %, from about 40 mol % to about 65 mol %, or from about 40 mol % to about 60 mol % of the total lipid present in the particle.

The non-cationic lipid may comprise, e.g., one or more anionic lipids and/or neutral lipids. In particular embodiments, the non-cationic lipid comprises one of the following neutral lipid components: (1) cholesterol or a derivative thereof; (2) a phospholipid; or (3) a mixture of a phospholipid and cholesterol or a derivative thereof. Examples of cholesterol derivatives include, but are not limited to, cholestanol, cholestanone, cholestenone, coprostanol, cholesteryl-2'-hydroxyethyl ether, cholesteryl-4'-hydroxybutyl ether, and mixtures thereof. The phospholipid may be a neutral lipid including, but not limited to, dipalmitoylphosphatidylcholine (DPPC), distearoylphosphatidylcholine (DSPC), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), egg phosphatidylcholine (EPC), and mixtures thereof. In certain embodiments, the phospholipid is DPPC, DSPC, or mixtures thereof.

In some embodiments, the non-cationic lipid (e.g., one or more phospholipids and/or cholesterol) may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle. When the non-cationic lipid is a mixture of a phospholipid and cholesterol or a cholesterol derivative, the mixture may comprise up to about 40, 50, or 60 mol % of the total lipid present in the particle.

The conjugated lipid that inhibits aggregation of particles may comprise, e.g., one or more of the following: a polyethyleneglycol (PEG)-lipid conjugate, a polyamide (ATTA)-lipid conjugate, a cationic-polymer-lipid conjugates (CPLs), or mixtures thereof. In one particular embodiment, the nucleic acid-lipid particles comprise either a PEG-lipid conjugate or an ATTA-lipid conjugate. In certain embodiments, the PEG-lipid conjugate or ATTA-lipid conjugate is used together with a CPL. The conjugated lipid that inhibits aggregation of particles may comprise a PEG-lipid including, e.g., a PEG-diacylglycerol (DAG), a PEG dialkyloxypropyl (DAA), a PEG-phospholipid, a PEG-ceramide (Cer), or mixtures thereof. The PEG-DAA conjugate may be PEG-di lauryloxypropyl (C12), a PEG-dimyristyloxypropyl (C14), a PEG-dipalmityloxypropyl (C16), a PEG-distearyloxypropyl (C18), or mixtures thereof.

Additional PEG-lipid conjugates suitable for use in the invention include, but are not limited to, mPEG2000-1,2-di-O-alkyl-sn3-carbomoylglyceride (PEG-C-DOMG). The synthesis of PEG-C-DOMG is described in PCT Application No. PCT/US08/88676. Yet additional PEG-lipid conjugates suitable for use in the invention include, without limitation, 1-[8'-(1,2-dimyristoyl-3-propanoxy)-carboxamido-3',6'-dioxaoctanyl]carbamoyl-ω-methyl-poly(ethylene glycol) (2KPEG-DMG). The synthesis of 2KPEG-DMG is described in U.S. Pat. No. 7,404,969.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

In other embodiments, the composition may comprise amphoteric liposomes, which contain at least one positive and at least one negative charge carrier, which differs from the positive one, the isoelectric point of the liposomes being between 4 and 8. This objective is accomplished owing to the fact that liposomes are prepared with a pH-dependent, changing charge.

Liposomal structures with the desired properties are formed, for example, when the amount of membrane-forming or membrane-based cationic charge carriers exceeds that of the anionic charge carriers at a low pH and the ratio is reversed at a higher pH. This is always the case when the ionizable components have a pKa value between 4 and 9. As the pH of the medium drops, all cationic charge carriers are charged more and all anionic charge carriers lose their charge.

Cationic compounds useful for amphoteric liposomes include those cationic compounds previously described herein above. Without limitation, strongly cationic compounds can include, for example: DC-Chol 3-β-[N—(N',N'-dimethylmethane) carbamoyl] cholesterol, TC-Chol 3-β-[N—(N',N',N'-trimethylaminoethane) carbamoyl cholesterol, BGSC bisguanidinium-spermidine-cholesterol, BGTC bis-guadinium-tren-cholesterol, DOTAP (1,2-dioleoyloxypropyl)-N,N,N-trimethylammonium chloride, DOSPER (1,3-dioleoyloxy-2-(6-carboxy-spermyl)-propylarnide, DOTMA (1,2-dioleoyloxypropyl)-N,N,N-trimethylamronium chloride) (Lipofectin®), DORIE 1,2-dioleoyloxypropyl)-3-dimethylhydroxyethylammonium bromide, DOSC (1,2-dioleoyl-3-succinyl-sn-glyceryl choline ester), DOGSDSO (1,2-dioleoyl-sn-glycero-3-succinyl-2-hydroxyethyl disulfide omithine), DDAB dimethyldioctadecylammonium bromide, DOGS ((C18)2GlySper3+) N,N-dioctadecylamido-glycol-spermin (Transfectam®) (C18)2Gly+N, N-dioctadecylamido-glycine, CTAB cetyltrimethylarnmonium bromide, CpyC cetylpyridinium chloride, DOEPC 1,2-dioleoly-sn-glycero-3-ethylphosphocholine or other O-alkyl-phosphatidylcholine or ethanolamines, amides from lysine, arginine or ornithine and phosphatidyl ethanolamine.

Examples of weakly cationic compounds include, without limitation: His-Chol (histaminyl-cholesterol hemisuccinate), Mo-Chol (morpholine-N-ethylamino-cholesterol hemisuccinate), or histidinyl-PE.

Examples of neutral compounds include, without limitation: cholesterol, ceramides, phosphatidyl cholines, phosphatidyl ethanolamines, tetraether lipids, or diacyl glycerols.

Anionic compounds useful for amphoteric liposomes include those non-cationic compounds previously described herein. Without limitation, examples of weakly anionic compounds can include: CHEMS (cholesterol hemisuccinate), alkyl carboxylic acids with 8 to 25 carbon atoms, or diacyl glycerol hemisuccinate. Additional weakly anionic compounds can include the amides of aspartic acid, or glutamic acid and PE as well as PS and its amides with glycine, alanine, glutamine, asparagine, serine, cysteine, threonine, tyrosine, glutamic acid, aspartic acid or other amino acids or aminodicarboxylic acids. According to the same principle, the esters of hydroxycarboxylic acids or hydroxydicarboxylic acids and PS are also weakly anionic compounds.

In some embodiments, amphoteric liposomes may contain a conjugated lipid, such as those described herein above. Particular examples of useful conjugated lipids include, without limitation, PEG-modified phosphatidylethanolamine and phosphatidic acid, PEG-ceramide conjugates (e.g., PEG-CerC14 or PEG-CerC20), PEG-modified dialkylamines and PEG-modified 1,2-diacyloxypropan-3-amines. Particular examples are PEG-modified diacylglycerols and dialkylglycerols.

In some embodiments, the neutral lipids may comprise from about 10 mol % to about 60 mol %, from about 15 mol % to about 60 mol %, from about 20 mol % to about 60 mol %, from about 25 mol % to about 60 mol %, from about 30 mol % to about 60 mol %, from about 10 mol % to about 55 mol %, from about 15 mol % to about 55 mol %, from about 20 mol % to about 55 mol %, from about 25 mol % to about 55 mol %, from about 30 mol % to about 55 mol %, from about 13 mol % to about 50 mol %, from about 15 mol % to about 50 mol % or from about 20 mol % to about 50 mol % of the total lipid present in the particle.

In some cases, the conjugated lipid that inhibits aggregation of particles (e.g., PEG-lipid conjugate) may comprise from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 1 mol % to about 1.8 mol %, from about 1.2 mol % to about 1.8 mol %, from about 1.2 mol % to about 1.7 mol %, from about 1.3 mol % to about 1.6 mol %, from about 1.4 mol % to about 1.5 mol %, or about 1, 1.1, 1.2, 1.3, 1.4, 1.5, 1.6, 1.7, 1.8, 1.9, or 2 mol % (or any fraction thereof or range therein) of the total lipid present in the particle. Typically, in such instances, the PEG moiety has an average molecular weight of about 2,000 Daltons. In other cases, the conjugated lipid that inhibits aggregation of particles (e.g., PEG-lipid conjugate) may comprise from about 5.0 mol % to about 10 mol %, from about 5 mol % to about 9 mol %, from about 5 mol % to about 8 mol %, from about 6 mol % to about 9 mol %, from about 6 mol % to about 8 mol %, or about 5 mol %, 6 mol %, 7 mol %, 8 mol %, 9 mol %, or 10 mol % (or any fraction thereof or range therein) of the total lipid present in the particle. Typically, in such instances, the PEG moiety has an average molecular weight of about 750 Daltons.

Considering the total amount of neutral and conjugated lipids, the remaining balance of the amphoteric liposome can comprise a mixture of cationic compounds and anionic compounds formulated at various ratios. The ratio of cationic to anionic lipid may selected in order to achieve the desired properties of nucleic acid encapsulation, zeta potential, pKa, or other physicochemical property that is at least in part dependent on the presence of charged lipid components.

In some embodiments, the lipid nanoparticles have a composition, which specifically enhances delivery and uptake in the liver, and specifically within hepatocytes.

In some embodiments, pharmaceutical compositions of the invention can further comprise one or more additional agents useful in the treatment of PH1 in the subject.

The present disclosure also provides engineered meganucleases described herein, or polynucleotides described herein encoding the same, or cells described herein expressing engineered meganucleases described herein for use as a medicament. The present disclosure further provides the use of engineered meganucleases described herein, or polynucleotides disclosed herein encoding the same, or cells described herein expressing engineered meganucleases described herein in the manufacture of a medicament for treating PH1, for increasing levels of a modified HAO1 protein (i.e., a truncated HAO1 protein), or reducing the symptoms associated with PH1.

2.5 Methods for Producing Recombinant Viruses

In some embodiments, the invention provides recombinant viruses, such as recombinant AAVs, for use in the methods of the invention. Recombinant AAVs are typically produced in mammalian cell lines such as HEK293. Because the viral cap and rep genes are removed from the recombinant virus to prevent its self-replication to make room for the therapeutic gene(s) to be delivered (e.g. the meganuclease gene), it is necessary to provide these in trans in the packaging cell line. In addition, it is necessary to provide the "helper" (e.g. adenoviral) components necessary to support replication (Cots D et al., (2013) Curr. Gene Ther. 13(5): 370-81). Frequently, recombinant AAVs are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the recombinant viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells.

The nuclease can be placed under the control of a tissue-specific promoter that is not active in the packaging cells. Any tissue specific promoter described herein for expression of the engineered meganuclease or for a nucleic acid sequence of interest can be used. For example, if a recombinant virus is developed for delivery of genes encoding an engineered meganuclease to liver tissue, a liver-specific promoter can be used. Examples of liver-specific promoters include, without limitation, those liver-specific promoters described elsewhere herein.

Alternatively, the recombinant virus can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a particular embodiment, viral particles are produced in insect cells using the baculovirus system as described by Gao, et al. (Gao et al. (2007), J. Biotechnol. 131(2):138-43). A meganuclease under the control of a mammalian promoter is unlikely to be expressed in these cells (Airenne et al. (2013), Mol. Ther. 21(4): 739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen, H (2012) Mol Ther Nucleic Acids. 1(11): e57).

The engineered meganuclease gene can be operably linked to an inducible promoter such that a small-molecule inducer is required for meganuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the engineered meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the engineered meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another particular embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the meganuclease gene will be repressed only in the packaging cells expressing the repressor and not in target cells or tissues transduced with the resulting recombinant AAV.

2.6 Engineered Meganuclease Variants

Embodiments of the invention encompass the engineered meganucleases described herein, and variants thereof. Further embodiments of the invention encompass polynucleotides comprising a nucleic acid sequence encoding the engineered meganucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to bind and cleave a HAO1 gene recognition sequence described herein (e.g., a HAO 25-26 recognition sequence). Such variants may result, for example, from human manipulation. Biologically active variants of a native polypeptide of the embodiments (e.g., SEQ ID NOs: 5-11), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide, native subunit, native HVR1 region, and/or native HVR2 region, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 that has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of any one of SEQ ID NOs: 5-11.

In certain embodiments, engineered meganucleases of the invention comprise an HVR2 that has 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 215-270 of any one of SEQ ID NOs: 5-11.

A substantial number of amino acid modifications to the DNA recognition domain of the wild-type I-CreI meganuclease have previously been identified (e.g., U.S. Pat. No. 8,021,867), which singly or in combination, result in engineered meganucleases with specificities altered at individual bases within the DNA recognition sequence half-site, such that the resulting rationally-designed meganucleases have half-site specificities different from the wild-type enzyme. Table 2 provides potential substitutions that can be made in an engineered 10 meganuclease monomer or subunit to enhance specificity based on the base present at each half-site position (−1 through −9) of a recognition half-site.

TABLE 2

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75<br>L75*<br>C75*<br>Y139*<br>C46*<br>A46* | **R70***<br>H75*<br>R75*<br>H46*<br>K46*<br>R46* | K70<br>E70*<br>E75*<br>E46*<br>D46* | Q70*<br>C70<br>L70<br>Y75*<br>Q75*<br>H75*<br>H139<br>Q46*<br>H46* | | | | **T46*** | | | G70<br>A70<br>S70<br>G46* |
| −2 | Q70<br>T44*<br>A44*<br>V44*<br>I44*<br>L44*<br>N44* | E70<br>D70<br>K44*<br>R44* | H70<br>D44*<br>E44* | **Q44*** | C44* | | | | | | |
| −3 | Q68<br>C24* | E68<br>F68 | **R68** | M68<br>C68 | | H68 | | Y68 | K68 | | |

TABLE 2-continued

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| | **I24*** | K24* | | L68 | | | | | | | |
| | | R24* | | F68 | | | | | | | |
| −4 | A26* | E77 | R77 | | | | | S77 | | | S26* |
| | Q77 | K26* | E26* | | | | | **Q26*** | | | |
| −5 | | E42 | R42 | | | **K28*** | C28* | | | | M66 |
| | | | | | | | Q42 | | | | K66 |
| −6 | Q40 | E40 | R40 | C40 | A40 | | | | | | **S40** |
| | C28* | R28* | | I40 | A79 | | | | | | S28* |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | **N30*** | E38 | K38 | I38 | | | C38 | | | | H38 |
| | **Q38** | K30* | R38 | L38 | | | | | | | N38 |
| | | R30* | E30* | | | | | | | | Q30* |
| −8 | F33 | E33 | F33 | L33 | | R32* | R33 | | | | |
| | **Y33** | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | D32 | | | **S32** |
| | | | K32 | V32 | | | | I32 | | | N32 |
| | | | | A32 | | | | | | | H32 |
| | | | | C32 | | | | | | | Q32 |
| | | | | | | | | | | | T32 |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or any one of SEQ ID NOs: 5-11 (WO 2009/001159), a Y, R, K, or D at a residue corresponding to position 66 of I-CreI or any one of SEQ ID NOs: 5-11, and/or an E, Q, or K at a residue corresponding to position 80 of I-CreI or any one of SEQ ID NOs: 5-11 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant meganuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its intended activity. For example, variants of an engineered meganuclease would be screened for their ability to preferentially bind and cleave recognition sequences found within a dystrophin gene ability to preferentially bind and cleave recognition sequences found within a HAO1 gene.

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Editing of the HAO 25-26 Recognition Sequence in a Reporter Cell Line

1. Methods and Materials

The purpose of this experiment was to determine whether HAO 25-26 meganucleases could bind and cleave their respective human recognition sequences in mammalian cells. Each engineered meganuclease was evaluated using the CHO cell reporter assay previously described (see, WO/2012/167192). To perform the assays, CHO cell reporter lines were produced, which carried a non-functional Green Fluorescent Protein (GFP) gene expression cassette integrated into the genome of the cells. The GFP gene in each cell line contains a direct sequence duplication separated by a pair of recognition sequences such that intracellular cleavage of either recognition sequence by a meganuclease would stimulate a homologous recombination event resulting in a functional GFP gene.

In CHO reporter cell lines developed for this study, one recognition sequence inserted into the GFP gene was the human HAO 25-26 recognition sequence (SEQ ID NO: 3). The second recognition sequence inserted into the GFP gene was a CHO-23/24 recognition sequence, which is recognized and cleaved by a control meganuclease called "CHO-23/24." The CHO-23/24 recognition sequence is used as a positive control and standard measure of activity.

CHO reporter cells were transfected with mRNA encoding the HAO 25-26x.227 (SEQ ID NO: 9) and HAO 25-26x.268 (SEQ ID NO: 8) nucleases, which included an N-terminal SV40 nuclear localization sequence (SEQ ID NO: 37), which is included at the N-terminus of all HAO 25-26 meganucleases described in the examples (unless otherwise noted). A control sample of CHO reporter cells were transfected with mRNA encoding the CHO-23/24 meganuclease. In each assay, 5e4 CHO reporter cells were transfected with 90 ng of mRNA in a 96-well plate using Lipofectamine® MessengerMax (ThermoFisher) according to the manufacturer's instructions. The transfected CHO cells were evaluated by flow cytometry at 2 days, 5 days, and 7 days post transfection to determine the percentage of GFP-positive cells compared to an untransfected negative control. Data obtained at each time point was normalized to the % GFP positive cells observed using the CHO-23/24 meganuclease to determine an "activity score," and the normalized data from the earliest time point was subtracted from that of the latest time point to determine a "toxicity score." The activity and toxicity scores were then added together to determine an "activity index," which was then normalized to the activity index of the CHO-23/24 meganuclease to compare data between cell lines ("normalized activity index").

2. Results

Figure 5:
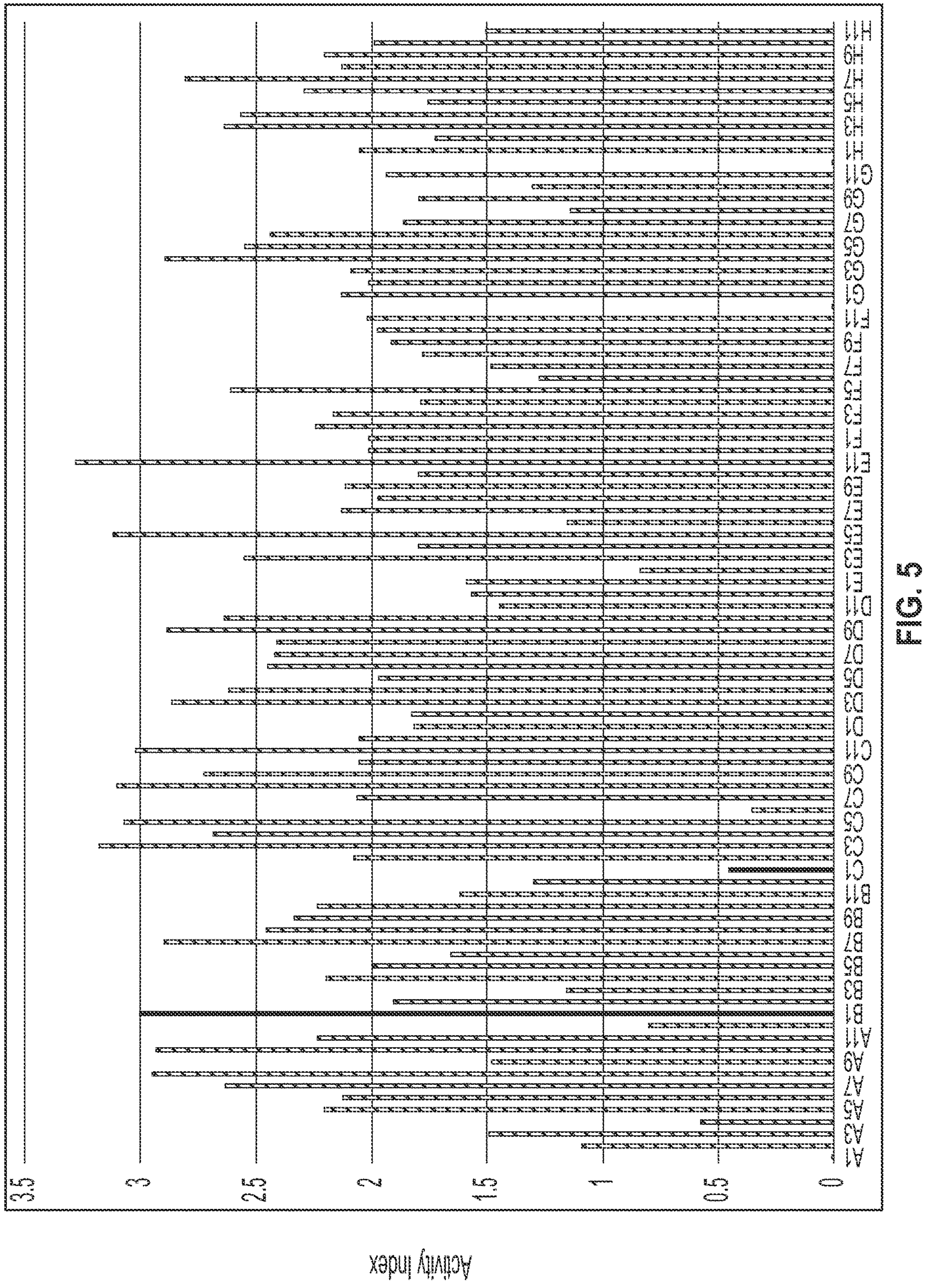
FIG. 5 provides an activity index of HAO 25-26 meganucleases evaluated in the CHO cell reporter assay.

The HAO 25-26 meganucleases evaluated in this experiment were optimized and selected from an HAO 25-26 meganuclease shown in well C1 of FIG. 5. As shown, the positive control CHO-23/24 in well B1 exhibited a normalized activity index of 3. Out of 93 HAO 25-26 meganucleases screened in this round of selections, six nucleases showed higher scores than the HAO 25-26 meganuclease from which they were optimized and surpassed the CHO-23/24 control score. HAO 25-26x.227 (well D6) and HAO 25-26x.268 (well E11) both showed significant improvements in activity compared to the HAO 25-26 meganuclease from which they were optimized, and HAO 25-26x.268 also out-performed the CHO-23/24 control.

3. Conclusions

This assay allowed for the identification of a subset of HAO 25-26 meganucleases for subsequent analysis based on their activity in mammalian cells. Both HAO 25-26x.227 and HAO 25-26x.268 outperformed the HAO 25-26 meganuclease from which they were optimized and exhibited a favorable activity index in the assay.

Example 2

Editing of HAO 25-26 Recognition Sequence in Human Cell Lines

1. Methods and Materials

These studies were conducted using in vitro cell-based systems to evaluate editing efficiencies of different HAO 25-26 meganucleases by digital PCR using an indel detection assay.

In these experiments, mRNA encoding the HAO 25-26x.227 or HAO 25-26x.268 meganucleases were electroporated into human cells (HEK293 100 ng or 2 ng; Hep3B 50 ng or 5 ng; and HepG2 250 ng or 8 ng) using the Lonza Amaxa 4D system. Additionally, some cells were electroporated with mRNA encoding GFP, or mRNA encoding an HAO 3-4x.47 meganuclease, which targets a different recognition sequence (referred to as HAO 3-4) in the HAO1 gene. All meganucleases included an N-terminal SV40 NLS as described in Example 1.

Cells were collected at two days post electroporation for gDNA preparation and evaluated for transfection efficiency using a Beckman Coulter CytoFlex S cytometer. Transfection efficiency exceeded 90%. Two additional time points were collected at between 4 and 9-days post electroporation for gDNA extractions. gDNA was prepared using the Macherey Nagel NucleoSpin Blood QuickPure kit.

Digital droplet PCR was utilized to determine the frequency of target insertions and deletions (indel %) using primers P1, F1, and R1 at the HAO 25-26 recognition sequence, as well as primers P2, F2, R2 to generate a reference amplicon. Digital droplet PCR was utilized to determine the frequency of target insertions and deletions (indel %) using primers P1, F1, and R1 at the HAO 3-4 recognition sequence, as well as primers P3, F3, R3 to generate a reference amplicon Amplifications were multiplexed in a 20 uL reaction containing 1× ddPCR Supermix for Probes (no dUTP, BioRad), 250 nM of each probe, 900 nM of each primer, 5U of HindIII-HF, and about 50 ng cellular gDNA. Droplets were generated using a QX100 droplet generator (BioRad). Cycling conditions for HAO 25-26 were as follows: 1 cycle of 95° C. (2° C./s ramp) for 10 minutes, 44 cycles of 94° C. (1° C./s ramp) for 30 seconds, 62° C. (1° C./s ramp) for 30 seconds, 72 C (0.2° C./s ramp) for 2 minutes, 1 cycle of 98° C. for 10 minutes, 4° C. hold. Cycling conditions for HAO 3-4 were as follows: 1 cycle of 95° C. (2° C./s ramp) for 10 minutes, 44 cycles of 94° C. (1° C./s ramp) for 30 seconds, 55° C. (1° C./s ramp) for 30 seconds, 72 C (0.2° C./s ramp) for 2 minutes, 1 cycle of 98° C. for 10 minutes, 4° C. hold.

Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

```
Primer Sets
P1: 34 HAO 25/26 P1 BS PROBE:
                                        (SEQ ID NO: 39)
TTGGATACAGCTTCCATCTA FAM

F1: 21-HAO 25-25-15-16 F2:
                                        (SEQ ID NO: 40)
ACCAAACAAACAGTAAAATTGCC
```

-continued

R1: 14-HAO15-16 25-26 R:
(SEQ ID NO: 41)
GAGGTCGATAAACGTTAGCCTC

P2: 44 12 REF PROBE1:
(SEQ ID NO: 42)
TGTGGTCACCCTCTGCACAGTGT HEX

F2: 28-HAO21-22 F2:
(SEQ ID NO: 43)
CCACATAAGATTTGGCAAGCC

R2: 27-HAO21-22 R2:
(SEQ ID NO: 44)
TGTGGTCACCCTCTGCACAGTGT

P3: 46 3-4INDELBHQ59 BS PROBE:
(SEQ ID NO: 45)
CCTGTAATAGTCATATATAGAC

F3: HAO3-4.DPCR F1:
(SEQ ID NO: 46)
TCCATCTGGGATAGCAATAACC

R3: HAO3-4.DPCR R2:
(SEQ ID NO: 47)
CAGCCAAAGTTTCTTCATCATTTG

2. Results

Figure 6A:
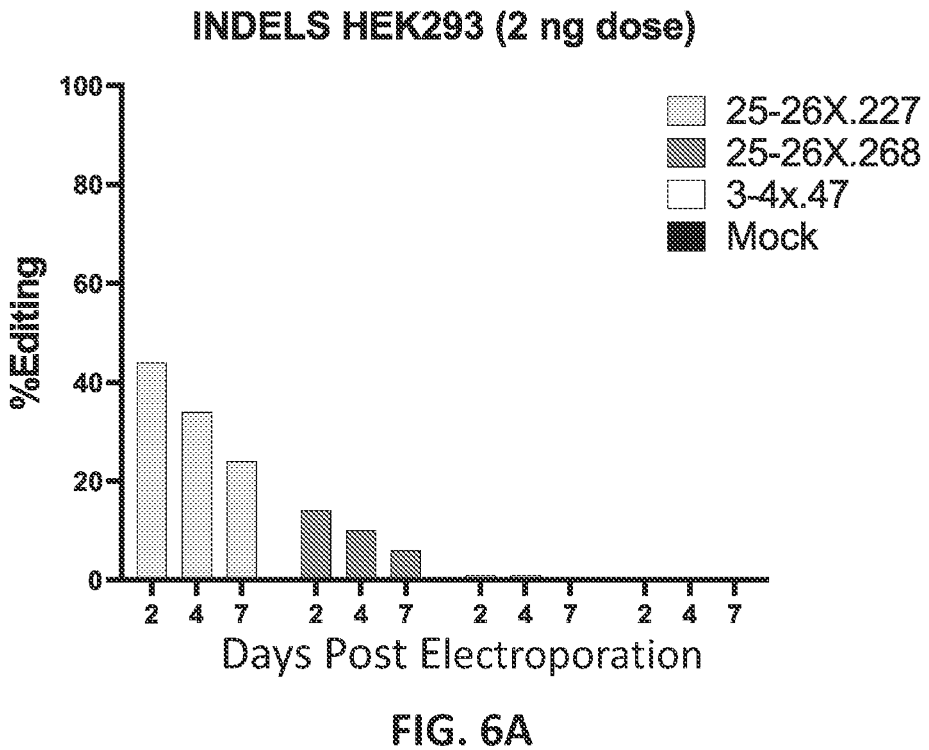
FIGS. 6A and 6B show the frequency of indel generation in HEK293 cells over time following introduction of low and high doses of mRNA encoding the HAO 25-26x.227, HAO 25-26x.268, and HAO 3-4x.47 meganucleases.
Figure 6B:
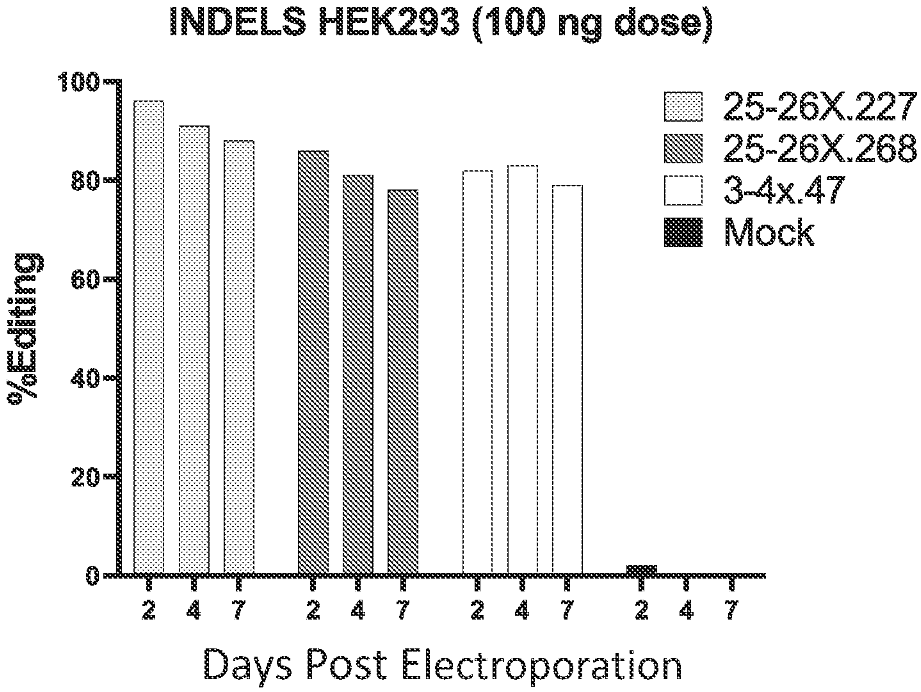

In these studies, indels (insertions and deletions) were measured by ddPCR across multiple timepoints. In HEK293 cells (FIG. 6A), the low mRNA dose of HAO 25-26x.227 showed indels ranging from >40% at day 2 to >20% at day 9. Indels for HAO 25-26x.268 ranged from 10% to 5% across time points, with indels from HAO 3-4x.47<than 5%. Indels at the high dose of mRNA were >80% across all groups and timepoints (FIG. 6B).

Figure 7A:
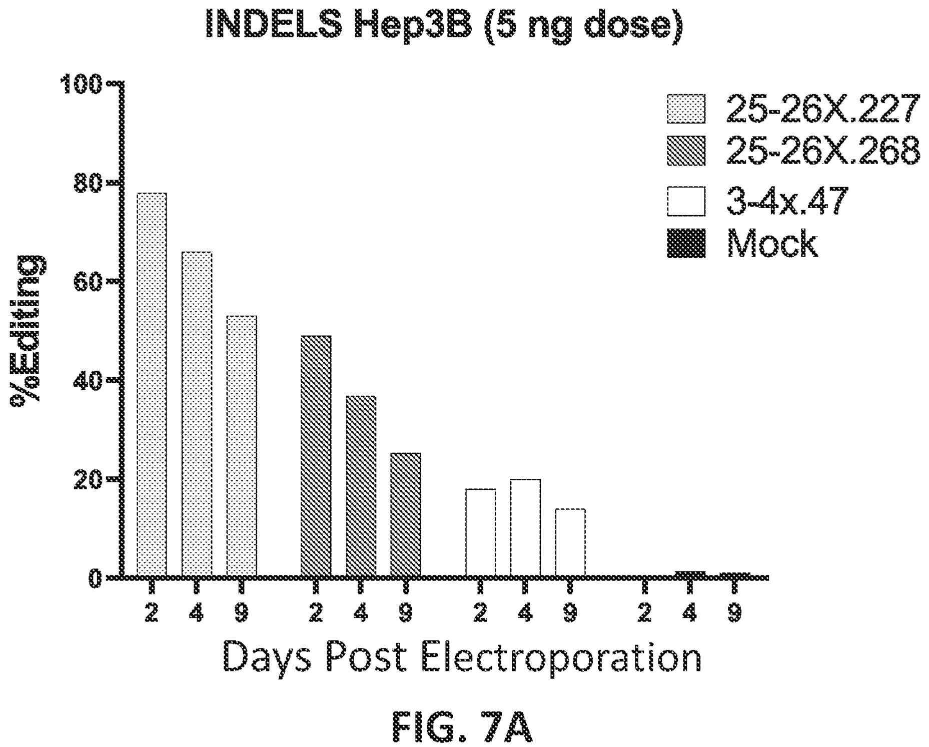
FIGS. 7A and 7B show the frequency of indel generation in Hep3B cells over time following introduction of low and high doses of mRNA encoding the HAO 25-26x.227, HAO 25-26x.268, and HAO 3-4x.47 meganucleases.
Figure 7B:
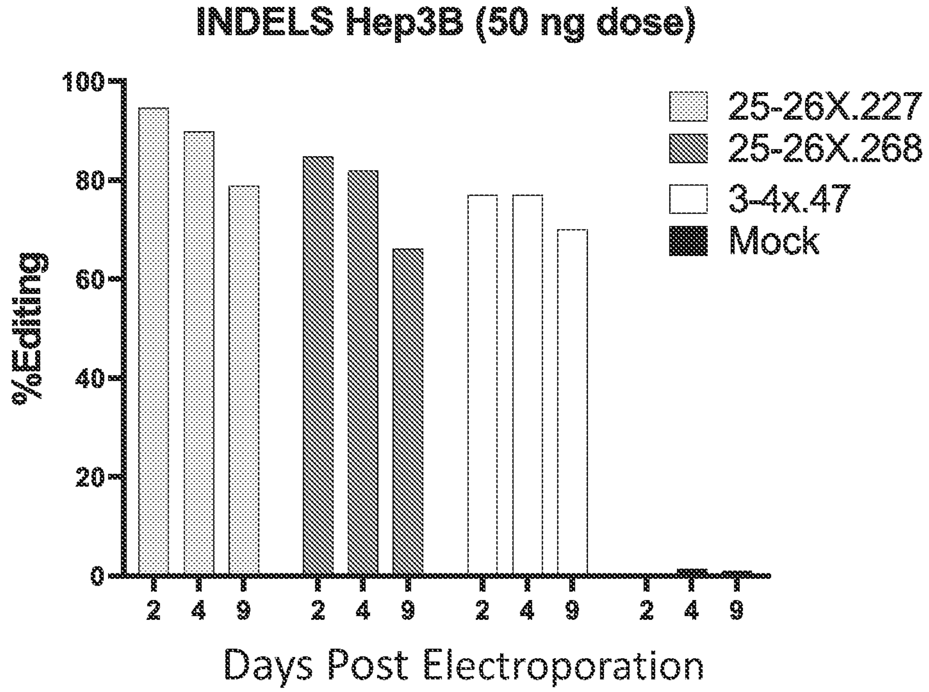

In Hep3B cells (FIG. 7A), the low mRNA dose of HAO 25-26x.227 showed indels ranging from >75% at day 2 to >50% at day 9. Indels for HAO 25-26x.268 ranged from 50% to >25% across time points, with indels from HAO 3-4x.47> than 15%. Indels at the high dose of mRNA were >80% across all groups and timepoints (FIG. 7B).

Figure 8A:
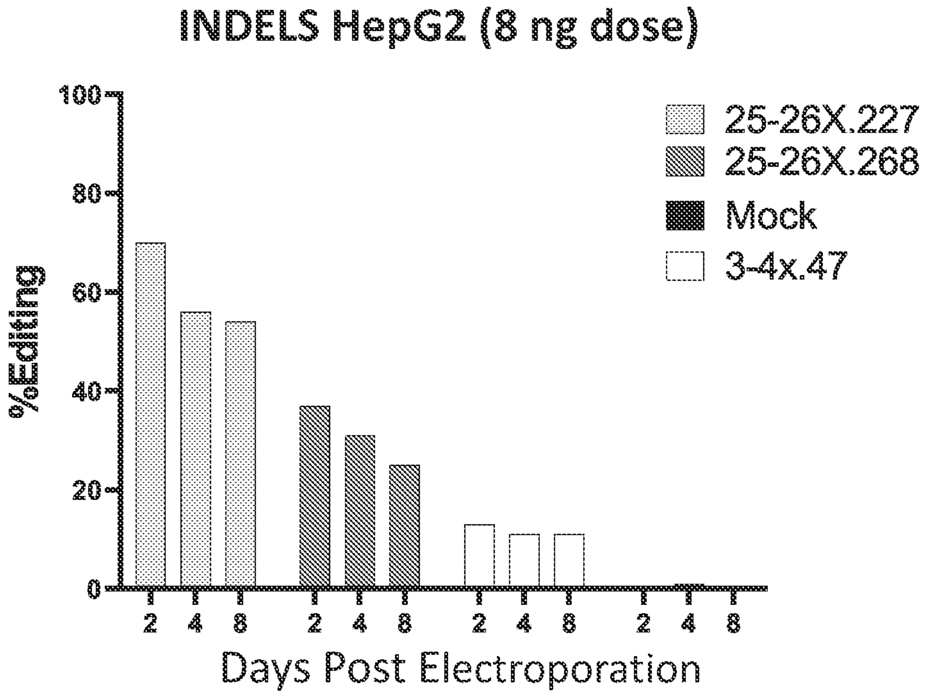
FIGS. 8A and 8B show the frequency of indel generation in HepG2 cells over time following introduction of low and high doses of mRNA encoding the HAO 25-26x.227, HAO 25-26x.268, and HAO 3-4x.47 meganucleases.
Figure 8B:
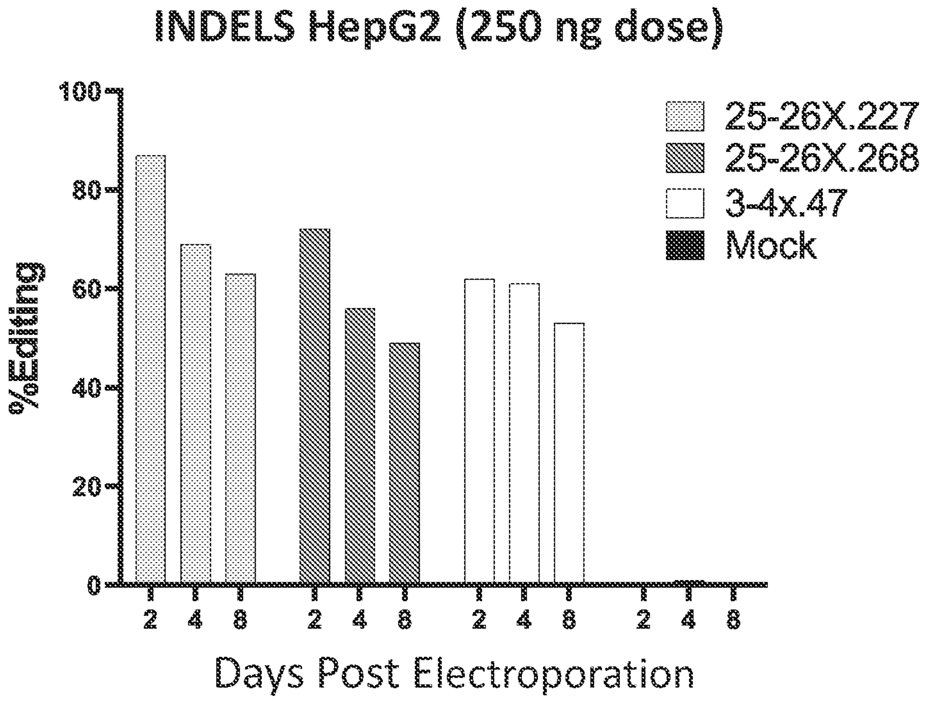

In HepG2 cells (FIG. 8A), the low mRNA dose of HAO 25-26x.227 showed indels ranging from >70% at day 2 to >55% at day 9. Indels for HAO 25-26x.268 ranged from >35% to >20% across time points, with indels from HAO 3-4x.47>15%. Indels at the high dose of mRNA were >55% across all groups and timepoints. (FIG. 8B).

3. Conclusions

These studies demonstrate the ability of the HAO 25-26 meganucleases to generate indels at the HAO 25-26 recognition sequence in multiple human cell lines in vitro. Meganucleases targeting the HAO 25-26 site were compared directly to a nuclease that targets the HAO 3-4 site, and in all cases at the low mRNA doses, the HAO 25-26 nucleases had a higher editing efficiency in the three different human cell lines.

Example 3

Dose-Dependent Indel Formation

1. Methods and Materials

These experiments were conducted using in vitro cell-based systems to evaluate the editing efficiencies of different HAO 25-26 meganucleases for potency across an mRNA dose range by digital PCR using an indel detection assay.

In these studies, mRNA encoding the HAO 25-26x.227, HAO 25-26x.268, and HAO 3-4x.47 meganucleases were electroporated into Hep3B at 50, 25, 5, 2, and 1 ng doses using the Lonza Amaxa 4D system. Each meganuclease included an N-terminal SV40 NLS as previously discussed. Cells were collected at two days post electroporation for gDNA preparation and characterized by ddPCR as described in Example 2.

2. Results

Figure 9:
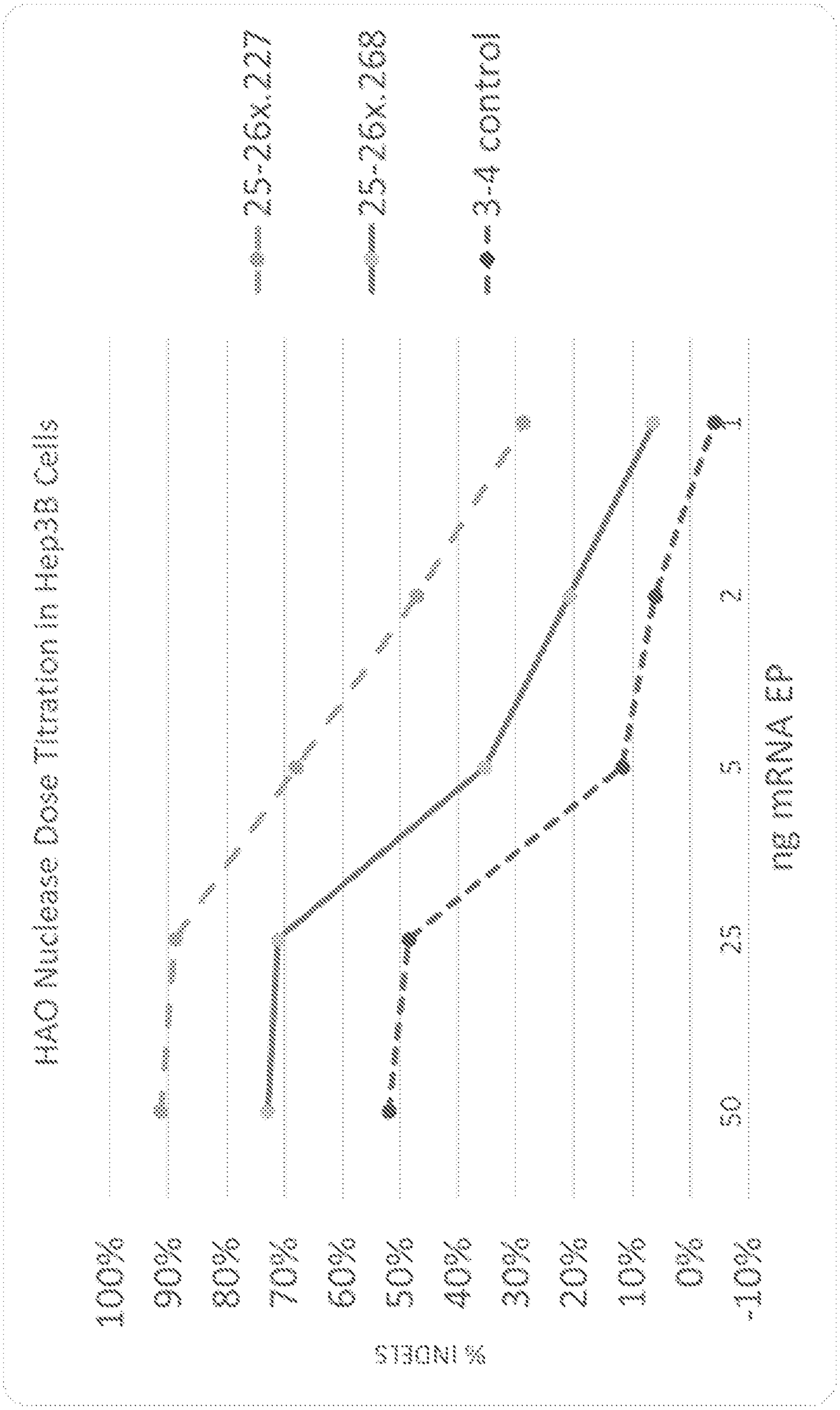
FIG. 9 shows the dose-dependent frequency of indel generation in Hep3B cells following introduction of various doses of mRNA encoding the HAO 25-26x.227, HAO 25-26x.268, and HAO 3-4x.47 meganucleases.

A dose titration comparing editing activity in Hep3B cells across multiple doses of mRNA was used to compare potency between the HAO 25-26x.227 and HAO 25-26x.268 meganucleases, as well as the HAO 3-4x.47 meganuclease that targets a different recognition sequence (FIG. 9). Editing for HAO 25-26x.227 ranged from >90% at the higher mRNA doses to >25% at the lowest mRNA dose. Editing for HAO 25-26x.268 ranged from >70% at the higher mRNA doses to >8% at the lowest mRNA dose. Editing for HAO 3-4x.47 ranged from >50% at the higher mRNA doses to >5% at 2 ng of mRNA and was not detectable the lowest mRNA dose.

3. Conclusions

These studies demonstrated that all three meganucleases tested exhibited a dose-dependent increase in the generation of indels in Hep3B cells. HOA 25-26x.227 was the most potent across all mRNA doses, with HAO 25-26x.268 showing potency less than HAO 25-26x.227, but significantly higher than HAO 3-4x.47.

Example 4

Evaluation of HAO 25-26 Meganucleases in Non-Human Primates

1. Methods and Materials

An efficacy study was conducted to evaluate the potency and functional metabolic response in non-human primates (NHPs), cynomolgus macaque, with HAO 25-26 meganucleases that target the HAO 25-26 recognition sequence in the HAO1 gene, which is conserved across NHPs and humans.

A. Experimental Design

In this study, animals were administered PBS as a control, or a transgene encoding an HAO 25-26 meganuclease, either HAO 25-26x.227 or HAO 25-26x.268, or a transgene encoding an HAO 3-4x.47 meganuclease, packaged in an AAV8 virus.

TABLE 3

| Experimental Design Scheme | | | | | |
|---|---|---|---|---|---|
| Group | Treatment | Number of NHP | Dose Conc. (VG/mL) | Dose Volume (VG/kg) | Dose Level (ml/kg) |
| 1 | PBS | 2 | 0 | 0 | 1 |
| 2 | AAV8-7478 (HAO 3-4x.47) | 3 | $3\times10^{13}$ | $3\times10^{13}$ | 1 |
| 3 | AAV8-7483 (HAO 25-26x.227) | 3 | $3\times10^{13}$ | $3\times10^{13}$ | 1 |
| 4 | AAV8-7484 (HAO 25-26x.268) | 3 | $3\times10^{13}$ | $3\times10^{13}$ | 1 |

Daily administration of anti-inflammatory drug prednisolone (1 mg/kg) started at one week prior to dose administration through scheduled termination. Animals were food fasted overnight the day prior to dosing (up to 24 hours). On the day of dose administration, animals were administered the test article/vehicle once via intravenous (IV) infusion over a 2-minute time-period followed by a 6 mL flush of saline. Restraint, temporary catheter placement and dosing procedures were completed per SRC SOPs. Individual dose volume was calculated on each individual animal's most recent body weight.

Test article was administered at $3\times10^{13}$ viral genomes (VG)/mL and intravenously (IV) infused over 2 minutes, for a final dose of $3\times10^{13}$ VG/kg.

The study duration assessed tolerability, potency and functional metabolic response from day 1 to day 43. Mortality/Moribundity was checked twice daily, while hematology, coagulation, serum chemistry, cytokines, complement activation, and serum lipid were analyzed at acclimation, pre-dose, and 1, 3, 8, 15, 22, 29, 36, and 43 days post administration of the test article. Furthermore, serum glycolate levels were analyzed at 3 days prior to dose administration, days 1 and 4 hours pre dose, and 2, 3, 8, 15, 22, 29, 36, and 43 days post administration of test articles, and were compared to PBS group. Overall potency was determined based on percent indels at time of necropsy, while tolerability was determined based on cytokine and complement induction levels and serum chemistry test.

B. Functional Metabolic Response (Serum Glycolate)

Animals were food fasted overnight the day prior to each collection (up to 24 hours). 0.5 mL of whole blood was collected via direct venipuncture of the femoral vein (or other appropriate vessel). Blood samples were placed into tubes without anticoagulant and allowed to clot for at least 30 minutes at room temperature before being prepared by centrifuging per SRC SOPs. The serum was harvested, placed into prelabeled cryovials, and temporarily stored on dry ice or frozen (−50 to −100° C.). Serum was collected for the following timepoints: day −4, days 1, 2, 3, 8, 15, 22, 29, 36, and 43. Quantification of glycolic acid and creatinine was achieved from a single 5 uL serum sample.

For each test sample, 5 μL was added to a microtiter plate. To each well was added 20 μL 80:20 acetonitrile:5 mM Ammonium Phosphate containing internal standards (ISTD) 13C2-glycolic acid and creatinine-d3. Plates were sealed and mixed vigorously before centrifugation. Injections were made directly from the preparation plate for glycolic acid analysis by HPLC-MS/MS (Agilent Ultivo) with separation on a ZIC-pHILIC column (Millipore 1504620001, 100×2.1 mm, 5 μm) using gradient elution. Following glycolic acid analysis, an additional 150 μL 80:20 acetonitrile:5 mM Ammonium Phosphate (without ISTD) was added to each well, the plate was mixed and centrifuged again before injection into the same system as for glycolic acid analysis. Quantification was based on interpolation of ISTD-normalized test sample responses from calibration curves constructed in serum replacement solution (Sigma S9388).

C. Potency/INDELs in Liver

At necropsy, liver tissue was flash frozen and stored frozen (−50 to −100° C.). gDNA was isolated from 4 sections across the liver lobes using the Macherey Nagel NucleoSpin Blood QuickPure kit.

Digital droplet PCR was utilized to determine the frequency of target insertions and deletions (indel %) using primers P1, F4, and R4 at the HAO 25-26 binding site, as well as primers P2, F2, R5 to generate a reference amplicon. Digital droplet PCR was utilized to determine the frequency of target insertions and deletions (indel %) using primers P1, F5, and R1 at the HAO 3-4 binding site, as well as primers P4, F5, R6 to generate a reference amplicon. Amplifications were multiplexed in a 20 uL reaction containing 1× ddPCR Supermix for Probes (no dUTP, BioRad), 250 nM of each probe, 900 nM of each primer, 5U of HindIII-HF, and about 50 ng cellular gDNA. Droplets were generated using a QX100 droplet generator (BioRad). Cycling conditions were as follows: 1 cycle of 95° C. (2° C./s ramp) for 10 minutes, 44 cycles of 94° C. (1° C./s ramp) for 30 seconds, 62° C. (1° C./s ramp) for 30 seconds, 72 C (0.2° C./s ramp) for 2 minutes, 1 cycle of 98° C. for 10 minutes, 4° C. hold.

Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

```
Primer Sets
P1: 34 HAO 25/26 P1 BS PROBE:
                                       (SEQ ID NO: 39)
TTGGATACAGCTTCCATCTA FAM

F4: 87 NHP HAO2526FOR:
                                       (SEQ ID NO: 48)
TTGTAAAGTCATTTGCTTGTTGGG

R4: 89 NHP HAO2526 REV:
                                       (SEQ ID NO: 49)
ACAGTCTTCCTCCTACCTCG

P2: 44 12 REF PROBE1:
                                       (SEQ ID NO: 42)
TGTGGTCACCCTCTGCACAGTGT HEX

F2: 28-HAO21-22 F2:
                                       (SEQ ID NO: 43)
CCACATAAGATTTGGCAAGCC

R5: 77 NHP HAO REF REV:
                                       (SEQ ID NO: 50)
AAAAGGTTCCTAGGACACCC
```

-continued

```
P4: 80 HAO3-4PB2 BS PROBE:
                                    (SEQ ID NO: 51)
ACTTCCAAAGTCTATATATGAC

F5: 72 NHP HAO3-4FOR:
                                    (SEQ ID NO: 52)
ACAGAACAGTGAGGATGTAGA

R6: 32-HAO23-24 R2:
                                    (SEQ ID NO: 53)
ACACACCACCAACGTAAAAC
```

D. HAO1 Protein Knock Down in the Liver

Frozen liver samples from the right and left lobes of all NHPs were processed to recover protein lysate in RIPA buffer (MilliporeSigma, Cat #EMD 20-188) supplemented with proteinase inhibitor (Sigma-Aldrich, Cat #11836170001). Samples' protein concentration was measured via BCA assay. WES analysis was performed on a Wes system (ProteinSimple, product number 004-600) according to the manufacturer's instructions using a 12-230 kDa Separation Module (ProteinSimple, Cat #SM-W004). Primary antibodies specific to HAO1 (R&D, Cat # AF6197) and Vinculin (Abcam, Cat #ab 129002) as loading control were applied at 1:10 and 1:50 working dilutions respectively, followed by HRP-conjugated secondary antibodies (Novus Biological, Cat #HAF008; R&D, Cat #HAF016) at 1:20 dilutions. The produced chemiluminescence was detected at multiple exposure times and automatically calculated by the Compass software (ProteinSimple) for HAO1 protein quantification.

E. HAO1 Message Knockdown

HAO1-encoding messenger RNA ("HAO1 message") was measured from RNA isolated from liver samples. RNA message was measured across treated groups, compared to the PBS control group and normalized to a reporter housekeeping gene, Beta-glucuronidase (GUSB). RNA was isolated from tissues using a TRIzol (Thermo Fisher Cat #15596026) Chloroform extraction combined with the PureLink RNA Mini Kit from Thermo Fisher (Cat #1283020). Post RNA isolation cDNA was synthesized using the iScript Select cDNA Synthesis Kit from BioRad using Oligo dt for Reverse Transcriptions (Cat #1708897). For each cDNA reaction 500 ng RNA was used.

HAO 3-4 and HAO 25-26 target message was quantified using digital droplet PCR (ddPCR). Target site specific assays and a GUSB housekeeper Taqman Assay available from Thermo Fisher (CAT #Mf04392669_g1) were employed. The HAO 25-26 message assay utilized primers P6, F7, and R8. The HAO 3-4 target message assay utilized primers F6, R7 and probe P5. Amplifications were multiplexed in a 20 uL reaction containing 1× ddPCR Supermix for Probes (no dUTP, BioRad), 250 nM of each probe, 900 nM of each primer, 5U of HindIII-HF, and 6 ul of the cDNA reaction. Droplets were generated using a QX100 droplet generator (BioRad). Cycling conditions were as follows: 1 cycle of 95° C. (2° C./s ramp) for 10 minutes, 44 cycles of 95° C. (1° C./s ramp) for 45 seconds, 60° C. (1° C./s ramp) for 45 seconds, 72 C (0.2° C./s ramp) for 2 minutes, 1 cycle of 98° C. for 10 minutes, 4° C. hold. Droplets were analyzed using a QX200 droplet reader (BioRad) and QuantaSoft analysis software (BioRad) was used to acquire and analyze data. HAO binding site assay levels were compared to GUSB levels to determine the ratio between the two assays. The ratio of HAO Binding site Assay/GUSB Assay in the controls were assumed to be in the realm of normal levels and normalized to 0 indicating no change in message for controls. All treated samples were normalized to the PBS group as 0% editing to quantify intact message loss.

```
Primer sets
F6: HAO 3-4 cDNA pr cons primer #3:
                                    (SEQ ID NO: 54)
TTCCCAGGGACTGACAGGCTC

R7: HAO 3-4/25-26 cDNA reverse primer 2:
                                    (SEQ ID NO: 55)
ATGCTCCCCCGGCTAATTTGTATCAATG

P5: 80 probe HAO 3-4 (BHQ):
                                    (SEQ ID NO: 56)
ACTTCCAAAGTCTATATATGAC

F7: HAO3-4 cDNA Pr. Cons. Primer #2 C2
                                    (SEQ ID NO: 57)
CCCCCGGCTAATTTGTATCAATGATTATGAAC

R8: HAO3-4/25-26 cDNA Reverse Primer:
                                    (SEQ ID NO: 58)
TCAACATCATGCCCGTTCCCAG

P6: HAO 25-26 cDNA Probe #4:
                                    (SEQ ID NO: 59)
TCCAGATGGAAGCTGTATC
```

2. Results

A. Functional Metabolic Response (Serum Glycolate)

Figure 10A:
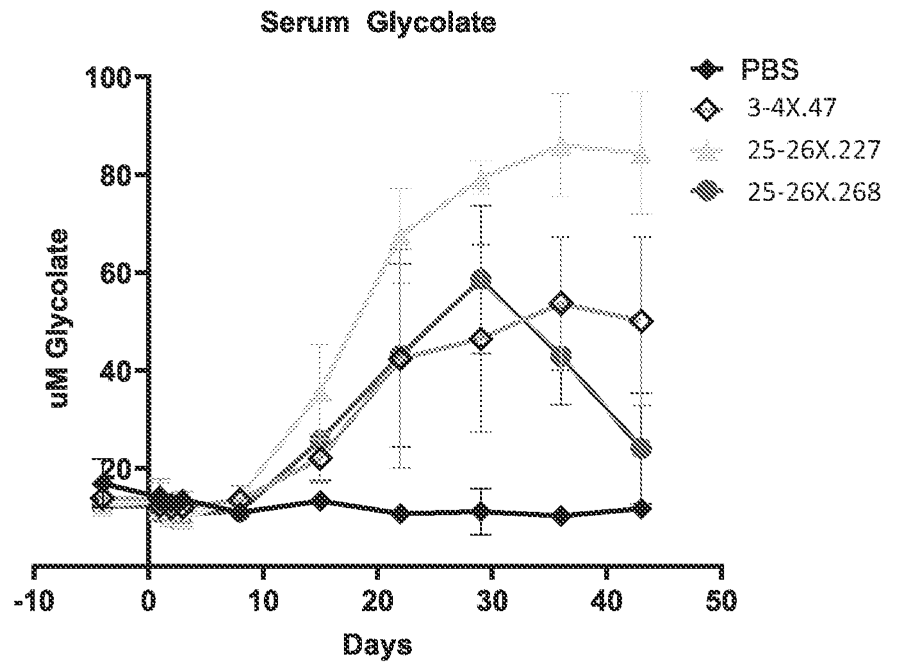
FIGS. 10A and 10B show changes in serum glycolate levels over time in non-human primates (NHPs) administered an AAV8 virus comprising a transgene encoding the HAO 25-26x.227, HAO 25-26x.268, or HAO 3-4x.47 meganucleases.
Figure 10B:
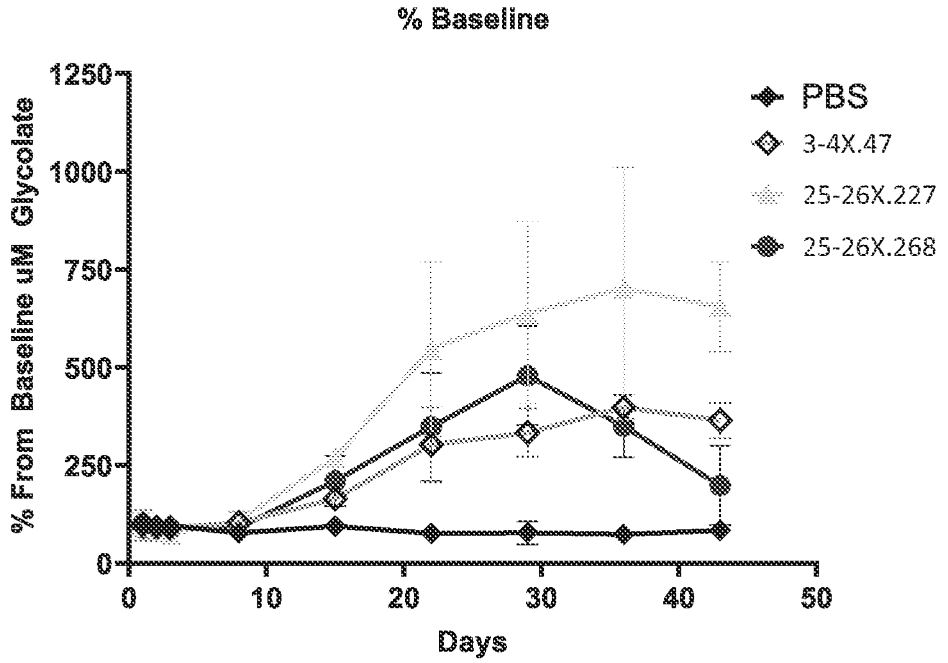
Figure 11A:
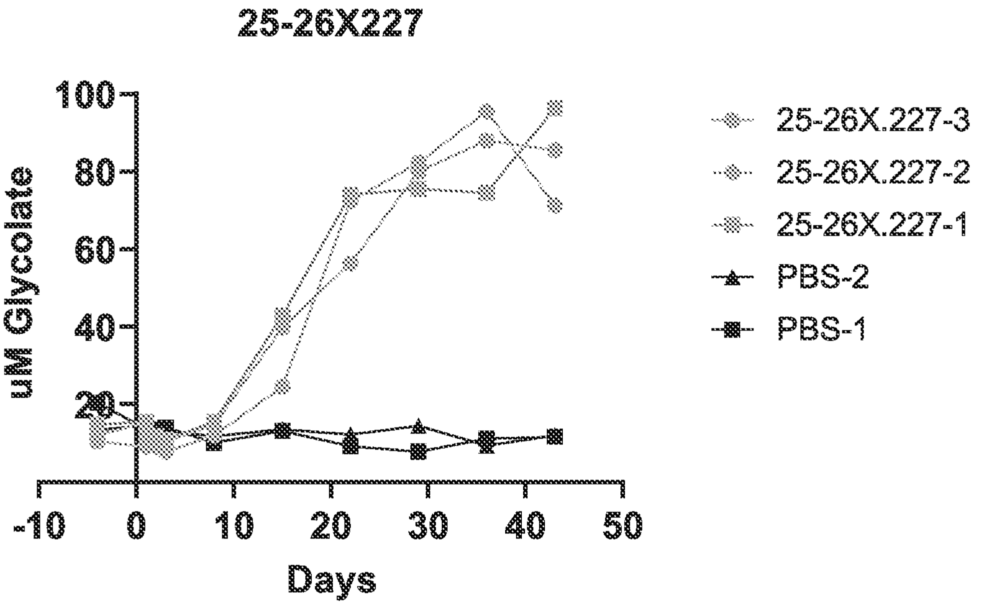
FIGS. 11A-11C show changes in serum glycolate levels over time in non-human primates (NHPs) administered an AAV8 virus comprising a transgene encoding the HAO 25-26x.227, HAO 25-26x.268, or HAO 3-4x.47 meganucleases.
Figure 11B:
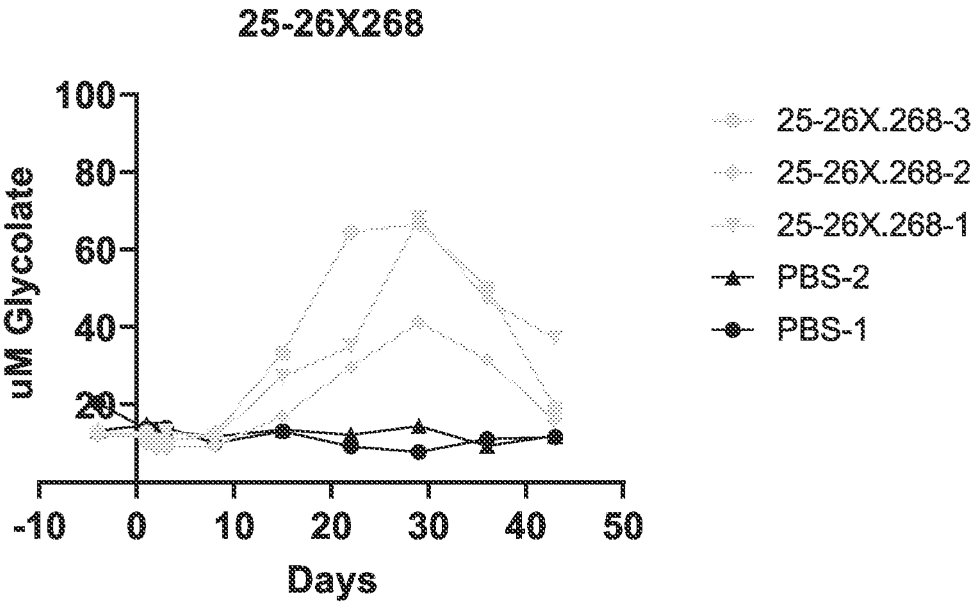
Figure 11C:
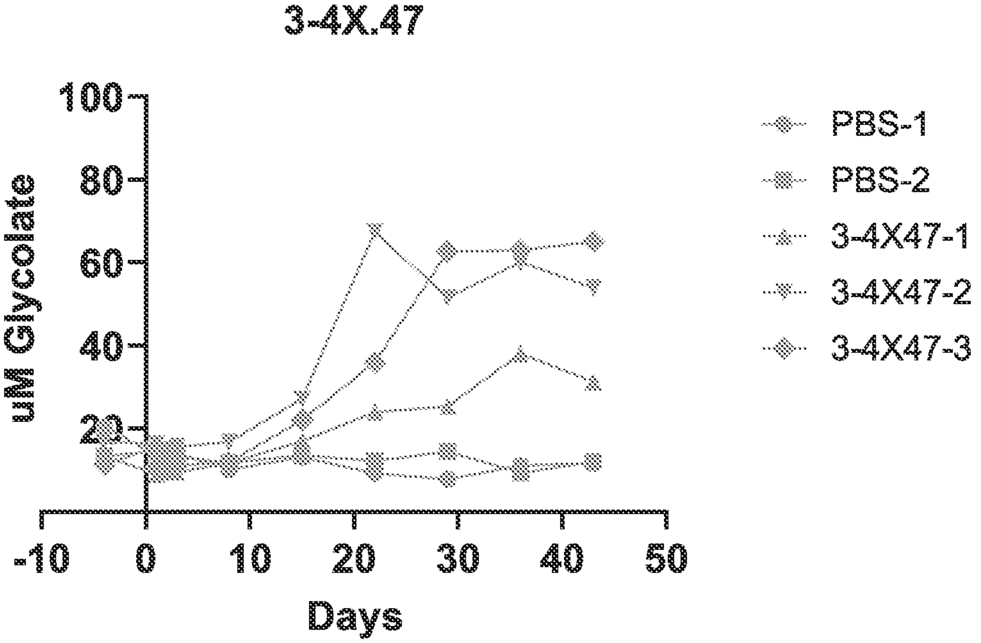

Serum glycolate was measured across the course of the study (FIGS. 10 and 11). Serum glycolate levels were not affected in the PBS groups, maintaining a constant level of approximately 15 μM across timepoints. An initial increase in serum glycolate levels was noted at day 15 for all meganuclease-treated groups. Serum glycolate for the HAO 25-26x.227 group increased to >80 μM at day 39 (FIG. 11A). Serum glycolate for the HAO 25-26x.268 group increased over time, peaked at approximately 60 μM at day 29, and then dropped to just above 20 μM at day 43 (FIG. 11B). Serum glycolate for the HAO 3-4x.47 group increased to >45 μM at day 43 (FIG. 11C). Serum glycolate levels across timepoints were normalized to the PBS groups to calculate percent increase above baseline for each treatment group. All treated groups had a >200% increase in serum glycolate, with HAO 25-26x.227 having increases over 700% (FIG. 10B).

B. Potency Indels in Liver

Figure 12A:
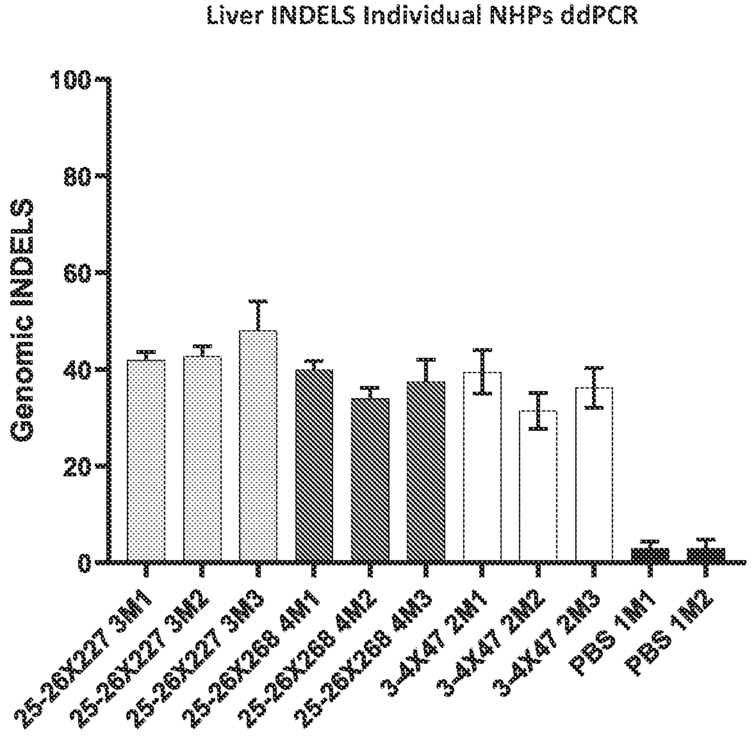
FIGS. 12A and 12B show genomic indels observed in the livers of NHPs observed by droplet digital PCR ("ddPCR").
Figure 12B:
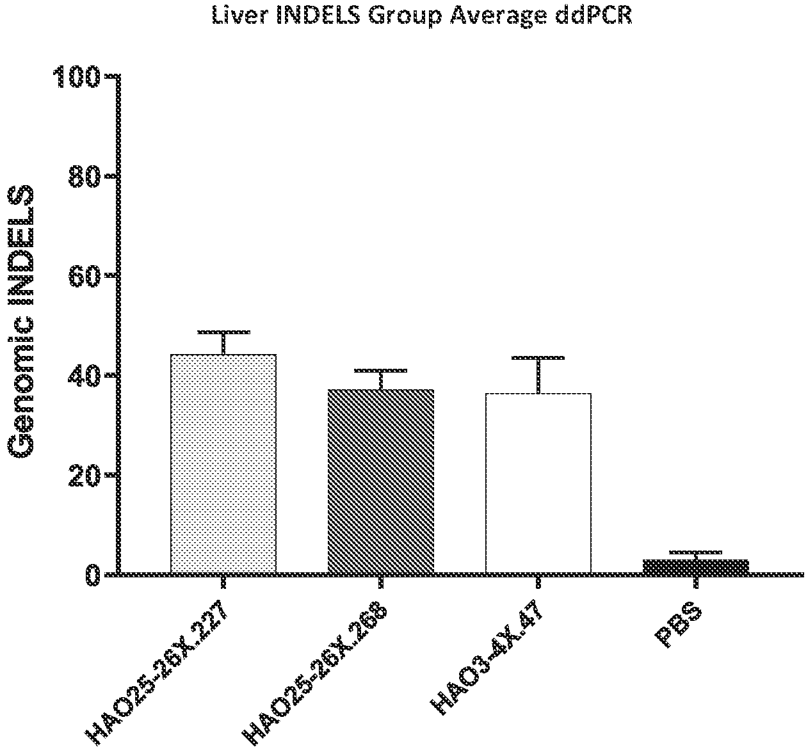

Indels at the HAO 25-26 and HAO 3-4 recognition sequences were quantified in liver tissue at necropsy. FIG. 12 shows the averaged indels observed for each animal and group. Percent editing was consistent across groups (FIG. 12A) with HAO 25-26x.227 averaging 44% indels, HAO 25-26x.268 averaging 37% indels, and HAO 3-4x.47 averaging 36% indels (FIG. 12B).

C. HAO1 Protein Knock Down in the Liver

Figure 13A:
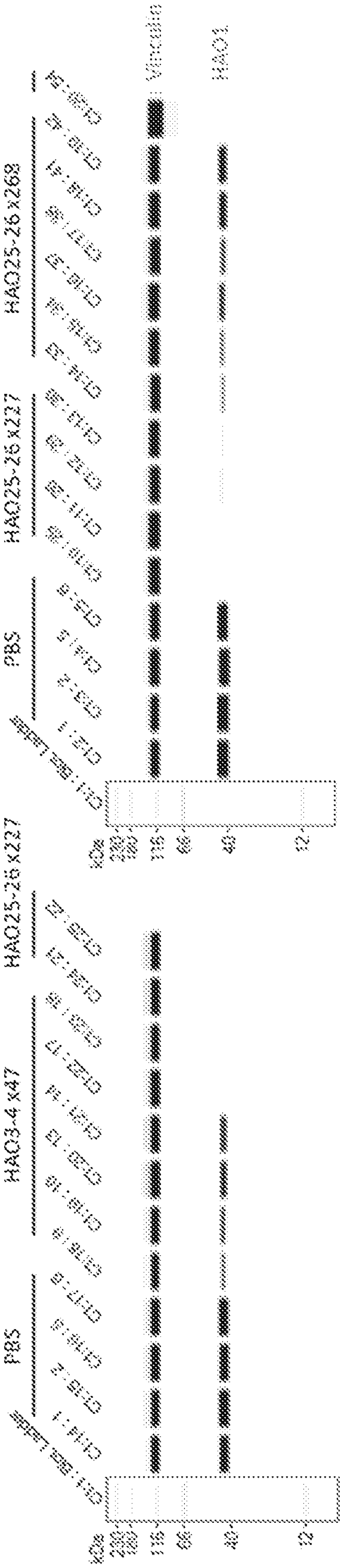
FIGS. 13A-13C show an analysis of liver samples by western blot (WES).
Figure 13B:
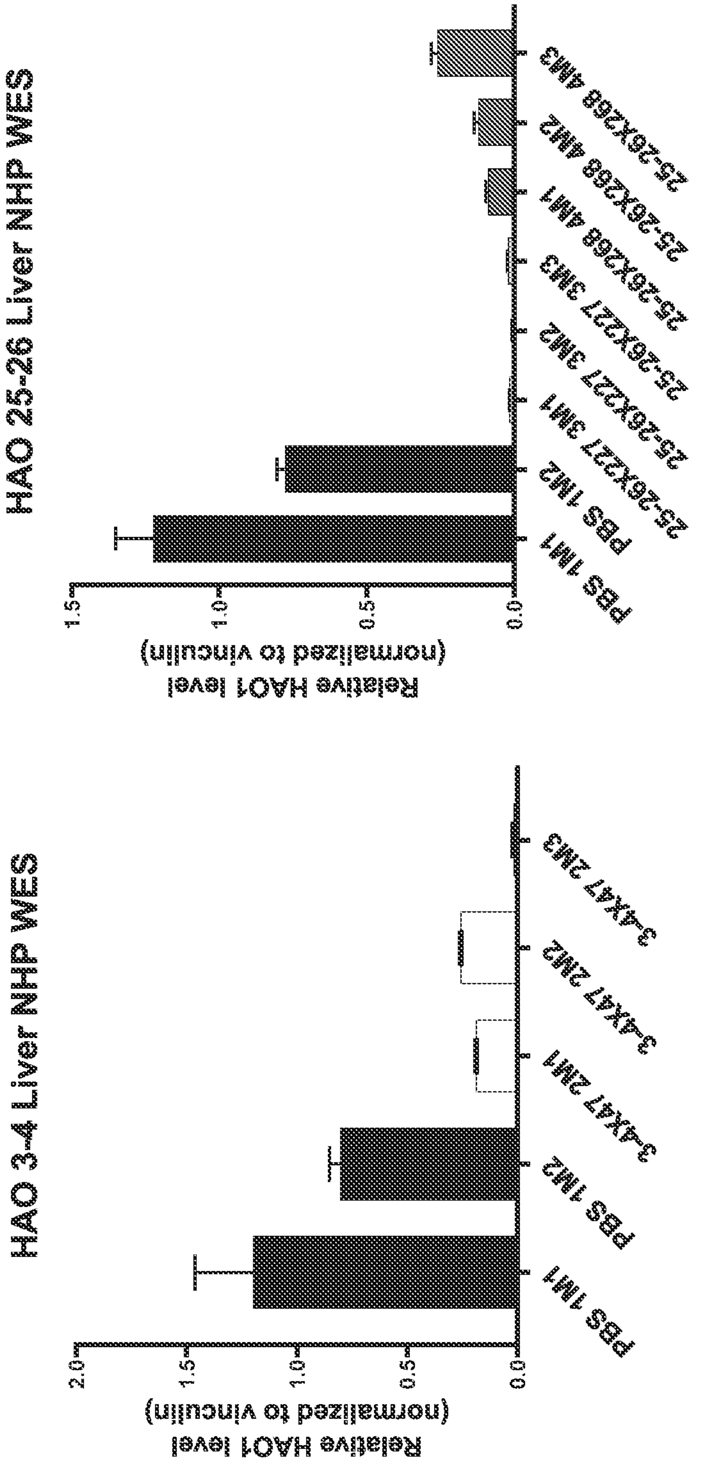
Figure 13C:
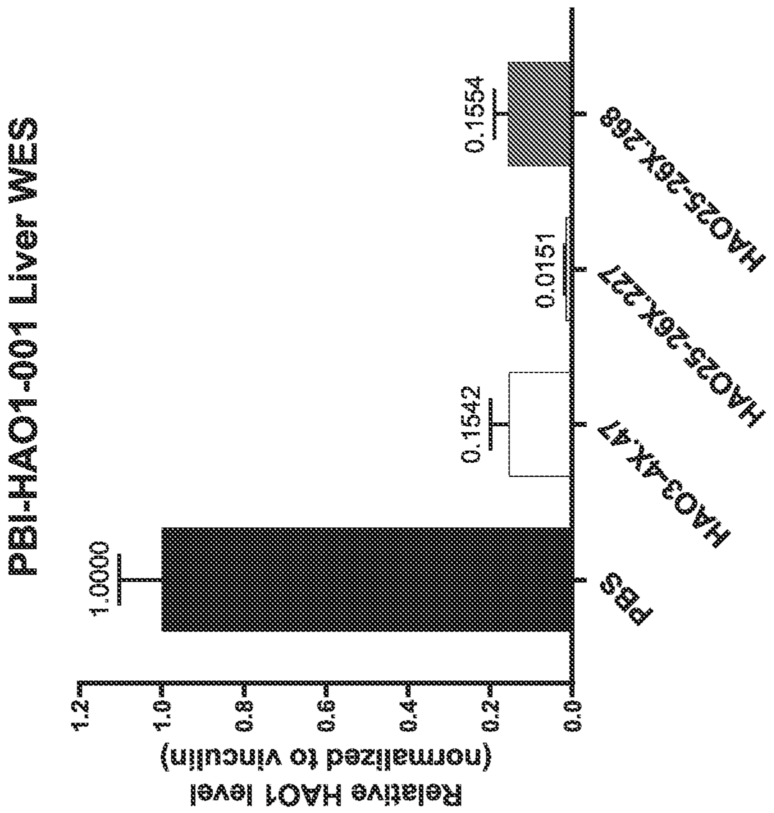

HAO1 protein knock down in was quantified using WES. FIG. 13A is a graphical representation of a digital western blot showing protein stained bands for both HAO1 protein and vinculin as a normalizer. HAO1 protein levels were consistent across two lobes of each NHP liver (FIG. 13B). HAO1 protein knock down in tissue treated with HAO 25-26x.227 was greater than 98% with HAO 25-26x.268 and HAO3-4x.47 achieving >85% knock down (FIG. 13C).

D. HAO1 Message Knockdown

Figure 14:
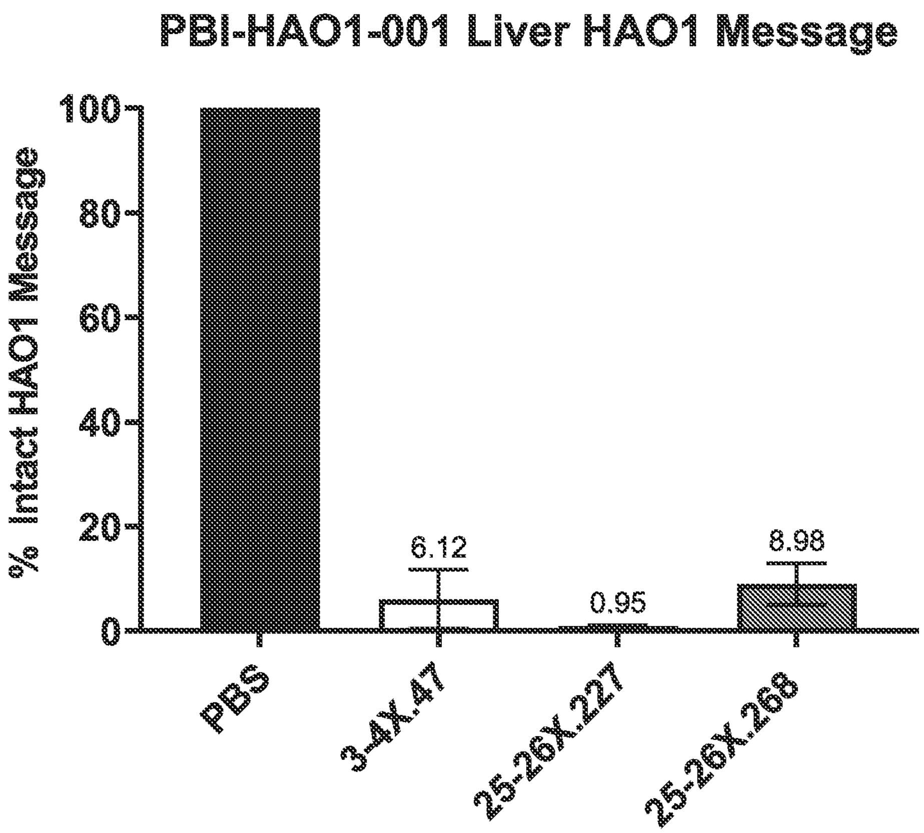
FIG. 14 provides an analysis of HAO1-encoding messenger RNA ("HAO1 message") in liver samples measured by ddPCR and shown relative to PBS-treated animals.

HAO1 message levels were measured and normalized to GUSB. The ratio of HAO1 target site Assay/GUSB Assay from control NHP's were compared to treated NHP's. HAO 3-4x.47 treated NHP's averaged 6.12% of HAO1 message levels of control NHP's. Message levels were 8.98% and 0.95% of untreated controls for NHP's treated with HAO 25-26x.268 and HAO 25-26x.227, respectively (FIG. 14).

3. Conclusions

A significant increase in glycolate was observed in the serum of all treated NHPs. While all three nucleases tested were effective for increasing serum glycolate levels, producing indels at their target sites, reducing HAO1 protein expression, and reducing HAO1 message, HAO 25-26x.227 produced the highest increase in serum glycolate over the duration of the study, peaking at >80 μM, the highest editing efficiency, and the most significant reduction in HAO1 protein and message levels in liver tissue. Overall, these studies demonstrated a pharmacological response to HAO1 knockout using HAO 25-26 specific meganucleases.

Example 5

Editing of the HAO 25-26 Recognition Sequence in a Reporter Cell Line

1. Methods and Materials

Additional HAO 25-26 meganucleases were optimized and selected based on the HAO 25-26x.227 and HAO 25-26x.268 meganucleases described in Examples 1-4. These experiments were designed to determine whether these optimized and selected meganucleases could bind and cleave the HAO 25-26 recognition sequence in mammalian cells using the CHO reporter cell assay described in Example 1. The transfected CHO cells were evaluated by flow cytometry at 2 days, 5 days, and 7 days post transfection to determine the percentage of GFP-positive cells compared to an untransfected negative control. Data obtained at each time point was used to generate the "activity index" for each HAO 25-26 meganuclease analyzed.

2. Results

Figure 15:
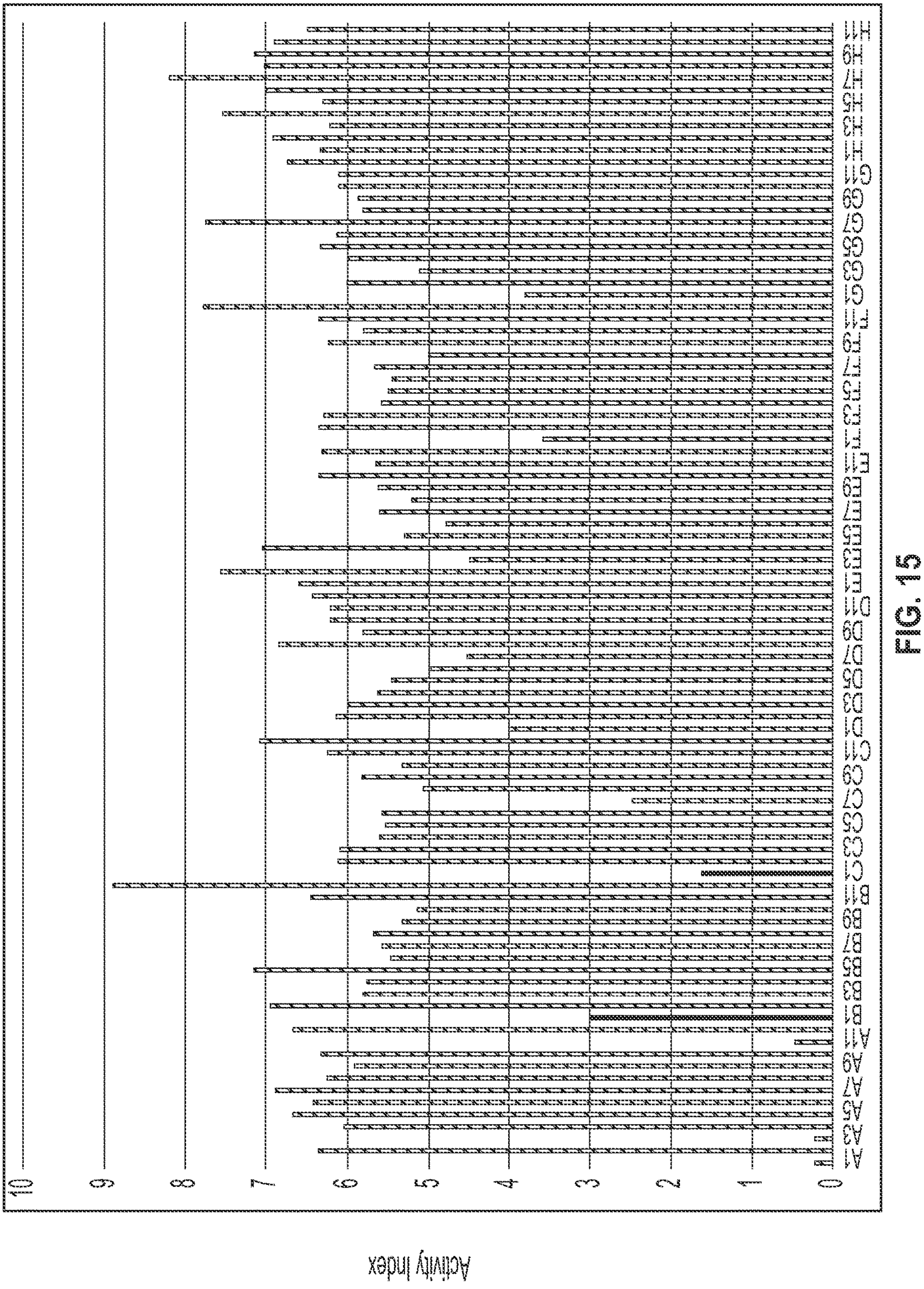
FIG. 15 provides an activity index of HAO 25-26 meganucleases evaluated in the CHO cell reporter assay.

The HAO 25-26x.227 meganuclease is shown in well C1 of FIG. 15. The positive control CHO-23/24 in well B1 exhibited a normalized activity index of 3. Many of the 93 HAO 25-26 meganucleases screened in this round of selections showed scores higher than the CHO-23/24 control and the HAO 25-26x.227 meganuclease. The HAO 25-26L.550 meganuclease (SEQ ID NO: 7) (well B12) had a normalized index value more than 3× the value of the HAO 25-26x.227 meganuclease (in well C1) indicating a substantial increase in activity without a substantial increase in toxicity.

3. Conclusions

This assay allowed for the identification of a further optimized HAO 25-26 meganuclease for subsequent analysis, based on its activity index in mammalian cells.

Example 6

Editing of the HAO 25-26 Recognition Sequence in a Human Cell Line

1. Methods and Materials

This experiment was conducted using an in vitro cell-based system to evaluate the editing efficiency of the HAO 25-26L.550 meganuclease by digital PCR using an indel detection assay. In this study, mRNA encoding the HAO 25-26L.550 meganuclease or the HAO 25-26x.268 meganuclease were electroporated into cells Hep3B cells, which were then analyzed over a time course study by ddPCR as described in Example 2.

2. Results

Figure 16A:
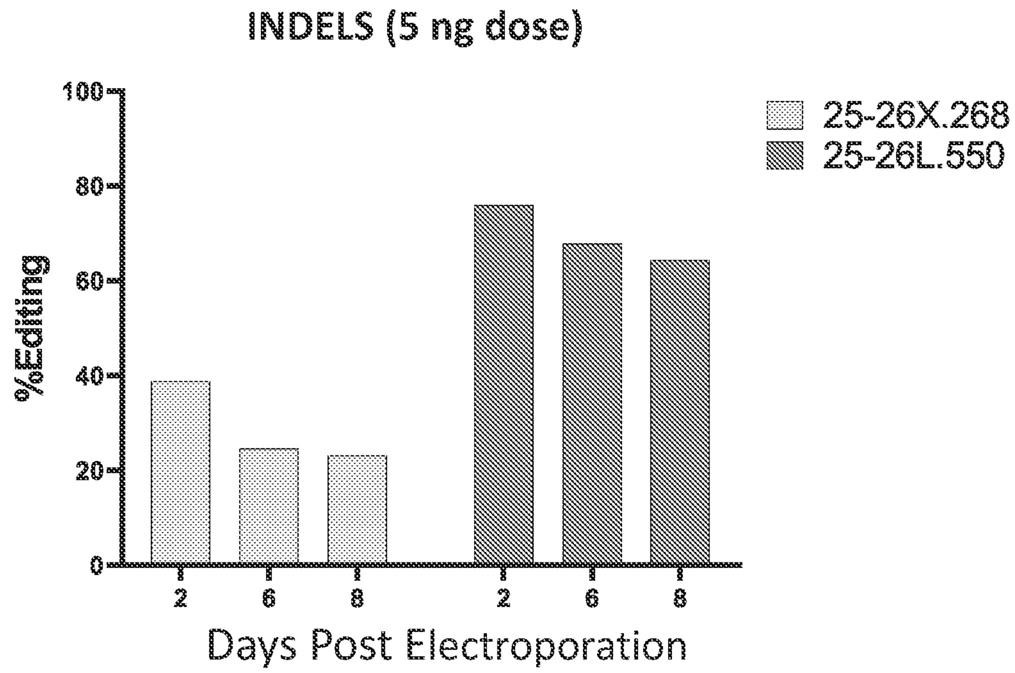
FIGS. 16A-16C show the frequency of indel generation in Hep3B cells over time following introduction of low and high doses of mRNA encoding the HAO 25-26x.268 and HAO 25-26L.550 meganucleases.
Figure 16B:
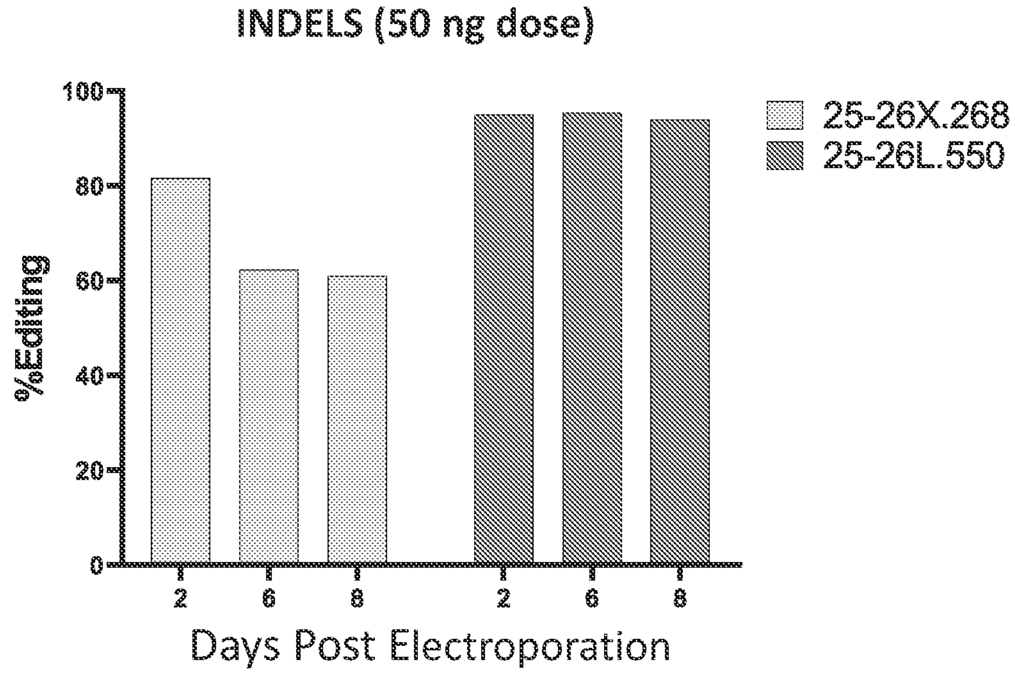

The formation of indels was measured by ddPCR across timepoints. Indels in Hep3B cells using the low dose of mRNA (FIG. 16A) showed that HAO 25-26L.550 produced indels of >75% at day 2 and >60% at day 8. By comparison, HAO 25-26x.268 produced indels of >35% at day 2 to >20% at day 8. Indels produced using the high dose of mRNA (FIG. 16B) were >90% for HAO 25-26L.550, and >60% for HAO 25-26x.268 across all time points.

Figure 16C:
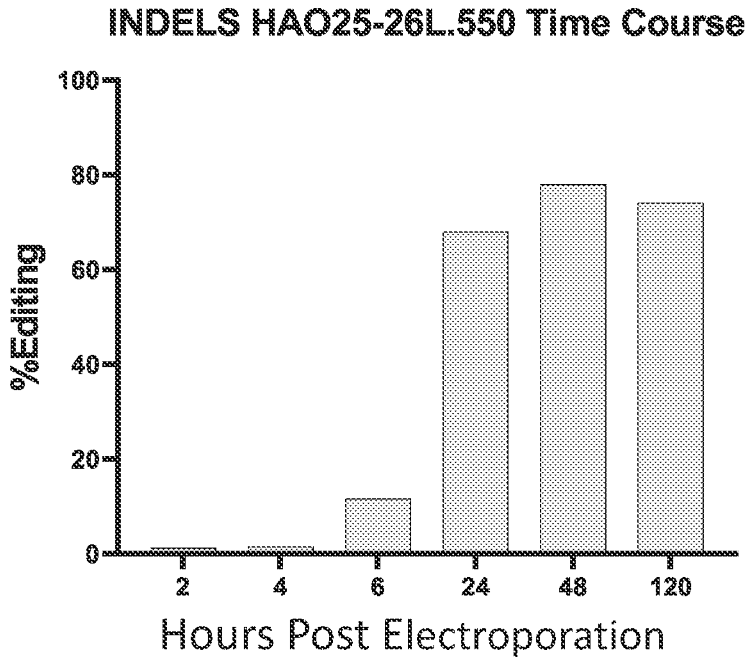

Looking at the time course of indel formation using the HAO 25-26L.550 meganuclease, editing activity was not detectable until 6 hours post mRNA electroporation with >5% editing, with indels at 68% at 24 hours, and greater than 70% at 48 and 120 hours post electroporation (FIG. 16C).

3. Conclusions

The HAO 25-26L.550 meganuclease was directly compared to the HAO 25-26x.268 meganuclease in Hep3B cells for their ability to generate indels over time. The HAO 25-26L.550 meganuclease was substantially more potent than the HAO 25-26x.268 meganuclease in the high and low mRNA doses, and showed editing by 6 hours post electroporation of mRNA.

Example 7

Editing of the HAO 25-26 Recognition Sequence in a Reporter Cell Line

1. Methods and Materials

Additional HAO 25-26 meganucleases were optimized and selected based on the HAO 25-26L.550 meganuclease described in Examples 5 and 6. These experiments were designed to determine whether these optimized and selected meganucleases could bind and cleave the HAO 25-26 recognition sequence in mammalian cells using the CHO reporter cell assay described in Example 1 and Example 5. The transfected CHO cells were evaluated by flow cytometry at 2 days, 5 days, and 7 days post transfection to determine the percentage of GFP-positive cells compared to an untransfected negative control. Data obtained at each time point was used to generate the "activity index" for each HAO 25-26 meganuclease analyzed.

2. Results

Figure 17:
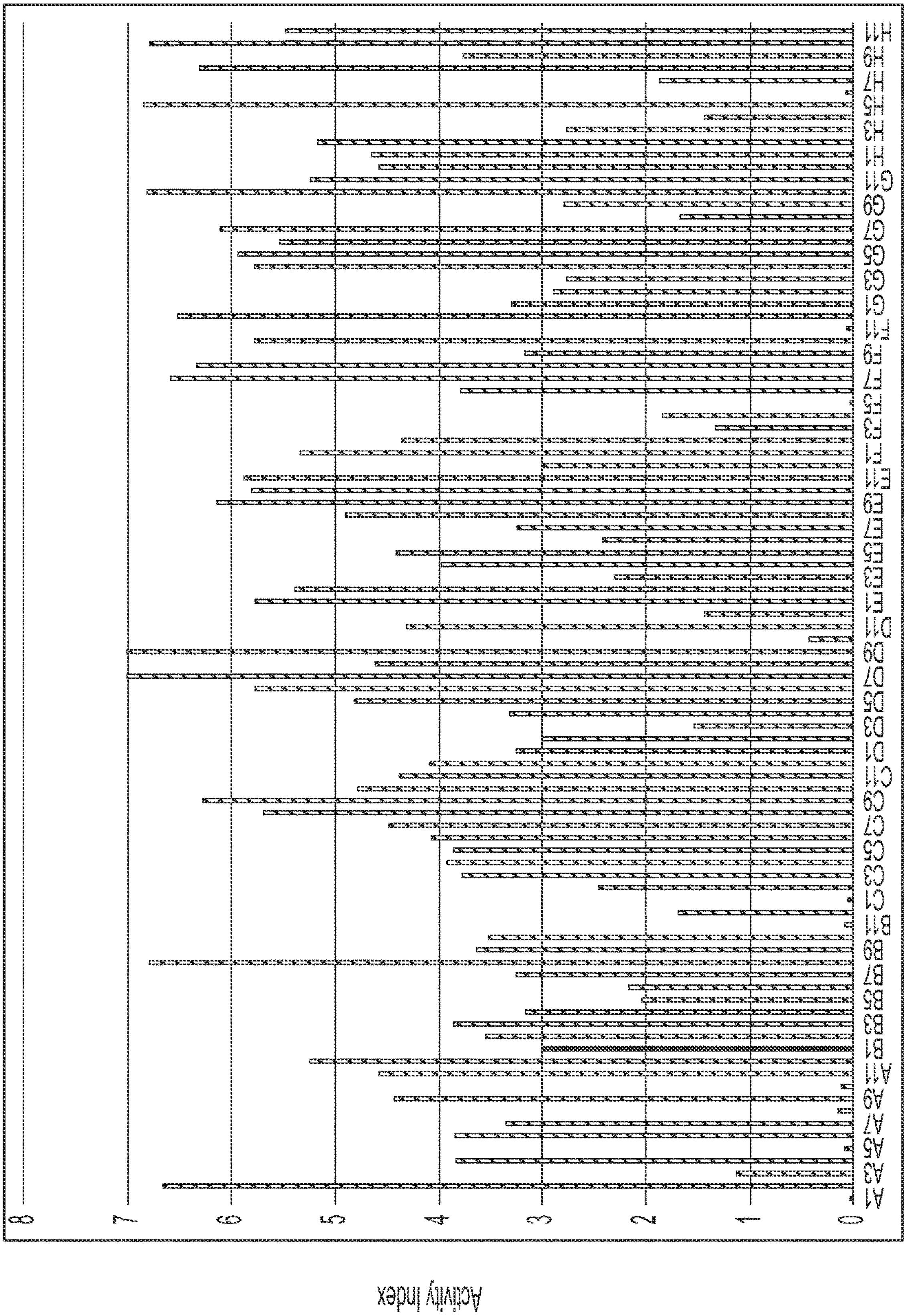
FIG. 17 shows the activity index of HAO 25-26 meganucleases evaluated in the CHO cell reporter assay.

In the results shown in FIG. 17, the positive control CHO-23/24 is in well B1 with a normalized activity index of 3. Out of 93 HAO 25-26 meganucleases screened, more than half produced higher scores than the CHO-23/24 control. The HAO 25-26L.907 (SEQ ID NO: 6) (well G10) and HAO 25-26L.908 (SEQ ID NO: 5) (well H10) meganucleases both showed scores more than 2× that of the CHO-23/24 control.

3. Conclusions

This assay allowed for the identification of further optimized HAO 25-26 meganucleases for subsequent analysis, based on their activity index in mammalian cells.

Example 8

Editing of the HAO 25-26 Recognition Sequence in a Human Cell Line

1. Methods and Materials

These experiments were conducted using in vitro cell-based systems to evaluate the editing efficiencies of the HAO 25-26L.907 and HAO 25-26L.908 meganucleases by digital PCR using an indel detection assay. In these studies, low (5 ng) and high (50 ng) doses of mRNA encoding the HAO 25-26L.907 and HAO 25-26L.908 meganucleases, or the HAO 25-26L.550 meganuclease, were electroporated into Hep3B cells and analyzed on days 2, 6, and 8 by ddPCR as described in Example 2.

2. Results

Figure 18A:
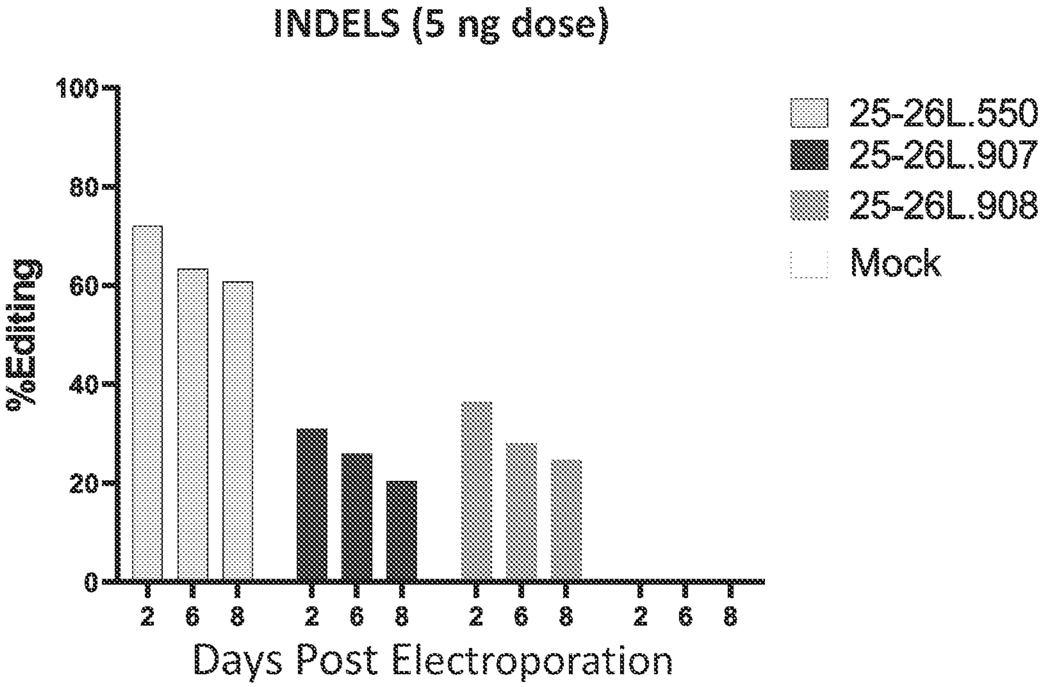
FIGS. 18A and 18B shows the frequency of indel generation in Hep3B cells over time following introduction of low and high doses of mRNA encoding the HAO 25-26L.550, HAO 25-26L.907, and HAO 25-26L.908 meganucleases.
Figure 18B:
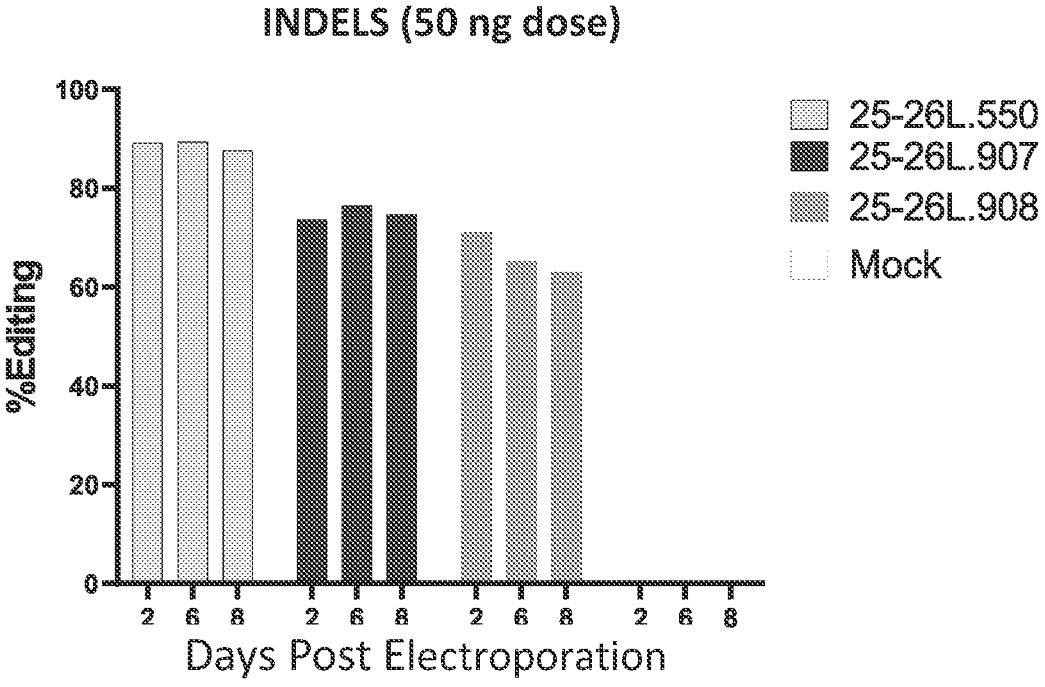

As shown in FIG. 18, the low mRNA dose of HAO 25-26L.550 generated indels from 60% to >70% across the 8-day experiment. By comparison, the low mRNA dose of the HAO 25-26L.907 and HAO 25-26L.908 meganucleases produced indels ranging from >20% to >35% (FIG. 18A). Using the high dose of mRNA, the HAO 25-26L.907 and HAO 25-26L.908 meganucleases produced indels of >60% over the course of the experiment, whereas the HAO 25-26L.550 meganuclease generated indels of >80% over the course of the experiment (FIG. 18B).

3. Conclusions

These experiments demonstrated that the HAO 25-26L.907 and HAO 25-26L.908 meganucleases effectively produced indels at their target site in Hep3B cells using low and high doses of mRNA, although the HAO 25-26L.550 meganuclease was more potent in vitro. However, the activity of the HAO25-26L.907 and HAO 25-26L.908 meganucleases was sufficient to move these nucleases into further characterization.

Example 9

Editing of the HAO 25-26 Recognition Sequence in a Human Cell Line

1. Methods

The HAO 25-26L.908 was further optimized for specificity and potency. Among the hundreds of meganucleases generated, the HAO 25-26L.1128 (SEQ ID NO: 10) and HAO 25-26L.1434 (SEQ ID NO: 11) meganucleases were identified as potential candidates for further evaluation. These experiments were conducted using in vitro cell-based systems to evaluate the editing efficiencies of the HAO 25-26L.1128 and HAO 25-26L.1434 meganucleases by digital PCR using an indel detection assay. In these studies, low (5 ng) doses of mRNA encoding HAO 25-26L.1128 and HAO 25-26L.1434 meganucleases were electroporated into Hep3B cells and analyzed on days 2, 4, and 7 by ddPCR as described in Example 2. In addition to these nucleases, the HAO 25-26x.227 and HAO 25-26L.908 meganucleases were included in the experiments as a compatator of previous nuclease generations.

2. Results

Figure 19:
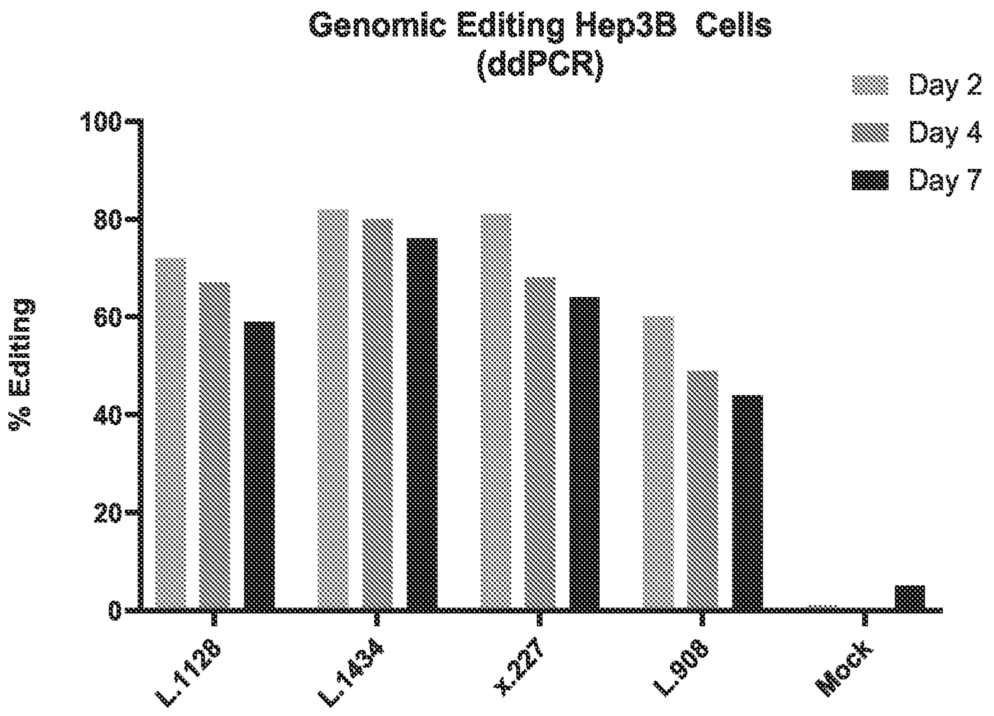
FIG. 19 shows editing efficiencies of the HAO 25-26L.907 and HAO 25-26L.908 meganucleases in Hep3B cells by digital PCR using an indel detection assay.

As shown in FIG. 19, the low mRNA dose of HAO 25-26L.1128 and HAO 25-26L.1434 generated indels from 50% to >80% across the 7-day experiment. By comparison, the low mRNA dose of the earlier generation HAO 25-26x.227 generated INDELS ranging from 66% to 81% and HAO 25-26L.908 generated INDELS ranging from 44% to 60%.

3. Conclusions

These experiments demonstrated that the HAO 25-26L.1128 and HAO 25-26L.1434 meganucleases effectively produced indels at their target site in Hep3B cells using low doses of mRNA. Furthermore the HAO 25-26L.1128 and HAO 25-26L.1434 meganucleases were shown to have a potency comparable with earlier generations of HAO 25-26 meganucleses and were selected to move into further chacterization.

Example 10

1. Methods

These experiments were conducted using in vitro cell-based systems to evaluate the editing efficiencies of different HAO 25-26 meganucleases for potency across an mRNA dose range by digital PCR using an indel detection assay. In these studies, mRNA encoding the HAO 25-26L.1128, HAO 25-26L.1434, and HAO 25-26x.227 meganucleases were electroporated into Hep3B cells at 250, 100, 50, 10, 5, and 2 ng doses using the Lonza Amaxa 4D system. Each meganuclease included an N-terminal SV40 NLS as previously discussed. Cells were collected at 6 days post electroporation for gDNA preparation and characterized by ddPCR as described in Example 2.

2. Results

Figure 20:
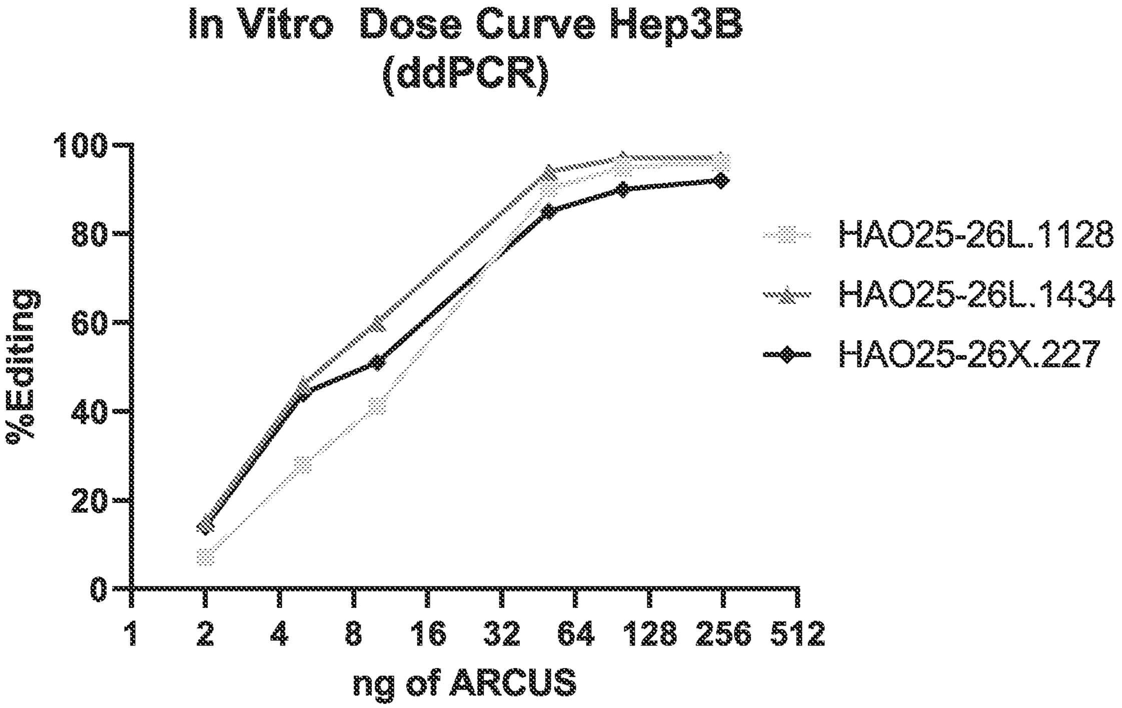
FIG. 20 shows editing efficiencies of HAO 25-26 meganucleases for potency across an mRNA dose range by digital PCR using an indel detection assay in Hep3B cells.

A dose titration comparing editing activity in Hep3B cells across multiple doses of mRNA was used to compare potency between the HAO 25-26L.1128, HAO 25-26L.1434, and HAO 25-26x.227 meganucleases. As shown in FIG. 20, editing for HAO 25-26x.227 ranged from 92% at the higher mRNA doses to 14% at the lowest mRNA dose. Editing for HAO 25-26L.1128 ranged from 96% at the higher mRNA doses to 7% at the lowest mRNA dose. Editing for HAO 25-26L.1434 ranged from 97% at the higher mRNA doses to 15% at the lowest dose of mRNA.

3. Conclusions

These studies demonstrated that all three of the tested meganucleases exhibited a dose-dependent increase in the generation of indels in Hep3B cells. HOA 25-26L.1434 was the most potent across all mRNA doses, with HAO 25-26L.1148 showing slightly less potency than HAO 25-26x.227, but in range sufficient to move deeper into characterization studies.

Example 11

Evaluation of Additional HAO 25-26 Meganucleases in Non-Human Primates

1. Methods and Materials

An efficacy study was conducted to evaluate the potency and functional metabolic response in non-human primates (NHPs), cynomolgus macaque, with additional HAO 25-26 meganucleases that target the HAO 25-26 recognition sequence in the HAO1 gene, which is conserved across NHPs and humans.

In this study, animals were administered PBS as a control, or a transgene encoding an HAO 25-26 meganuclease, either HAO 25-26L.1128 or HAO 25-26L.1434 at two different dosage levels as shown in Table 4 below.

TABLE 4

Experimental Design Scheme

| Group | Treatment | Number of NHP | Dose Conc. (VG/mL) | Dose Volume (VG/kg) | Prednisolone Dose Level (mg/kg/day) |
|---|---|---|---|---|---|
| 1 | PBS | 2 | 0 | 0 | 1 |
| 2 | AAV8-HAO25-26L.1128 | 3 | $2 \times 10^{12}$ | $1 \times 10^{13}$ | 1 |
| 3 | AAV8-HAO25-26L.1128 | 3 | $6 \times 10^{12}$ | $3 \times 10^{13}$ | 1 |
| 4 | AAV8-HAO25-26L.1434 | 3 | $2 \times 10^{12}$ | $1 \times 10^{13}$ | 1 |
| 5 | AAV8-HAO25- | 3 | $6 \times 10^{12}$ | $3 \times 10^{13}$ | 1 |

Daily administration of anti-inflammatory drug prednisolone (1 mg/kg) started at one week prior to dose administration through scheduled termination. On the day of dose administration, animals were administered the test article/vehicle once via intravenous (IV) infusion over a 2-minute time-period followed by a 6 mL flush of saline. Restraint, temporary catheter placement and dosing procedures were completed per SRC SOPs. Individual dose volume was calculated on each individual animal's most recent body weight.

The test article was administered at either $2\times10^{12}$ or $6\times10^{12}$ viral genomes (VG)/mL and intravenously (IV) infused over 2 minutes, for a final dose of either $1\times10^{13}$ or $3\times10^{13}$ VG/kg.

The study duration assessed tolerability, potency and functional metabolic response from day 1 to day 43. Mortality/Moribundity was checked twice daily, while hematology, coagulation, serum chemistry, serum aldolase, and serum glycolate levels were analyzed at acclimation, pre-dose, and days 0 (prior to dosing of the test article) 3, 8, 15, 22, 29, 43, 57, and 71 days post administration of the test article, and were compared to PBS group. Additional serum was collected and frozen. Overall potency was determined based on percent indels at time of necropsy, while tolerability was determined based on cytokine and complement induction levels and serum chemistry test.

A total of 1.0 mL of whole blood was collected via direct venipuncture of the femoral vein (or other appropriate vessel). Blood samples were placed into tubes without anticoagulant and allowed to clot samples were centrifugated within 1 hr. The serum was harvested, placed into prelabeled cryovials, and temporarily stored on dry ice or frozen (−50 to −100° C.). Serum was collected for the following timepoints: day −8, days 0 (prior to test article dosing), 3, 8, 15, 22, 29, 43, 57, 71, and 92. Serum glycolate levels, were determined as described in the serum glycolate assay of Example 4.

Indel formation, HAO1 protein and message levels will be determine as described in Example 4 for the HAO 25-26 nucleases following animal necropsy.

2. Results

Figure 22A:
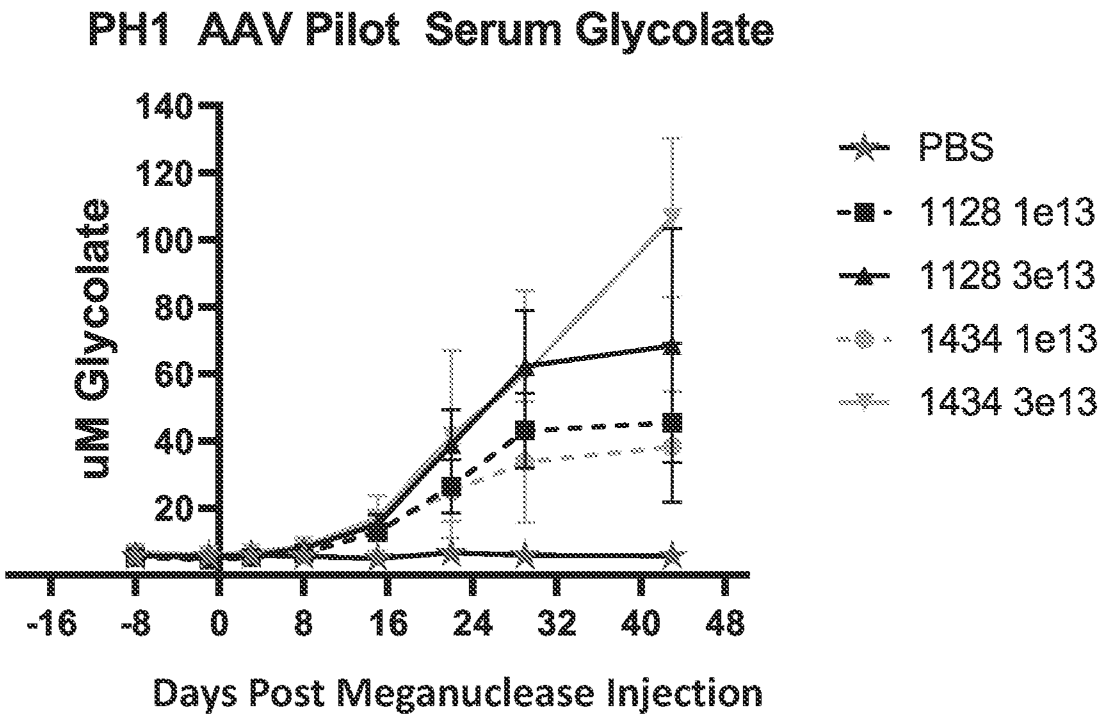
FIG. 22A shows changes in serum glycolate levels in μM over time in non-human primates (NHPs) administered an AAV8 virus comprising a transgene encoding the HAO 25-26L.1128 and HAO 25-26L.1434 engineered meganucleases at a dosage of 1e13 vg/kg or 3e13 vg/kg or mice treated with PBS up to day 43.
Figure 22B:
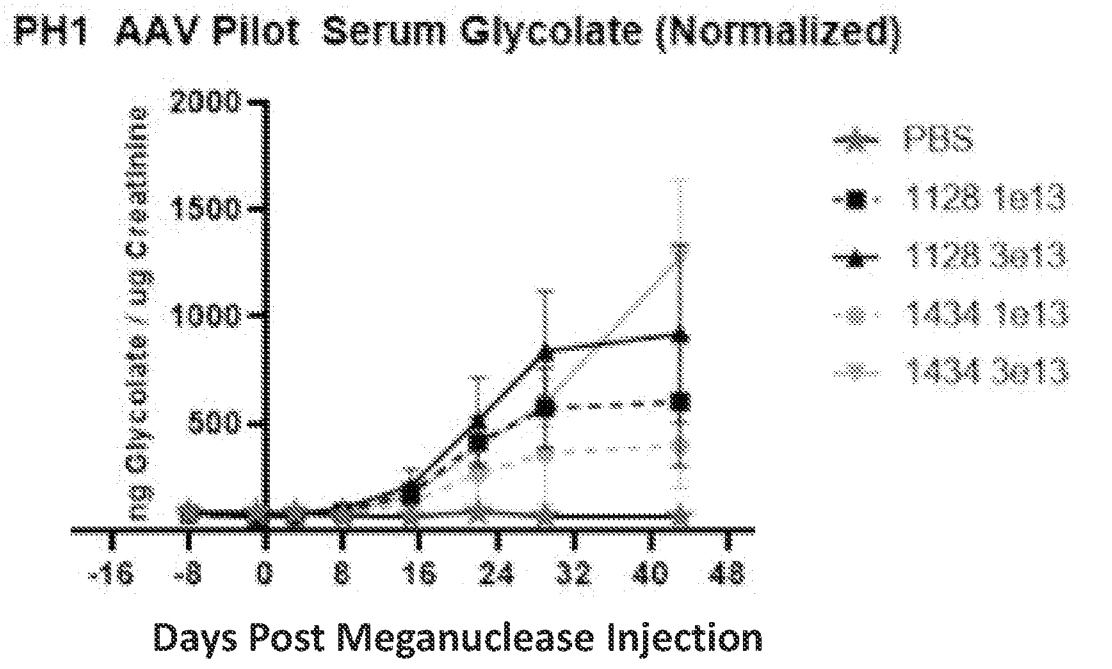
FIG. 22B shows serum glycolate levels as a percentage from baseline levels.

Serum glycolate was measured across the course of the study to date (FIG. 22). Serum glycolate levels were not affected in the PBS groups up to day 43, maintaining a constant level of approximately across timepoints. An initial increase in serum glycolate levels was noted at day 15 for all meganuclease-treated groups. Serum glycolate for the HAO 25-26L.1128 group increased to about 40-45 μM at day 43 at a low dose of 1e13 and about 70 μM at a high dose of 3e13 (FIG. 22). Serum glycolate levels for the HAO 25-26L.1434 nucleases at both dosages was similar to the HAO 25-26L.1128 nucleases. At Day 43 the high dose of the HAO 25-26L.1434 nuclease showed serum glycolate levels of near 105 to 110 μM.

3. Conclusions

A significant increase in glycolate was observed in the serum of all treated NHPs. The increase in dose amount lead to a concomitant increase in serum glycolate levels. Overall, these studies further demonstrated a pharmacological response to HAO1 knockout using HAO 25-26 specific meganucleases.

Example 12

Off-Target Analysis of HAO 25-26 Meganucleases by Oligo Capture

1. Methods

Specificity of the HAO 25-26x.227, HAO 25-26L.1128, and HAO 25-26L.1434 meganucleases was analyzed using an oligo capture assay in order to determine changes in the off targeting profile after successive generations of meganuclease optimization.

This is a cell-based, in vitro assay that relies on the integration of a synthetic oligonucleotide (oligo) cassette at double-strand breaks within the genome. Using the oligo as an anchor, genomic DNA to either side of the integration site can be amplified, sequenced, and mapped. This allows for a minimally biased assessment of potential off-target editing sites of the nuclease. This technique was adapted from GuideSeq (Tsai et al. (2015) *Nat. Biotech.* 33:187-97) with specific modification to increase sensitivity and accommodate the 3' complementary overhangs induced by the meganucleases. The oligo capture analysis software is sequence agnostic. That is, no a priori assumptions are made regarding which DNA sequences the nuclease is capable of cutting. In the oligo capture assay, cells are transfected with nuclease mRNA and double-stranded DNA oligonucleotides. After 2 days, the cellular genomic DNA was isolated and sheared into smaller sizes. An oligonucleotide adapter was ligated to the sheared DNA and polymerase chain reaction was used to amplify any DNA pieces that contain an adapter at one end and the captured oligonucleotide at the other end. The amplified DNA was purified, and sequencing libraries were prepared and sequenced. The data were filtered and analyzed for valid sites that captured an oligonucleotide to identify potential off-target sites. The sequence reads were aligned to a reference genome, and grouped sequences within thousand-base pair windows scanned for a potential meganuclease cleavage site. HEK293 cells were transfected with 2 μg of mRNA encoding HAO 25-26 nucleases at round 1 (i.e., HAO 25-26x.227) and round 6 (i.e., HAO 25-26L.1128 and HAO 25-26L.1434) of meganuclease optimization, and gDNA was isolated and processed as described in previous examples at 48 hours post-transfection.

2. Results

Figure 21:
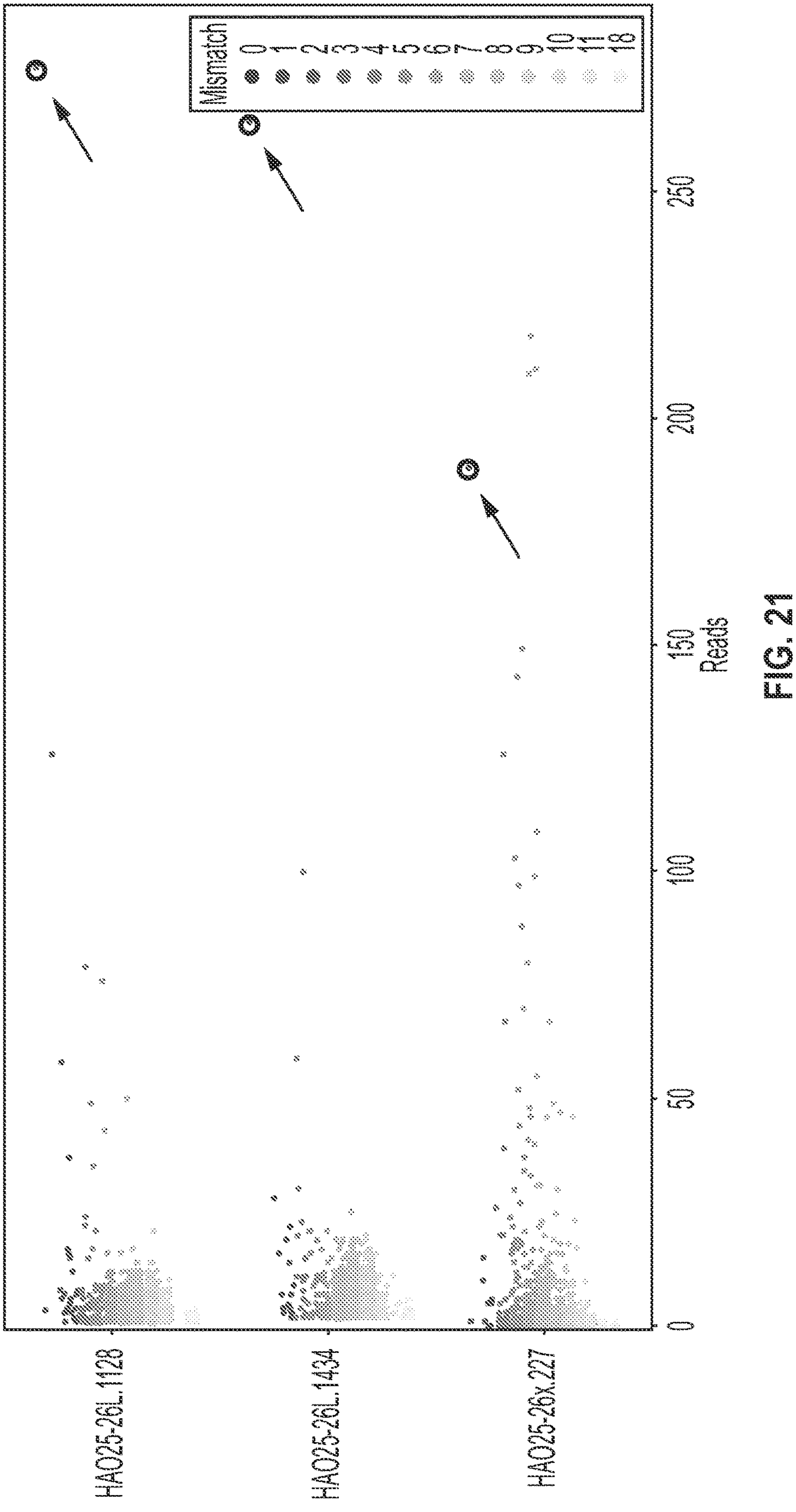
FIG. 21 shows oligonucleotide (oligo) capture data for the HAO 25-26x.227, HAO 25-26L.1128, and HAO 25-26L.1434 meganucleases 48 hours after mRNA transfection. Dot clusters toward the left of the graph represent low read counts, and dot clusters toward the right of the graph represent high read counts.

As shown in the oligo capture data shown in FIG. 21, each off-target site generated by each HAO 25-26 meganuclease in HEK293 cells is plotted based on the number of unique sequence reads for a probe oligo being captured at that site with the dot cluster on the left representing low read counts and dots to the right representing high read counts. The specificity of the HAO 25-26 meganucleases can be judged by how many intermediate sites are found in the middle region of the graph and how low their read counts are. Fewer dots correlate to fewer detected potential off-target sites overall, and dots closer to the left correlate to lower read counts and less confidence that they are legitimate off-targets. Sites with more mismatches compared to the target site are also less likely to be legitimate off-targets and are indicated by lighter shaded spots. For highly specific nucleases, the intended HAO target site should have the highest read count, which is the case for both HAO 25-26L.1128 and HAO 25-26L.1434 and are indicated by dots within circles (and indicated with arrows).

3. Conclusions

Meganuclease specificity for the HAO 25-26 target site increased between the initial nuclease and the sixth optimization round. Both the HAO 25-26L.1128 and HAO 25-26L.1434 meganucleases had a specificity profile that warranted characterizing targeted off-targets.

Example 13

Editing of HAO 25-26 Recognition Sequence in Human Cell Lines Using Improved mRNA Encoding the Engineered HAO 25-26 Meganucleases 1. Methods and Materials These studies were conducted using in vitro cell-based systems to evaluate editing efficiencies of different HAO 25-26 meganucleases by digital PCR using an indel detection assay.

In these experiments, improved mRNA was developed utilizing a different combinations of 5' and 3' UTRs, which was discovered to increase mRNA persistence and protein expression levels. This experiment was conducted to determine if such an mRNA would also lead to increased indel % in HepG2 cells.

The unmodified mRNA from 5' to 3' includes a 5' human HBA2 UTR (SEQ ID NO: 60), a sequence encoding an unmodified 10 amino acid N terminal SV40 NLS (amino acid sequence set forth in SEQ ID NO: 37 and nucleic acid sequence set forth in SEQ ID NO: 38), a sequence encoding the HAO 25-26L.1128 meganuclease (amino acid sequence set forth in SEQ ID NO: 10 and nucleic acid sequence set forth in SEQ ID NO: 31) or HAO 25-26L.1434 meganuclease (amino acid sequence set forth in SEQ ID NO: 11 and nucleic acid sequence set forth in SEQ ID NO: 32), a 3' WPRE UTR (SEQ ID NO: 61), and a 140 base pair poly A tail. The coding sequence for the 10 amino acid N terminal SV40 NLS comprises an unmodified coding sequence for a 7 amino acid minimal SV40 NLS sequence (amino acid sequence set forth in SEQ ID NO: 35 and nucleic acid sequence set forth in SEQ ID NO: 36) flanked by a methionine and an alanine residue at the 5' end and a histidine residue at the 3' end.

The improved mRNA from 5' to 3' includes, a 5' modified human ALB UTR (SEQ ID NO: 62), a modified Kozak sequence (GCCACCATGGC; SEQ ID NO: 69) which overlaps the 3' end of the ALB UTR and the 5' end of a sequence encoding an NLS, a sequence encoding a codon optimized 10 amino acid N terminal SV40 NLS (amino acid sequence set forth in SEQ ID NO: 37 and codon optimized nucleic acid sequence set forth in SEQ ID NO: 70), a codon optimized coding sequence encoding the HAO 25-26L.1128 meganuclease (amino acid sequence set forth in SEQ ID NO: 10 and codon optimized nucleic acid sequence set forth in SEQ ID NO: 33) or HAO 25-26L.1434 meganuclease (amino acid sequence set forth in SEQ ID NO: 11 and codon optimized nucleic acid sequence set forth in SEQ ID NO: 34), a sequence encoding a codon optimized 7 amino acid minimal C terminal SV40 NLS (amino acid sequence set forth in SEQ ID NO: 35 and codon optimized nucleic acid sequence set forth in SEQ ID NO: 71), a 3' human SNRPB transcript variant 1 UTR (SEQ ID NO: 63), and a 140 base pair poly A tail. The nucleic acid coding sequence of the meganucleases in the improved mRNA were further modified using alternative codon sequences to reduce uridine content, while leaving the amino acid sequence identical. Similar to the unmodified mRNA, the optimized coding sequence for the 10 amino acid N terminal SV40 NLS comprises a codon optimized sequence encoding a 7 amino acid minimal SV40 NLS sequence (amino acid sequence set forth in SEQ ID NO: 35 and codon optimized nucleic acid sequence set forth in SEQ ID NO: 71) flanked by a methionine and an alanine residue at the 5' end and a histidine residue at the 3' end. In this improved mRNA, the codon for the flanking alanine has been modified from GCA to GCC. Additionally, in both the 10 and 7 amino acid SV40 NLS sequences, the codon encoding the proline has been modified from CCG to CCC.

Each mRNA in the un-improved mRNA and improved mRNA contained N1-methylpseudouridine and a 7-methylguanosine cap. Sequences of the control unmodified mRNA encoding the HAO 25-26L.1128 meganuclease and the HAO 25-26L.1434 meganuclease are provided in SEQ ID NOs: 64 and 65, respectively. Sequences of the improved mRNA (denoted as "MAX") encoding the HAO 25-26L.1128 meganuclease and the HAO 25-26L.1434 meganuclease are provided in SEQ ID NOs: 66 and 67, respectively. Each mRNA encoding the meganucleases were electroporated into HepG2 at a dosage of 0.1 ng, 0.5 ng, 2 ng, 10 ng, 50 ng, and 100 ng using the Lonza Amaxa 4D system.

Cells were collected at seven days post electroporation for gDNA preparation and evaluated for transfection efficiency using a Beckman Coulter CytoFlex S cytometer. Transfection efficiency exceeded 90%. gDNA was prepared using the Macherey Nagel NucleoSpin Blood QuickPure kit.

Digital droplet PCR was utilized to determine the frequency of target insertions and deletions (indel %) using primers P1, F1, and R1 at the HAO 25-26 recognition sequence, as well as primers P2, F2, R2 to generate a reference amplicon. Amplifications were multiplexed in a 20 uL reaction containing 1× ddPCR Supermix for Probes (no dUTP, BioRad), 250 nM of each probe, 900 nM of each primer, 5U of HindIII-HF, and about 50 ng cellular gDNA. Droplets were generated using a QX100 droplet generator (BioRad). Cycling conditions for HAO 25-26 were as follows: 1 cycle of 95° C. (2° C./s ramp) for 10 minutes, 44 cycles of 94° C. (1° C./s ramp) for 30 seconds, 62° C. (1° C./s ramp) for 30 seconds, 72 C (0.2° C./s ramp) for 2 minutes, 1 cycle of 98° C. for 10 minutes, 4° C. hold. Cycling conditions for HAO 3-4 were as follows: 1 cycle of 95° C. (2° C./s ramp) for 10 minutes, 44 cycles of 94° C. (1° C./s ramp) for 30 seconds, 55° C. (1° C./s ramp) for 30 seconds, 72 C (0.2° C./s ramp) for 2 minutes, 1 cycle of 98° C. for 10 minutes, 4° C. hold.

Droplets were analyzed using a QX200 droplet reader (BioRad) and QuantaSoft analysis software (BioRad) was used to acquire and analyze data. Indel frequencies were calculated by dividing the number of positive copies for the binding site probe by the number of positive copies for the reference probe and comparing loss of FAM+ copies in nuclease-treated cells to mock-transfected cells.

```
Primer Sets
P1: 34 HAO 25/26 P1 BS PROBE:
                                    (SEQ ID NO: 39)
TTGGATACAGCTTCCATCTA FAM
```

-continued

```
F1: 21-HAO 25-25-15-16 F2:
                                    (SEQ ID NO: 40)
ACCAAACAAACAGTAAAATTGCC

R1: 14-HAO15-16 25-26 R:
                                    (SEQ ID NO: 41)
GAGGTCGATAAACGTTAGCCTC

P2: 44 12 REF PROBE1:
                                    (SEQ ID NO: 42)
TGTGGTCACCCTCTGCACAGTGT HEX

F2: 28-HAO21-22 F2:
                                    (SEQ ID NO: 43)
CCACATAAGATTTGGCAAGCC

R2: 27-HAO21-22 R2:
                                    (SEQ ID NO: 44)
TGTGGTCACCCTCTGCACAGTGT
```

2. Results

Figure 23:
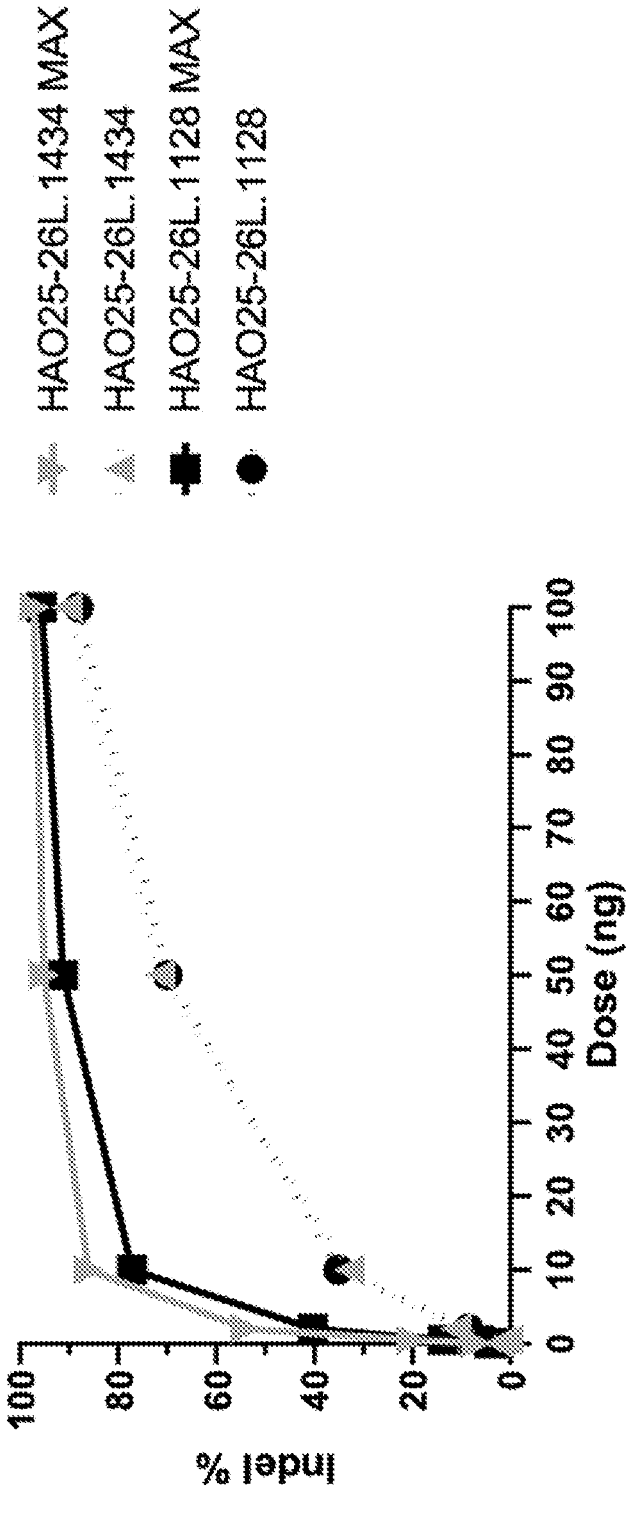
FIG. 23 shows the frequency of indel generation in HepG2 cells at increasing doses of an improved mRNA encoding the HAO 25-26L.1434 or HAO 25-26L.1128 meganucleases. The improved mRNA is denoted as "MAX" and contains an improved combination of a 5' ALB UTR and 3' SNRPB transcript variant 1 UTR sequence as well as codon optimization to reduce uridine content compared to standard mRNA.

In these studies, indels (insertions and deletions) were measured by ddPCR across multiple dosages. The percentage of indels were greatly enhanced using the improved mRNA construct with alternative UTRs and uridine depletion. At a 10 ng dose, the HAO 25-26L.1128 meganuclease generated about 35% indel formation, whereas the modified construct denoted as "MAX" generated about 77% indel formation (FIG. 23). Similarly, the HAO 25-26L.1434 meganuclease at a 10 ng dose generated about 33% indel formation whereas the modified construct encoding the HAO 25-26L.1434 meganuclease denoted as "MAX" generated about 86% indels (FIG. 23). The trend of increased indel formation held across all dosages, but the difference between the two types of mRNA was decreased as the dose increased.

3. Conclusions

These studies demonstrate the ability of the HAO 25-26 meganucleases to generate indels at the HAO 25-26 recognition sequence in HepG2 cells as previously demonstrated. This experiment further shows that modification to mRNA encoding the meganucleases can have a profound effect on indel formation resulting in much greater indel formation at a lower mRNA dosage. This has the advantage of lowering the amount of mRNA needing to be delivered to a target cell as well as lowering potential immunogenicity to the mRNA.

What is claimed is:

1. An engineered meganuclease that binds and cleaves a recognition sequence consisting of SEQ ID NO: 3 within a hydroxyacid oxidase 1 (HAO1) gene, wherein said engineered meganuclease comprises the amino acid sequence of any one of SEQ ID NOs: 5, 6, 7, 10, or 11.

2. A polynucleotide comprising a nucleic acid sequence encoding said engineered meganuclease of claim 1.

3. The polynucleotide of claim 2, wherein said polynucleotide is an mRNA.

4. A recombinant DNA construct comprising a polynucleotide comprising a nucleic acid sequence encoding said engineered meganuclease of claim 1.

5. The recombinant DNA construct of claim 4, wherein said polynucleotide comprises a promoter operably linked to said nucleic acid sequence encoding said engineered meganuclease.

6. The recombinant DNA construct of claim 5, wherein said promoter is a liver-specific promoter.

7. The recombinant DNA construct of claim 6, wherein said liver-specific promoter is a thyroxine-binding globulin (TBG) promoter.

8. A recombinant adeno-associated virus (AAV) comprising a polynucleotide comprising a nucleic acid sequence encoding said engineered meganuclease of claim 1.

9. The recombinant AAV of claim 8, wherein said recombinant AAV comprises an AAV8 capsid.

10. The recombinant AAV of claim 8, wherein said polynucleotide comprises a promoter operably linked to said nucleic acid sequence encoding said engineered meganuclease.

11. The recombinant AAV of claim 10, wherein said promoter is a liver-specific promoter.

12. The recombinant AAV of claim 11, wherein said liver-specific promoter is a TBG promoter.

13. The recombinant AAV of claim 12, wherein said recombinant AAV comprises an AAV8 capsid.

14. A lipid nanoparticle composition comprising lipid nanoparticles comprising a polynucleotide, wherein said polynucleotide comprises a nucleic acid sequence encoding said engineered meganuclease of claim 1.

15. The lipid nanoparticle composition of claim 14, wherein said polynucleotide is an mRNA.

16. A pharmaceutical composition comprising a pharmaceutically acceptable carrier and said polynucleotide of claim 2.

17. A pharmaceutical composition comprising a pharmaceutically acceptable carrier and said mRNA of claim 3.

18. A pharmaceutical composition comprising a pharmaceutically acceptable carrier and said recombinant AAV of claim 8.

19. A pharmaceutical composition comprising a pharmaceutically acceptable carrier and said recombinant AAV of claim 13.

20. A pharmaceutical composition comprising a pharmaceutically acceptable carrier and said lipid nanoparticle composition of claim 14.

21. A pharmaceutical composition comprising a pharmaceutically acceptable carrier and said lipid nanoparticle composition of claim 15.

22. A method for producing a genetically-modified eukaryotic cell comprising a modified HAO1 gene, said method comprising introducing into a eukaryotic cella polynucleotide comprising a nucleic acid sequence encoding an engineered meganuclease of claim 1, wherein said engineered meganuclease is expressed in said eukaryotic cell, wherein said engineered meganuclease produces a cleavage site in said HAO1 gene at a recognition sequence consisting of SEQ ID NO: 3 and generates a modified HAO1 gene, wherein said cleavage site is repaired by non-homologous end joining and said modified HAO1 gene comprises an insertion or deletion that disrupts expression of the encoded HAO1 protein.

23. The method of claim 22, wherein said method is a method for modifying an HAO1 gene in a target cell in a subject, said method comprising delivering to said target cell said polynucleotide comprising a nucleic acid sequence encoding said engineered meganuclease of claim 1, wherein said engineered meganuclease is expressed in said target cell, wherein said engineered meganuclease produces a cleavage site in said HAO1 gene at a recognition sequence consisting of SEQ ID NO: 3 and generates a modified HAO1 gene in said target cell, wherein said cleavage site is repaired by non-homologous end joining and said modified HAO1 gene comprises an insertion or deletion that disrupts expression of the encoded HAO1 protein.

24. The method of claim 22, wherein said method is a method for treating primary hyperoxaluria-1 (PH1) in a subject, wherein said method comprises administering to said subject a therapeutically-effective amount of said polynucleotide comprising a nucleic acid sequence encoding said engineered meganuclease of claim 1, wherein said engineered meganuclease is delivered to a target cell in said subject, wherein said engineered meganuclease is expressed in said target cell, wherein said engineered meganuclease produces a cleavage site in said HAO1 gene at a recognition sequence consisting of SEQ ID NO: 3 and generates a modified HAO1 gene in said target cell, wherein said cleavage site is repaired by non-homologous end joining and said modified HAO1 gene comprises an insertion or deletion that disrupts expression of the encoded HAO1 protein.

* * * * *

SEQUENCE LISTING

```
<160> NUMBER OF SEQ ID NOS: 71

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
```

```
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
145                 150                 155                 160

Ser Ser Pro


<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5


<210> SEQ ID NO 3
<211> LENGTH: 22
<212> TYPE: DNA
<213> ORGANISM: Homo sapiens

<400> SEQUENCE: 3

atggaagctg tatccaagga tg                                              22


<210> SEQ ID NO 4
<211> LENGTH: 22
<212> TYPE: DNA
<213> ORGANISM: Homo sapiens

<400> SEQUENCE: 4

taccttcgac ataggttcct ac                                              22


<210> SEQ ID NO 5
<211> LENGTH: 354
<212> TYPE: PRT
<213> ORGANISM: Artificial Sequence
<220> FEATURE:
<223> OTHER INFORMATION: Synthesized

<400> SEQUENCE: 5

Met Asn Thr Lys Tyr Asn Lys Glu Phe Leu Leu Tyr Leu Ala Gly Phe
1               5                   10                  15

Val Asp Ser Asp Gly Ser Ile Trp Ala Phe Ile Glu Pro Cys Gln Thr
            20                  25                  30

Val Lys Phe Lys His Arg Leu Arg Leu Ser Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
```

```
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Ala Ser
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Arg Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 6
<211> LENGTH: 354
<212> TYPE: PRT
<213> ORGANISM: Artificial Sequence
<220> FEATURE:
<223> OTHER INFORMATION: Synthesized

<400> SEQUENCE: 6

Met Asn Thr Lys Tyr Asn Lys Glu Phe Leu Leu Tyr Leu Ala Gly Phe
1               5                   10                  15

Val Asp Ser Asp Gly Ser Ile Trp Ala His Ile Asp Pro Cys Gln Thr
            20                  25                  30

Val Lys Phe Lys His Arg Leu Arg Leu Ser Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Pro Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Ala Ala
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 7
<211> LENGTH: 354
<212> TYPE: PRT
<213> ORGANISM: Artificial Sequence
<220> FEATURE:
<223> OTHER INFORMATION: Synthesized

<400> SEQUENCE: 7

```
Met Asn Thr Lys Tyr Asn Lys Glu Phe Leu Leu Tyr Leu Ala Gly Phe
1               5                   10                  15

Val Asp Ala Asp Gly Ser Ile Trp Ala Thr Ile Leu Pro Cys Gln Ser
            20                  25                  30

Ala Lys Phe Lys His Arg Leu Lys Leu Gln Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr Val Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110
```

```
Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Ala Ser
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Arg Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 8
<211> LENGTH: 354
<212> TYPE: PRT
<213> ORGANISM: Artificial Sequence
<220> FEATURE:
<223> OTHER INFORMATION: Synthesized

<400> SEQUENCE: 8

Met Asn Thr Lys Tyr Asn Lys Glu Phe Leu Leu Tyr Leu Ala Gly Phe
1               5                   10                  15

Val Asp Ser Asp Gly Ser Ile Trp Ala Thr Ile Asn Pro Cys Gln Pro
            20                  25                  30

Ala Lys Phe Lys His Arg Leu Lys Leu Gln Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr Val Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
```

```
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Cys Ser
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 9
<211> LENGTH: 354
<212> TYPE: PRT
<213> ORGANISM: Artificial Sequence
<220> FEATURE:
<223> OTHER INFORMATION: Synthesized

<400> SEQUENCE: 9

```
Met Asn Thr Lys Tyr Asn Lys Glu Phe Leu Leu Tyr Leu Ala Gly Phe
1               5                   10                  15

Val Asp Ala Asp Gly Ser Ile Tyr Ala Thr Ile Arg Pro Val Gln Arg
            20                  25                  30

Ala Lys Phe Lys His Ser Leu Arg Leu Phe Phe Asn Val Ser Gln Lys
        35                  40                  45

Thr Gln Arg Arg Trp Phe Leu Asp Lys Leu Val Asp Glu Ile Gly Val
    50                  55                  60

Gly Tyr Val Leu Asp Lys Gly Ser Val Ser Tyr Tyr Ile Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Phe Ala Gln Ile Arg Pro Arg Gln Gly His
    210                 215                 220

Lys Phe Lys His Gly Leu Glu Leu Ser Phe Glu Val Thr Gln His Thr
225                 230                 235                 240

Lys Arg Arg Trp Phe Leu Asp Lys Leu Val Asp Glu Ile Gly Val Gly
                245                 250                 255

Tyr Val Tyr Asp Cys Gly Pro Ala Cys Ser Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Arg Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 10
<211> LENGTH: 354
<212> TYPE: PRT
<213> ORGANISM: Artificial Sequence
<220> FEATURE:
<223> OTHER INFORMATION: Synthesized

<400> SEQUENCE: 10

Met Asn Thr Lys Tyr Asn Lys Glu Phe Leu Leu Tyr Leu Ala Gly Phe
1               5                   10                  15

Val Asp Ala Asp Gly Ser Ile Trp Ala His Ile Glu Pro Cys Gln Trp
            20                  25                  30

Val Lys Phe Lys His Arg Leu Arg Leu Ser Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr His Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125
```

```
Val Asp Gln Ile Ala Ala Leu Asn Asp Ser Lys Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Ala Ser
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro
```

<210> SEQ ID NO 11
<211> LENGTH: 354
<212> TYPE: PRT
<213> ORGANISM: Artificial Sequence
<220> FEATURE:
<223> OTHER INFORMATION: Synthesized

<400> SEQUENCE: 11

```
Met Asn Thr Lys Tyr Asn Lys Glu Phe Leu Leu Tyr Leu Ala Gly Phe
1               5                   10                  15

Val Asp Ala Asp Gly Ser Ile Trp Ala Tyr Ile Glu Pro Cys Gln Trp
            20                  25                  30

Val Lys Phe Lys His Arg Leu Lys Leu Gln Leu Asn Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Thr Gly Ser Val Ser Gln Tyr Met Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
```

```
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Lys Ile Arg Pro Gln Gln Ala Ser
    210                 215                 220

Lys Phe Lys His Val Leu Glu Leu Val Phe Glu Val Thr Gln Ser Thr
225                 230                 235                 240

Gln Arg Arg Trp Phe Leu Asp Lys Leu Val Asp Glu Ile Gly Val Gly
                245                 250                 255

Tyr Val Tyr Asp Trp Lys Gln Ala Ser Met Tyr Arg Leu Ser Gln Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro


<210> SEQ ID NO 12
<211> LENGTH: 147
<212> TYPE: PRT
<213> ORGANISM: Artificial Sequence
<220> FEATURE:
<223> OTHER INFORMATION: Synthesized

<400> SEQUENCE: 12

Lys Glu Phe Leu Leu Tyr Leu Ala Gly Phe Val Asp Ser Asp Gly Ser
1               5                   10                  15

Ile Trp Ala Phe Ile Glu Pro Cys Gln Thr Val Lys Phe Lys His Arg
            20                  25                  30

Leu Arg Leu Ser Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Ile Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140
```

Val Leu Asp
145

<210> SEQ ID NO 13
<211> LENGTH: 147
<212> TYPE: PRT
<213> ORGANISM: Artificial Sequence
<220> FEATURE:
<223> OTHER INFORMATION: Synthesized

<400> SEQUENCE: 13

Lys Glu Phe Leu Leu Tyr Leu Ala Gly Phe Val Asp Ser Asp Gly Ser
1               5                   10                  15

Ile Trp Ala His Ile Asp Pro Cys Gln Thr Val Lys Phe Lys His Arg
            20                  25                  30

Leu Arg Leu Ser Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 14
<211> LENGTH: 147
<212> TYPE: PRT
<213> ORGANISM: Artificial Sequence
<220> FEATURE:
<223> OTHER INFORMATION: Synthesized

<400> SEQUENCE: 14

Lys Glu Phe Leu Leu Tyr Leu Ala Gly Phe Val Asp Ala Asp Gly Ser
1               5                   10                  15

Ile Trp Ala Thr Ile Leu Pro Cys Gln Ser Ala Lys Phe Lys His Arg
            20                  25                  30

Leu Lys Leu Gln Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala

```
    130                 135                 140

Val Leu Asp
145


<210> SEQ ID NO 15
<211> LENGTH: 147
<212> TYPE: PRT
<213> ORGANISM: Artificial Sequence
<220> FEATURE:
<223> OTHER INFORMATION: Synthesized

<400> SEQUENCE: 15

Lys Glu Phe Leu Leu Tyr Leu Ala Gly Phe Val Asp Ser Asp Gly Ser
1               5                   10                  15

Ile Trp Ala Thr Ile Asn Pro Cys Gln Pro Ala Lys Phe Lys His Arg
            20                  25                  30

Leu Lys Leu Gln Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Val Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 16
<211> LENGTH: 147
<212> TYPE: PRT
<213> ORGANISM: Artificial Sequence
<220> FEATURE:
<223> OTHER INFORMATION: Synthesized

<400> SEQUENCE: 16

Lys Glu Phe Leu Leu Tyr Leu Ala Gly Phe Val Asp Ala Asp Gly Ser
1               5                   10                  15

Ile Tyr Ala Thr Ile Arg Pro Val Gln Arg Ala Lys Phe Lys His Ser
            20                  25                  30

Leu Arg Leu Phe Phe Asn Val Ser Gln Lys Thr Gln Arg Arg Trp Phe
        35                  40                  45

Leu Asp Lys Leu Val Asp Glu Ile Gly Val Gly Tyr Val Leu Asp Lys
    50                  55                  60

Gly Ser Val Ser Tyr Tyr Ile Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

```
Leu Asn Asp Ser Lys Thr Arg Lys Thr Thr Ser Glu Thr Val Arg Ala
    130                 135                 140

Val Leu Asp
145


<210> SEQ ID NO 17
<211> LENGTH: 147
<212> TYPE: PRT
<213> ORGANISM: Artificial Sequence
<220> FEATURE:
<223> OTHER INFORMATION: Synthesized

<400> SEQUENCE: 17

Lys Glu Phe Leu Leu Tyr Leu Ala Gly Phe Val Asp Ala Asp Gly Ser
1               5                   10                  15

Ile Trp Ala His Ile Glu Pro Cys Gln Trp Val Lys Phe Lys His Arg
            20                  25                  30

Leu Arg Leu Ser Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr His Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 18
<211> LENGTH: 147
<212> TYPE: PRT
<213> ORGANISM: Artificial Sequence
<220> FEATURE:
<223> OTHER INFORMATION: Synthesized

<400> SEQUENCE: 18

Lys Glu Phe Leu Leu Tyr Leu Ala Gly Phe Val Asp Ala Asp Gly Ser
1               5                   10                  15

Ile Trp Ala Tyr Ile Glu Pro Cys Gln Trp Val Lys Phe Lys His Arg
            20                  25                  30

Leu Lys Leu Gln Leu Asn Val Thr Gln Lys Thr Gln Arg Arg Trp Phe
        35                  40                  45

Leu Asp Lys Leu Val Asp Glu Ile Gly Val Gly Tyr Val Arg Asp Thr
    50                  55                  60

Gly Ser Val Ser Gln Tyr Met Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125
```

Leu Asn Asp Ser Lys Thr Arg Lys Thr Thr Ser Glu Thr Val Arg Ala
    130                 135                 140

Val Leu Asp
145

<210> SEQ ID NO 19
<211> LENGTH: 147
<212> TYPE: PRT
<213> ORGANISM: Artificial Sequence
<220> FEATURE:
<223> OTHER INFORMATION: Synthesized

<400> SEQUENCE: 19

Lys Glu Phe Leu Leu Tyr Leu Ala Gly Phe Val Asp Gly Asp Gly Ser
1               5                   10                  15

Ile Tyr Ala Lys Ile Arg Pro Gln Gln Ala Ser Lys Phe Lys His Val
            20                  25                  30

Leu Glu Leu Val Phe Glu Val Thr Gln Ser Thr Gln Arg Arg Trp Phe
        35                  40                  45

Leu Asp Lys Leu Val Asp Glu Ile Gly Val Gly Tyr Val Tyr Asp Trp
    50                  55                  60

Lys Gln Ala Ser Met Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 20
<211> LENGTH: 147
<212> TYPE: PRT
<213> ORGANISM: Artificial Sequence
<220> FEATURE:
<223> OTHER INFORMATION: Synthesized

<400> SEQUENCE: 20

Lys Glu Phe Leu Leu Tyr Leu Ala Gly Phe Val Asp Gly Asp Gly Ser
1               5                   10                  15

Ile Tyr Ala Lys Ile Arg Pro Gln Gln Ala Ala Lys Phe Lys His Val
            20                  25                  30

Leu Glu Leu Val Phe Glu Val Thr Gln Ser Thr Gln Arg Arg Trp Phe
        35                  40                  45

Leu Asp Lys Leu Val Asp Glu Ile Gly Val Gly Tyr Val Tyr Asp Trp
    50                  55                  60

Lys Gln Ala Ser Met Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala

```
        115                 120                 125

Leu Asn Asp Ser Lys Thr Arg Lys Thr Thr Ser Glu Thr Val Arg Ala
    130                 135                 140

Val Leu Asp
145


<210> SEQ ID NO 21
<211> LENGTH: 147
<212> TYPE: PRT
<213> ORGANISM: Artificial Sequence
<220> FEATURE:
<223> OTHER INFORMATION: Synthesized

<400> SEQUENCE: 21

Lys Glu Phe Leu Leu Tyr Leu Ala Gly Phe Val Asp Gly Asp Gly Ser
1               5                   10                  15

Ile Tyr Ala Lys Ile Arg Pro Gln Gln Ala Ser Lys Phe Lys His Val
            20                  25                  30

Leu Glu Leu Val Phe Glu Val Thr Gln Ser Thr Gln Arg Arg Trp Phe
        35                  40                  45

Leu Asp Lys Leu Val Asp Glu Ile Gly Val Gly Tyr Val Tyr Asp Trp
    50                  55                  60

Lys Gln Ala Ser Met Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145


<210> SEQ ID NO 22
<211> LENGTH: 147
<212> TYPE: PRT
<213> ORGANISM: Artificial Sequence
<220> FEATURE:
<223> OTHER INFORMATION: Synthesized

<400> SEQUENCE: 22

Lys Glu Phe Leu Leu Tyr Leu Ala Gly Phe Val Asp Gly Asp Gly Ser
1               5                   10                  15

Ile Tyr Ala Lys Ile Arg Pro Gln Gln Cys Ser Lys Phe Lys His Val
            20                  25                  30

Leu Glu Leu Val Phe Glu Val Thr Gln Ser Thr Gln Arg Arg Trp Phe
        35                  40                  45

Leu Asp Lys Leu Val Asp Glu Ile Gly Val Gly Tyr Val Tyr Asp Trp
    50                  55                  60

Lys Gln Ala Ser Met Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110
```

Pro Asp Lys Phe Leu Glu Val Cys Thr Trp Val Asp Gln Ile Ala Ala
115 120 125

Leu Asn Asp Ser Lys Thr Arg Lys Thr Thr Ser Glu Thr Val Arg Ala
130 135 140

Val Leu Asp
145

<210> SEQ ID NO 23
<211> LENGTH: 147
<212> TYPE: PRT
<213> ORGANISM: Artificial Sequence
<220> FEATURE:
<223> OTHER INFORMATION: Synthesized

<400> SEQUENCE: 23

Lys Glu Phe Leu Leu Tyr Leu Ala Gly Phe Val Asp Gly Asp Gly Ser
1 5 10 15

Ile Phe Ala Gln Ile Arg Pro Arg Gln Gly His Lys Phe Lys His Gly
20 25 30

Leu Glu Leu Ser Phe Glu Val Thr Gln His Thr Lys Arg Arg Trp Phe
35 40 45

Leu Asp Lys Leu Val Asp Glu Ile Gly Val Gly Tyr Val Tyr Asp Cys
50 55 60

Gly Pro Ala Cys Ser Tyr Arg Leu Ser Gln Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
115 120 125

Leu Asn Asp Ser Arg Thr Arg Lys Thr Thr Ser Glu Thr Val Arg Ala
130 135 140

Val Leu Asp
145

<210> SEQ ID NO 24
<211> LENGTH: 147
<212> TYPE: PRT
<213> ORGANISM: Artificial Sequence
<220> FEATURE:
<223> OTHER INFORMATION: Synthesized

<400> SEQUENCE: 24

Lys Glu Phe Leu Leu Tyr Leu Ala Gly Phe Val Asp Gly Asp Gly Ser
1 5 10 15

Ile Tyr Ala Lys Ile Arg Pro Gln Gln Cys Ser Lys Phe Lys His Val
20 25 30

Leu Glu Leu Val Phe Glu Val Thr Gln Ser Thr Gln Arg Arg Trp Phe
35 40 45

Leu Asp Lys Leu Val Asp Glu Ile Gly Val Gly Tyr Val Tyr Asp Trp
50 55 60

Lys Gln Ala Ser Met Tyr Arg Leu Ser Glu Ile Lys Pro Leu His Asn
65 70 75 80

Phe Leu Thr Gln Leu Gln Pro Phe Leu Lys Leu Lys Gln Lys Gln Ala
85 90 95

Asn Leu Val Leu Lys Ile Ile Glu Gln Leu Pro Ser Ala Lys Glu Ser
100 105 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 25
<211> LENGTH: 147
<212> TYPE: PRT
<213> ORGANISM: Artificial Sequence
<220> FEATURE:
<223> OTHER INFORMATION: Synthesized

<400> SEQUENCE: 25

Lys Glu Phe Leu Leu Tyr Leu Ala Gly Phe Val Asp Gly Asp Gly Ser
1               5                   10                  15

Ile Phe Ala Gln Ile Arg Pro Arg Gln Gly His Lys Phe Lys His Gly
            20                  25                  30

Leu Glu Leu Ser Phe Glu Val Thr Gln His Thr Lys Arg Arg Trp Phe
        35                  40                  45

Leu Asp Lys Leu Val Asp Glu Ile Gly Val Gly Tyr Val Tyr Asp Cys
    50                  55                  60

Gly Pro Ala Cys Ser Tyr Arg Leu Ser Gln Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 26
<211> LENGTH: 1065
<212> TYPE: DNA
<213> ORGANISM: Artificial Sequence
<220> FEATURE:
<223> OTHER INFORMATION: Synthesized

<400> SEQUENCE: 26
atgaatacaa aatataataa agagttctta ctctacttag cagggtttgt agactctgac 60
ggttccatct gggcctttat cgagccttgt cagacggtga agttcaagca caggctgagg 120
ctctctctca atgtcactca gaagacacag cgccgttggt tcctcgacaa gctggtggac 180
gagatcggtg tgggttacgt gcgtgacacg ggcagcgtct cccagtacat tctgtccgag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600

```
ctgctctacc tggcgggctt cgtcgacggg gacggctcca tctatgccaa gatccgtcct    660

cagcaagctt ctaagttcaa gcacgttctg gagctcgtgt tcgaggtcac tcagtcgaca    720

cagcgccgtt ggttcctcga caagctggtg gacgagatcg gtgtgggtta cgtgtatgac    780

tggaagcagg cctccatgta ccggctgtcc cagatcaagc ctctgcacaa cttcctgacc    840

cagctccagc ccttcctgaa gctcaagcag aagcaggcca acctcgtgct gaagatcatc    900

gagcagctgc cctccgccaa ggaatccccg gacaagttcc tggaggtgtg cacctgggtg    960

gaccagatcg ccgctctgaa cgactccagg acccgcaaga ccacttccga aaccgtccgc   1020

gccgttctag acagtctctc cgagaagaag aagtcgtccc cctaa                   1065


<210> SEQ ID NO 27
<211> LENGTH: 1065
<212> TYPE: DNA
<213> ORGANISM: Artificial Sequence
<220> FEATURE:
<223> OTHER INFORMATION: Synthesized

<400> SEQUENCE: 27

atgaatacaa aatataataa agagttctta ctctacttag cagggtttgt agactctgac     60

ggttccatct gggcccatat cgatccttgt cagacggtga agttcaagca caggctgagg    120

ctctcgctca atgtcactca gaagacacag cgccgttggt tcctcgacaa gctggtggac    180

gagatcggtg tgggttacgt gcgtgacacg ggcagcgtct cccagtacgt tctgtccgag    240

atcaagcctt tgcataattt tttaacacaa ctacaacctt ttctaaaact aaaacaaaaa    300

caagcaaatt tagttttaaa aattattgaa caacttccgt cagcaaaaga atccccggac    360

aaattcttag aagtttgtac atgggtggat caaattgcag ctctgaatga ttcgaagacg    420

cgtaaaacaa cttctgaaac cgttcgtgct gtgctagaca gtttaccagg atccgtggga    480

ggtctatcgc catctcaggc atccagcgcc gcatcctcgg cttcctcaag cccgggttca    540

gggatccccg aagcactcag agctggagca ggttccggca ctggatacaa caaggaattc    600

ctgctctacc tggcgggctt cgtcgacggg gacggctcca tctatgccaa gatccgtcct    660

cagcaagcgg ctaagttcaa gcacgttctg gagctcgtgt tcgaggtcac tcagtcgaca    720

cagcgccgtt ggttcctcga caagctggtg gacgagatcg gtgtgggtta cgtgtatgac    780

tggaagcagg cctccatgta ccggctgtcc cagatcaagc ctctgcacaa cttcctgacc    840

cagctccagc ccttcctgaa gctcaagcag aagcaggcca acctcgtgct gaagatcatc    900

gagcagctgc cctccgccaa ggaatccccg gacaagttcc tggaggtgtg cacctgggtg    960

gaccagatcg ccgctctgaa cgactccaag acccgcaaga ccacttccga aaccgtccgc   1020

gccgttctag acagtctctc cgagaagaag aagtcgtccc cctaa                   1065


<210> SEQ ID NO 28
<211> LENGTH: 1065
<212> TYPE: DNA
<213> ORGANISM: Artificial Sequence
<220> FEATURE:
<223> OTHER INFORMATION: Synthesized

<400> SEQUENCE: 28

atgaatacaa aatataataa agagttctta ctctacttag cagggtttgt agacgctgac     60

ggttccatct gggccacgat ccttccttgt cagtctgcga agttcaagca caggctgaag    120

ctccagctca atgtcactca gaagacacag cgccgttggt tcctcgacaa gctggtggac    180
```

gagatcggtg tgggttacgt gcgtgacacg ggcagcgtct cccagtacgt gctgtccgag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgacggg gacggctcca tctatgccaa gatccgtcct 660
cagcaagctt ctaagttcaa gcacgttctg gagctcgtgt tcgaggtcac tcagtcgaca 720
cagcgccgtt ggttcctcga caagctggtg gacgagatcg gtgtgggtta cgtgtatgac 780
tggaagcagg cctccatgta ccggctgtcc cagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccagg acccgcaaga ccacttccga aaccgtccgc 1020
gccgttctag acagtctctc cgagaagaag aagtcgtccc cctaa 1065

<210> SEQ ID NO 29
<211> LENGTH: 1065
<212> TYPE: DNA
<213> ORGANISM: Artificial Sequence
<220> FEATURE:
<223> OTHER INFORMATION: Synthesized

<400> SEQUENCE: 29
atgaatacaa aatataataa agagttctta ctctacttag cagggtttgt agactctgac 60
ggttccatct gggccacgat caatccttgt caacctgcga agttcaagca caggctgaag 120
ctccagctca atgtcactca gaagacacag cgccgttggt tcctcgacaa gctggtggac 180
gagatcggtg tgggttacgt gcgtgacacg ggcagcgtct cccagtacgt gctgtcccag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgacggg gacggctcca tctatgccaa gatccgtcct 660
cagcaatgtt cgaagttcaa gcacgttctg gagctcgtgt tcgaggtcac tcagtcgaca 720
cagcgccgtt ggttcctcga caagctggtg gacgagatcg gtgtgggtta cgtgtatgac 780
tggaagcagg cctccatgta ccggctgtcc gagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccaag acccgcaaga ccacttccga aaccgtccgc 1020
gccgttctag acagtctctc cgagaagaag aagtcgtccc cctaa 1065

<210> SEQ ID NO 30
<211> LENGTH: 1065

<212> TYPE: DNA
<213> ORGANISM: Artificial Sequence
<220> FEATURE:
<223> OTHER INFORMATION: Synthesized

<400> SEQUENCE: 30
atgaatacaa aatataataa agagttctta ctctacttag cagggtttgt agacgctgac 60
ggttccatct atgccacgat ccggcctgtt caaagggcta agttcaagca ctcgctgcgt 120
ctctttttca atgtcagtca gaagacacag cgccgttggt tcctcgacaa gctggtggac 180
gagatcggtg tgggttacgt gctggacaag ggcagcgtct cctattacat tctgtcccag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgatggg gacggctcca tctttgccca gatccggcct 660
aggcaagggc ataagttcaa gcacggcctg gagctctcgt tcgaggtcac tcagcataca 720
aagcgccgtt ggttcctcga caagctggtg gacgagatcg gtgtgggtta cgtgtatgac 780
tgcggcccgg cctgcagcta ccggctgtcc cagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccagg acccgcaaga ccacttccga aaccgtccgc 1020
gccgttctag acagtctctc cgagaagaag aagtcgtccc cctaa 1065

<210> SEQ ID NO 31
<211> LENGTH: 1065
<212> TYPE: DNA
<213> ORGANISM: Artificial Sequence
<220> FEATURE:
<223> OTHER INFORMATION: Synthesized

<400> SEQUENCE: 31
atgaatacaa aatataataa agagttctta ctctacttag cagggtttgt agacgctgac 60
ggttccatct gggcccatat cgagccttgc cagtgggtga agttcaagca caggctgagg 120
ctctctctca atgtcactca gaagacacag cgccgttggt tcctcgacaa gctggtggac 180
gagatcggtg tgggttacgt gcgtgacacg ggcagcgtct cccagtacca tctgtccgag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgacggg gacggctcca tctatgccaa gatccgtcct 660
cagcaagctt ctaagttcaa gcacgttctg gagctcgtgt tcgaggtcac tcagtcgaca 720
cagcgccgtt ggttcctcga caagctggtg gacgagatcg gtgtgggtta cgtgtatgac 780
tggaagcagg cctccatgta ccggctgtcc cagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccaag acccgcaaga ccacttccga aaccgtccgc 1020
gccgttctag acagtctctc cgagaagaag aagtcgtccc cctaa 1065

<210> SEQ ID NO 32
<211> LENGTH: 1065
<212> TYPE: DNA
<213> ORGANISM: Artificial Sequence
<220> FEATURE:
<223> OTHER INFORMATION: Synthesized

<400> SEQUENCE: 32
atgaatacaa aatataataa agagttctta ctctacttag cagggtttgt agacgctgac 60
ggttccatct gggcctatat cgagccttgc cagtgggtga agttcaagca caggctgaag 120
ctccagctca atgtcactca gaagacacag cgccgttggt tcctcgacaa gctggtggac 180
gagatcggtg tgggttacgt gcgtgacacg ggcagcgtct cccagtacat gctgtccgag 240
atcaagcctt tgcataattt tttaacacaa ctacaacctt ttctaaaact aaaacaaaaa 300
caagcaaatt tagttttaaa aattattgaa caacttccgt cagcaaaaga atccccggac 360
aaattcttag aagtttgtac atgggtggat caaattgcag ctctgaatga ttcgaagacg 420
cgtaaaacaa cttctgaaac cgttcgtgct gtgctagaca gtttaccagg atccgtggga 480
ggtctatcgc catctcaggc atccagcgcc gcatcctcgg cttcctcaag cccgggttca 540
gggatctccg aagcactcag agctggagca ggttccggca ctggatacaa caaggaattc 600
ctgctctacc tggcgggctt cgtcgacggg gacggctcca tctatgccaa gatccgtcct 660
cagcaagctt ctaagttcaa gcacgttctg gagctcgtgt tcgaggtcac tcagtcgaca 720
cagcgccgtt ggttcctcga caagctggtg gacgagatcg gtgtgggtta cgtgtatgac 780
tggaagcagg cctccatgta ccggctgtcc cagatcaagc ctctgcacaa cttcctgacc 840
cagctccagc ccttcctgaa gctcaagcag aagcaggcca acctcgtgct gaagatcatc 900
gagcagctgc cctccgccaa ggaatccccg gacaagttcc tggaggtgtg cacctgggtg 960
gaccagatcg ccgctctgaa cgactccaag acccgcaaga ccacttccga aaccgtccgc 1020
gccgttctag acagtctctc cgagaagaag aagtcgtccc cctaa 1065

<210> SEQ ID NO 33
<211> LENGTH: 1062
<212> TYPE: DNA
<213> ORGANISM: Artificial Sequence
<220> FEATURE:
<223> OTHER INFORMATION: Synthesized

<400> SEQUENCE: 33
atgaacacca agtacaacaa ggagttcctg ctgtacctgg ccggcttcgt ggacgccgac 60
ggcagcatct gggcccacat cgagccctgc cagtgggtga agttcaagca ccgcctgcgc 120
ctgagcctga acgtgaccca gaagacccag cgccgctggt tcctggacaa gctggtggac 180
gagatcggcg tgggctacgt gcgcgacacc ggcagcgtga gccagtacca cctgagcgag 240
atcaagcccc tgcacaactt cctgacccag ctgcagccct tcctgaagct gaagcagaag 300
caggccaacc tggtgctgaa gatcatcgag cagctgccca gcgccaagga gagccccgac 360
aagttcctgg aggtgtgcac ctgggtggac cagatcgccg ccctgaacga cagcaagacc 420

```
cgcaagacca ccagcgagac cgtgcgcgcc gtgctggaca gcctgcccgg cagcgtgggc    480

ggcctgagcc ccagccaggc cagcagcgcc gccagcagcg ccagcagcag ccccggcagc    540

ggcatcagcg aggccctgcg cgccggcgcc ggcagcggca ccggctacaa caaggagttc    600

ctgctgtacc tggccggctt cgtggacggc gacggcagca tctacgccaa gatccgcccc    660

cagcaggcca gcaagttcaa gcacgtgctg gagctggtgt tcgaggtgac ccagagcacc    720

cagcgccgct ggttcctgga caagctggtg gacgagatcg gcgtgggcta cgtgtacgac    780

tggaagcagg ccagcatgta ccgcctgagc cagatcaagc ccctgcacaa cttcctgacc    840

cagctgcagc ccttcctgaa gctgaagcag aagcaggcca acctggtgct gaagatcatc    900

gagcagctgc ccagcgccaa ggagagcccc gacaagttcc tggaggtgtg cacctgggtg    960

gaccagatcg ccgccctgaa cgacagcaag acccgcaaga ccaccagcga gaccgtgcgc   1020

gccgttctag acagcctgag cgagaagaag aaaagcagcc cc                      1062
```

<210> SEQ ID NO 34
<211> LENGTH: 1062
<212> TYPE: DNA
<213> ORGANISM: Artificial Sequence
<220> FEATURE:
<223> OTHER INFORMATION: Synthesized

<400> SEQUENCE: 34

```
atgaacacca agtacaacaa ggagttcctg ctgtacctgg ccggcttcgt ggacgccgac     60

ggcagcatct gggcctacat cgagccctgc cagtgggtga agttcaagca ccgcctgaag    120

ctgcagctga acgtgaccca gaagacccag cgccgctggt tcctggacaa gctggtggac    180

gagatcggcg tgggctacgt gcgcgacacc ggcagcgtga gccagtacat gctgagcgag    240

atcaagcccc tgcacaactt cctgacccag ctgcagccct tcctgaagct gaagcagaag    300

caggccaacc tggtgctgaa gatcatcgag cagctgccca gcgccaagga gagccccgac    360

aagttcctgg aggtgtgcac ctgggtggac cagatcgccg ccctgaacga cagcaagacc    420

cgcaagacca ccagcgagac cgtgcgcgcc gtgctggaca gcctgcccgg cagcgtgggc    480

ggcctgagcc ccagccaggc cagcagcgcc gccagcagcg ccagcagcag ccccggcagc    540

ggcatcagcg aggccctgcg cgccggcgcc ggcagcggca ccggctacaa caaggagttc    600

ctgctgtacc tggccggctt cgtggacggc gacggcagca tctacgccaa gatccgcccc    660

cagcaggcca gcaagttcaa gcacgtgctg gagctggtgt tcgaggtgac ccagagcacc    720

cagcgccgct ggttcctgga caagctggtg gacgagatcg gcgtgggcta cgtgtacgac    780

tggaagcagg ccagcatgta ccgcctgagc cagatcaagc ccctgcacaa cttcctgacc    840

cagctgcagc ccttcctgaa gctgaagcag aagcaggcca acctggtgct gaagatcatc    900

gagcagctgc ccagcgccaa ggagagcccc gacaagttcc tggaggtgtg cacctgggtg    960

gaccagatcg ccgccctgaa cgacagcaag acccgcaaga ccaccagcga gaccgtgcgc   1020

gccgttctag acagcctgag cgagaagaag aaaagcagcc cc                      1062
```

<210> SEQ ID NO 35
<211> LENGTH: 7
<212> TYPE: PRT
<213> ORGANISM: Artificial Sequence
<220> FEATURE:
<223> OTHER INFORMATION: Synthesized

<400> SEQUENCE: 35

Pro Lys Lys Lys Arg Lys Val
1               5

<210> SEQ ID NO 36
<211> LENGTH: 21
<212> TYPE: DNA
<213> ORGANISM: Artificial Sequence
<220> FEATURE:
<223> OTHER INFORMATION: Synthesized

<400> SEQUENCE: 36
ccgaagaaga agcgcaaggt g 21

<210> SEQ ID NO 37
<211> LENGTH: 10
<212> TYPE: PRT
<213> ORGANISM: Artificial Sequence
<220> FEATURE:
<223> OTHER INFORMATION: Synthesized

<400> SEQUENCE: 37

Met Ala Pro Lys Lys Lys Arg Lys Val His
1               5                   10

<210> SEQ ID NO 38
<211> LENGTH: 30
<212> TYPE: DNA
<213> ORGANISM: Artificial Sequence
<220> FEATURE:
<223> OTHER INFORMATION: Synthesized

<400> SEQUENCE: 38
atggcaccga agaagaagcg caaggtgcat 30

<210> SEQ ID NO 39
<211> LENGTH: 20
<212> TYPE: DNA
<213> ORGANISM: Artificial Sequence
<220> FEATURE:
<223> OTHER INFORMATION: Synthesized

<400> SEQUENCE: 39
ttggatacag cttccatcta 20

<210> SEQ ID NO 40
<211> LENGTH: 23
<212> TYPE: DNA
<213> ORGANISM: Artificial Sequence
<220> FEATURE:
<223> OTHER INFORMATION: Synthesized

<400> SEQUENCE: 40
accaaacaaa cagtaaaatt gcc 23

<210> SEQ ID NO 41
<211> LENGTH: 22
<212> TYPE: DNA
<213> ORGANISM: Artificial Sequence
<220> FEATURE:
<223> OTHER INFORMATION: Synthesized

<400> SEQUENCE: 41
gaggtcgata aacgttagcc tc 22

<210> SEQ ID NO 42
<211> LENGTH: 23

<212> TYPE: DNA
<213> ORGANISM: Artificial Sequence
<220> FEATURE:
<223> OTHER INFORMATION: Synthesized

<400> SEQUENCE: 42
tgtggtcacc ctctgcacag tgt 23

<210> SEQ ID NO 43
<211> LENGTH: 21
<212> TYPE: DNA
<213> ORGANISM: Artificial Sequence
<220> FEATURE:
<223> OTHER INFORMATION: Synthesized

<400> SEQUENCE: 43
ccacataaga tttggcaagc c 21

<210> SEQ ID NO 44
<211> LENGTH: 23
<212> TYPE: DNA
<213> ORGANISM: Artificial Sequence
<220> FEATURE:
<223> OTHER INFORMATION: Synthesized

<400> SEQUENCE: 44
tgtggtcacc ctctgcacag tgt 23

<210> SEQ ID NO 45
<211> LENGTH: 22
<212> TYPE: DNA
<213> ORGANISM: Artificial Sequence
<220> FEATURE:
<223> OTHER INFORMATION: Synthesized

<400> SEQUENCE: 45
cctgtaatag tcatatatag ac 22

<210> SEQ ID NO 46
<211> LENGTH: 22
<212> TYPE: DNA
<213> ORGANISM: Artificial Sequence
<220> FEATURE:
<223> OTHER INFORMATION: Synthesized

<400> SEQUENCE: 46
tccatctggg atagcaataa cc 22

<210> SEQ ID NO 47
<211> LENGTH: 24
<212> TYPE: DNA
<213> ORGANISM: Artificial Sequence
<220> FEATURE:
<223> OTHER INFORMATION: Synthesized

<400> SEQUENCE: 47
cagccaaagt ttcttcatca tttg 24

<210> SEQ ID NO 48
<211> LENGTH: 24
<212> TYPE: DNA
<213> ORGANISM: Artificial Sequence
<220> FEATURE:
<223> OTHER INFORMATION: Synthesized

<400> SEQUENCE: 48
ttgtaaagtc atttgcttgt tggg 24

<210> SEQ ID NO 49
<211> LENGTH: 20
<212> TYPE: DNA
<213> ORGANISM: Artificial Sequence
<220> FEATURE:
<223> OTHER INFORMATION: Synthesized

<400> SEQUENCE: 49
acagtcttcc tcctacctcg 20

<210> SEQ ID NO 50
<211> LENGTH: 20
<212> TYPE: DNA
<213> ORGANISM: Artificial Sequence
<220> FEATURE:
<223> OTHER INFORMATION: Synthesized

<400> SEQUENCE: 50
aaaaggttcc taggacaccc 20

<210> SEQ ID NO 51
<211> LENGTH: 22
<212> TYPE: DNA
<213> ORGANISM: Artificial Sequence
<220> FEATURE:
<223> OTHER INFORMATION: Synthesized

<400> SEQUENCE: 51
acttccaaag tctatatatg ac 22

<210> SEQ ID NO 52
<211> LENGTH: 21
<212> TYPE: DNA
<213> ORGANISM: Artificial Sequence
<220> FEATURE:
<223> OTHER INFORMATION: Synthesized

<400> SEQUENCE: 52
acagaacagt gaggatgtag a 21

<210> SEQ ID NO 53
<211> LENGTH: 20
<212> TYPE: DNA
<213> ORGANISM: Artificial Sequence
<220> FEATURE:
<223> OTHER INFORMATION: Synthesized

<400> SEQUENCE: 53
acacaccacc aacgtaaaac 20

<210> SEQ ID NO 54
<211> LENGTH: 21
<212> TYPE: DNA
<213> ORGANISM: Artificial Sequence
<220> FEATURE:
<223> OTHER INFORMATION: Synthesized

<400> SEQUENCE: 54
ttcccaggga ctgacaggct c 21

<210> SEQ ID NO 55
<211> LENGTH: 28
<212> TYPE: DNA
<213> ORGANISM: Artificial Sequence
<220> FEATURE:
<223> OTHER INFORMATION: Synthesized

<400> SEQUENCE: 55
atgctccccc ggctaatttg tatcaatg 28

<210> SEQ ID NO 56
<211> LENGTH: 22
<212> TYPE: DNA
<213> ORGANISM: Artificial Sequence
<220> FEATURE:
<223> OTHER INFORMATION: Synthesized

<400> SEQUENCE: 56
acttccaaag tctatatatg ac 22

<210> SEQ ID NO 57
<211> LENGTH: 32
<212> TYPE: DNA
<213> ORGANISM: Artificial Sequence
<220> FEATURE:
<223> OTHER INFORMATION: Synthesized

<400> SEQUENCE: 57
cccccggcta atttgtatca atgattatga ac 32

<210> SEQ ID NO 58
<211> LENGTH: 22
<212> TYPE: DNA
<213> ORGANISM: Artificial Sequence
<220> FEATURE:
<223> OTHER INFORMATION: Synthesized

<400> SEQUENCE: 58
tcaacatcat gcccgttccc ag 22

<210> SEQ ID NO 59
<211> LENGTH: 19
<212> TYPE: DNA
<213> ORGANISM: Artificial Sequence
<220> FEATURE:
<223> OTHER INFORMATION: Synthesized

<400> SEQUENCE: 59
tccagatgga agctgtatc 19

<210> SEQ ID NO 60
<211> LENGTH: 64
<212> TYPE: DNA
<213> ORGANISM: Artificial Sequence
<220> FEATURE:
<223> OTHER INFORMATION: Synthesized

<400> SEQUENCE: 60
cataaaccct ggcgcgctcg cgggccggca ctcttctggt ccccacagac tcagagagaa 60
ccca 64

<210> SEQ ID NO 61
<211> LENGTH: 591
<212> TYPE: DNA
<213> ORGANISM: Artificial Sequence
<220> FEATURE:
<223> OTHER INFORMATION: Synthesized

<400> SEQUENCE: 61
atcaacctct ggattacaaa atttgtgaaa gattgactga tattcttaac tatgttgctc 60
cttttacgct gtgtggatat gctgctttaa tgcctctgta tcatgctatt gcttcccgta 120
cggctttcgt tttctcctcc ttgtataaat cctggttgct gtctctttat gaggagttgt 180
ggcccgttgt ccgtcaacgt ggcgtggtgt gctctgtgtt tgctgacgca acccccactg 240
gctggggcat tgccaccacc tgtcaactcc tttctgggac tttcgctttc cccctcccga 300
tcgccacggc agaactcatc gccgcctgcc ttgcccgctg ctggacaggg gctaggttgc 360
tgggcactga taattccgtg gtgttgtcgg ggaagctgac gtcctttcca gggctgctcg 420
cctgtgttgc caactggatc ctgcgcggga cgtccttctg ctacgtccct tcggctctca 480
atccagcgga cctcccttcc cgaggccttc tgccggttct gcggcctctc ccgcgtcttc 540
gctttcggcc tccgacgagt cggatctccc tttgggccgc ctccccgcct g 591

<210> SEQ ID NO 62
<211> LENGTH: 88
<212> TYPE: DNA
<213> ORGANISM: Artificial Sequence
<220> FEATURE:
<223> OTHER INFORMATION: Synthesized

<400> SEQUENCE: 62
aattattggt taaagaagta tattagtgct aatttccctc cgtttgtcct agcttttctc 60
ttctgtcaac cccacacgcc tttgccac 88

<210> SEQ ID NO 63
<211> LENGTH: 114
<212> TYPE: DNA
<213> ORGANISM: Artificial Sequence
<220> FEATURE:
<223> OTHER INFORMATION: Synthesized

<400> SEQUENCE: 63
actcatcttg gccctcctca gctccctgcc tgtttcccgt aaggctgtac atagtccttt 60
tatctccttg tggcctatga aactggttta taataaactc ttaagagaac atta 114

<210> SEQ ID NO 64
<211> LENGTH: 1915
<212> TYPE: DNA
<213> ORGANISM: Artificial Sequence
<220> FEATURE:
<223> OTHER INFORMATION: Synthesized

<400> SEQUENCE: 64
cataaaccct ggcgcgctcg cgggccggca ctcttctggt ccccacagac tcagagagaa 60
cccaccatgg caccgaagaa gaagcgcaag gtgcatatga atacaaaata taataaagag 120
ttcttactct acttagcagg gtttgtagac gctgacggtt ccatctgggc ccatatcgag 180
ccttgccagt gggtgaagtt caagcacagg ctgaggctct ctctcaatgt cactcagaag 240
acacagcgcc gttggttcct cgacaagctg gtggacgaga tcggtgtggg ttacgtgcgt 300
gacacgggca gcgtctccca gtaccatctg tccgagatca agcctttgca taattttta 360 acacaactac aacctttttct aaaactaaaa caaaaacaag caaatttagt tttaaaaatt 420
attgaacaac ttccgtcagc aaaagaatcc ccggacaaat tcttagaagt ttgtacatgg 480
gtggatcaaa ttgcagctct gaatgattcg aagacgcgta aaacaacttc tgaaaccgtt 540
cgtgctgtgc tagacagttt accaggatcc gtgggaggtc tatcgccatc tcaggcatcc 600
agcgccgcat cctcggcttc ctcaagcccg ggttcaggga tctccgaagc actcagagct 660
ggagcaggtt ccggcactgg atacaacaag gaattcctgc tctacctggc gggcttcgtc 720
gacggggacg gctccatcta tgccaagatc cgtcctcagc aagcttctaa gttcaagcac 780
gttctggagc tcgtgttcga ggtcactcag tcgacacagc gccgttggtt cctcgacaag 840
ctggtggacg agatcggtgt gggttacgtg tatgactgga agcaggcctc catgtaccgg 900
ctgtcccaga tcaagcctct gcacaacttc ctgacccagc tccagccctt cctgaagctc 960
aagcagaagc aggccaacct cgtgctgaag atcatcgagc agctgccctc cgccaaggaa 1020
tccccggaca agttcctgga ggtgtgcacc tgggtggacc agatcgccgc tctgaacgac 1080
tccaagaccc gcaagaccac ttccgaaacc gtccgcgccg ttctagacag tctctccgag 1140
aagaagaagt cgtcccccta aggtaccagc ggccgcatca acctctggat tacaaaattt 1200
gtgaaagatt gactgatatt cttaactatg ttgctccttt tacgctgtgt ggatatgctg 1260
ctttaatgcc tctgtatcat gctattgctt cccgtacggc tttcgttttc tcctccttgt 1320
ataaatcctg gttgctgtct ctttatgagg agttgtggcc cgttgtccgt caacgtggcg 1380
tggtgtgctc tgtgtttgct gacgcaaccc ccactggctg gggcattgcc accacctgtc 1440
aactcctttc tgggactttc gctttccccc tcccgatcgc cacggcagaa ctcatcgccg 1500
cctgccttgc ccgctgctgg acaggggcta ggttgctggg cactgataat tccgtggtgt 1560
tgtcggggaa gctgacgtcc tttccagggc tgctcgcctg tgttgccaac tggatcctgc 1620
gcgggacgtc cttctgctac gtcccttcgg ctctcaatcc agcggacctc ccttcccgag 1680
gccttctgcc ggttctgcgg cctctcccgc gtcttcgctt tcggcctccg acgagtcgga 1740
tctccctttg ggccgcctcc ccgcctgggc gcgccaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaa 1915

<210> SEQ ID NO 65
<211> LENGTH: 1915
<212> TYPE: DNA
<213> ORGANISM: Artificial Sequence
<220> FEATURE:
<223> OTHER INFORMATION: Synthesized

<400> SEQUENCE: 65
cataaaccct ggcgcgctcg cgggccggca ctcttctggt ccccacagac tcagagagaa 60
cccaccatgg caccgaagaa gaagcgcaag gtgcatatga atacaaaata taataaagag 120
ttcttactct acttagcagg gtttgtagac gctgacggtt ccatctgggc ctatatcgag 180
ccttgccagt gggtgaagtt caagcacagg ctgaagctcc agctcaatgt cactcagaag 240
acacagcgcc gttggttcct cgacaagctg gtggacgaga tcggtgtggg ttacgtgcgt 300
gacacgggca gcgtctccca gtacatgctg tccgagatca agcctttgca taattttta 360 acacaactac aacctttct aaaactaaaa caaaaacaag caaatttagt tttaaaaatt 420
attgaacaac ttccgtcagc aaaagaatcc ccggacaaat tcttagaagt ttgtacatgg 480
gtggatcaaa ttgcagctct gaatgattcg aagacgcgta aaacaacttc tgaaaccgtt 540
cgtgctgtgc tagacagttt accaggatcc gtgggaggtc tatcgccatc tcaggcatcc 600
agcgccgcat cctcggcttc ctcaagcccg ggttcaggga tctccgaagc actcagagct 660
ggagcaggtt ccggcactgg atacaacaag gaattcctgc tctacctggc gggcttcgtc 720
gacggggacg gctccatcta tgccaagatc cgtcctcagc aagcttctaa gttcaagcac 780
gttctggagc tcgtgttcga ggtcactcag tcgacacagc gccgttggtt cctcgacaag 840
ctggtggacg agatcggtgt gggttacgtg tatgactgga agcaggcctc catgtaccgg 900
ctgtcccaga tcaagcctct gcacaacttc ctgacccagc tccagccctt cctgaagctc 960
aagcagaagc aggccaacct cgtgctgaag atcatcgagc agctgccctc cgccaaggaa 1020
tccccggaca agttcctgga ggtgtgcacc tgggtggacc agatcgccgc tctgaacgac 1080
tccaagaccc gcaagaccac ttccgaaacc gtccgcgccg ttctagacag tctctccgag 1140
aagaagaagt cgtcccccta aggtaccagc ggccgcatca acctctggat tacaaaattt 1200
gtgaaagatt gactgatatt cttaactatg ttgctccttt tacgctgtgt ggatatgctg 1260
ctttaatgcc tctgtatcat gctattgctt cccgtacggc tttcgttttc tcctccttgt 1320
ataaatcctg gttgctgtct ctttatgagg agttgtggcc cgttgtccgt caacgtggcg 1380
tggtgtgctc tgtgtttgct gacgcaaccc ccactggctg gggcattgcc accacctgtc 1440
aactcctttc tgggactttc gctttccccc tcccgatcgc cacggcagaa ctcatcgccg 1500
cctgccttgc ccgctgctgg acaggggcta ggttgctggg cactgataat tccgtggtgt 1560
tgtcggggaa gctgacgtcc tttccagggc tgctcgcctg tgttgccaac tggatcctgc 1620
gcgggacgtc cttctgctac gtcccttcgg ctctcaatcc agcggacctc ccttcccgag 1680
gccttctgcc ggttctgcgg cctctcccgc gtcttcgctt tcggcctccg acgagtcgga 1740
tctccctttg ggccgcctcc ccgcctgggc gcgccaaaaa aaaaaaaaaa aaaaaaaaaa 1800
aaaaaaaaaa aaaaaaaaaa aaaaaaaaaa aaaaaaaaaa aaaaaaaaaa aaaaaaaaaa 1860
aaaaaaaaaa aaaaaaaaaa aaaaaaaaaa aaaaaaaaaa aaaaaaaaaa aaaaa 1915

<210> SEQ ID NO 66
<211> LENGTH: 1485
<212> TYPE: DNA
<213> ORGANISM: Artificial Sequence
<220> FEATURE:
<223> OTHER INFORMATION: Synthesized

<400> SEQUENCE: 66
aattattggt taaagaagta tattagtgct aatttccctc cgtttgtcct agcttttctc 60
ttctgtcaac cccacacgcc tttgccacca tggcccccaa gaagaagcgc aaggtgcata 120
tgaacaccaa gtacaacaag gagttcctgc tgtacctggc cggcttcgtg gacgccgacg 180
gcagcatctg ggcccacatc gagccctgcc agtgggtgaa gttcaagcac cgcctgcgcc 240
tgagcctgaa cgtgacccag aagacccagc gccgctggtt cctggacaag ctggtggacg 300
agatcggcgt gggctacgtg cgcgacaccg gcagcgtgag ccagtaccac ctgagcgaga 360
tcaagcccct gcacaacttc ctgacccagc tgcagccctt cctgaagctg aagcagaagc 420
aggccaacct ggtgctgaag atcatcgagc agctgcccag cgccaaggag agccccgaca 480
agttcctgga ggtgtgcacc tgggtggacc agatcgccgc cctgaacgac agcaagaccc 540
gcaagaccac cagcgagacc gtgcgcgccg tgctggacag cctgcccggc agcgtgggcg 600
gcctgagccc cagccaggcc agcagcgccg ccagcagcgc cagcagcagc cccggcagcg 660
gcatcagcga ggccctgcgc gccggcgccg gcagcggcac cggctacaac aaggagttcc 720
tgctgtacct ggccggcttc gtggacggcg acggcagcat ctacgccaag atccgccccc 780
agcaggccag caagttcaag cacgtgctgg agctggtgtt cgaggtgacc cagagcaccc 840
agcgccgctg gttcctggac aagctggtgg acgagatcgg cgtgggctac gtgtacgact 900
ggaagcaggc cagcatgtac cgcctgagcc agatcaagcc cctgcacaac ttcctgaccc 960

```
agctgcagcc cttcctgaag ctgaagcaga agcaggccaa cctggtgctg aagatcatcg   1020

agcagctgcc cagcgccaag gagagccccg acaagttcct ggaggtgtgc acctgggtgg   1080

accagatcgc cgccctgaac gacagcaaga cccgcaagac caccagcgag accgtgcgcg   1140

ccgttctaga cagcctgagc gagaagaaga aaagcagccc ccccaagaag aagcgcaagg   1200

tgtaataagg taccagcggc cgcactcatc ttggccctcc tcagctccct gcctgtttcc   1260

cgtaaggctg tacatagtcc ttttatctcc ttgtggccta tgaaactggt ttataataaa   1320

ctcttaagag aacattaggc gcgccaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaa                   1485


<210> SEQ ID NO 67
<211> LENGTH: 1485
<212> TYPE: DNA
<213> ORGANISM: Artificial Sequence
<220> FEATURE:
<223> OTHER INFORMATION: Synthesized

<400> SEQUENCE: 67

aattattggt taaagaagta tattagtgct aatttccctc cgtttgtcct agcttttctc     60

ttctgtcaac cccacacgcc tttgccacca tggcccccaa gaagaagcgc aaggtgcata    120

tgaacaccaa gtacaacaag gagttcctgc tgtacctggc cggcttcgtg gacgccgacg    180

gcagcatctg ggcctacatc gagccctgcc agtgggtgaa gttcaagcac cgcctgaagc    240

tgcagctgaa cgtgacccag aagacccagc gccgctggtt cctggacaag ctggtggacg    300

agatcggcgt gggctacgtg cgcgacaccg gcagcgtgag ccagtacatg ctgagcgaga    360

tcaagcccct gcacaacttc ctgacccagc tgcagccctt cctgaagctg aagcagaagc    420

aggccaacct ggtgctgaag atcatcgagc agctgcccag cgccaaggag agccccgaca    480

agttcctgga ggtgtgcacc tgggtggacc agatcgccgc cctgaacgac agcaagaccc    540

gcaagaccac cagcgagacc gtgcgcgccg tgctggacag cctgcccggc agcgtgggcg    600

gcctgagccc cagccaggcc agcagcgccg ccagcagcgc cagcagcagc cccggcagcg    660

gcatcagcga ggccctgcgc gccggcgccg gcagcggcac cggctacaac aaggagttcc    720

tgctgtacct ggccggcttc gtggacggcg acggcagcat ctacgccaag atccgccccc    780

agcaggccag caagttcaag cacgtgctgg agctggtgtt cgaggtgacc cagagcaccc    840

agcgccgctg gttcctggac aagctggtgg acgagatcgg cgtgggctac gtgtacgact    900

ggaagcaggc cagcatgtac cgcctgagcc agatcaagcc cctgcacaac ttcctgaccc    960

agctgcagcc cttcctgaag ctgaagcaga agcaggccaa cctggtgctg aagatcatcg   1020

agcagctgcc cagcgccaag gagagccccg acaagttcct ggaggtgtgc acctgggtgg   1080

accagatcgc cgccctgaac gacagcaaga cccgcaagac caccagcgag accgtgcgcg   1140

ccgttctaga cagcctgagc gagaagaaga aaagcagccc ccccaagaag aagcgcaagg   1200

tgtgataagg taccagcggc cgcactcatc ttggccctcc tcagctccct gcctgtttcc   1260

cgtaaggctg tacatagtcc ttttatctcc ttgtggccta tgaaactggt ttataataaa   1320

ctcttaagag aacattaggc gcgccaaaaa aaaaaaaaaa aaaaaaaaaa aaaaaaaaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaaaaa aaaaa                   1485
```

-continued

```
<210> SEQ ID NO 68
<211> LENGTH: 21
<212> TYPE: DNA
<213> ORGANISM: Artificial Sequence
<220> FEATURE:
<223> OTHER INFORMATION: Synthesized

<400> SEQUENCE: 68

taatacgact cactataagg g                                               21


<210> SEQ ID NO 69
<211> LENGTH: 11
<212> TYPE: DNA
<213> ORGANISM: Artificial Sequence
<220> FEATURE:
<223> OTHER INFORMATION: Synthesized

<400> SEQUENCE: 69

gccaccatgg c                                                          11


<210> SEQ ID NO 70
<211> LENGTH: 30
<212> TYPE: DNA
<213> ORGANISM: Artificial Sequence
<220> FEATURE:
<223> OTHER INFORMATION: Synthesized

<400> SEQUENCE: 70

atggccccca agaagaagcg caaggtgcat                                      30


<210> SEQ ID NO 71
<211> LENGTH: 21
<212> TYPE: DNA
<213> ORGANISM: Artificial Sequence
<220> FEATURE:
<223> OTHER INFORMATION: Synthesized

<400> SEQUENCE: 71

cccaagaaga agcgcaaggt g                                               21
```